US010221246B2

(12) United States Patent
Pedersen et al.

(10) Patent No.: US 10,221,246 B2
(45) Date of Patent: Mar. 5, 2019

(54) PAN-HER ANTIBODY COMPOSITION

(71) Applicant: Symphogen A/S, Ballerup (DK)

(72) Inventors: Mikkel Wandahl Pedersen, Alleroed (DK); Ida K. Christensen, Copenhagen (DK); Johan Lantto, Lund (SE); Helle Jacobsen, Virum (DK); Michael Kragh, Copenhagen (DK)

(73) Assignee: Symphogen A/S, Ballerup (DK)

( * ) Notice: Subject to any disclaimer, the term of this patent is extended or adjusted under 35 U.S.C. 154(b) by 0 days.

(21) Appl. No.: 15/361,571

(22) Filed: Nov. 28, 2016

(65) Prior Publication Data

US 2017/0152322 A1  Jun. 1, 2017

Related U.S. Application Data

(60) Division of application No. 14/863,292, filed on Sep. 23, 2015, which is a continuation of application No. 13/286,471, filed on Nov. 1, 2011, now Pat. No. 9,155,802.

(60) Provisional application No. 61/531,407, filed on Sep. 6, 2011, provisional application No. 61/408,782, filed on Nov. 1, 2010.

(30) Foreign Application Priority Data

Sep. 5, 2011   (DK) ................................ 2011000675

(51) Int. Cl.
| A61K 39/395 | (2006.01) |
| C07K 16/32 | (2006.01) |
| C07K 16/28 | (2006.01) |
| A61K 45/06 | (2006.01) |
| A61N 5/10 | (2006.01) |
| C07K 16/30 | (2006.01) |
| C07K 16/40 | (2006.01) |
| A61K 47/68 | (2017.01) |
| A61K 39/00 | (2006.01) |

(52) U.S. Cl.
CPC .......... *C07K 16/32* (2013.01); *A61K 39/3955* (2013.01); *A61K 39/39558* (2013.01); *A61K 45/06* (2013.01); *A61K 47/6845* (2017.08); *A61K 47/6851* (2017.08); *A61N 5/10* (2013.01); *C07K 16/2863* (2013.01); *C07K 16/30* (2013.01); *C07K 16/303* (2013.01); *C07K 16/3015* (2013.01); *C07K 16/3053* (2013.01); *C07K 16/3069* (2013.01); *C07K 16/40* (2013.01); *A61K 2039/507* (2013.01); *C07K 2317/24* (2013.01); *C07K 2317/565* (2013.01); *C07K 2317/73* (2013.01); *C07K 2317/76* (2013.01)

(58) Field of Classification Search
None
See application file for complete search history.

(56) References Cited

U.S. PATENT DOCUMENTS

| 7,749,697 | B2 | 7/2010 | Oleksiewicz et al. |
| 7,887,805 | B2* | 2/2011 | Pedersen .......... A61K 39/39558 424/143.1 |
| 8,283,294 | B2 | 10/2012 | Kastrup et al. |
| 8,414,896 | B2* | 4/2013 | Pedersen .......... A61K 39/39558 424/143.1 |
| 8,609,095 | B2* | 12/2013 | Pedersen .............. A61K 39/395 424/138.1 |
| 8,663,640 | B2* | 3/2014 | Pedersen ................ C07K 14/71 424/133.1 |
| 8,691,225 | B2 | 4/2014 | Schoeberl et al. |
| 9,217,039 | B2* | 12/2015 | Pedersen ................ C07K 16/40 |
| 9,527,913 | B2 | 12/2016 | Lantto et al. |
| 2007/0178102 | A1 | 8/2007 | Yarden et al. |
| 2008/0299581 | A1 | 12/2008 | Nielsen et al. |
| 2010/0310558 | A1 | 12/2010 | Oleksiewicz et al. |
| 2011/0129855 | A1 | 6/2011 | Pedersen et al. |
| 2016/0089435 | A1 | 3/2016 | Pedersen et al. |
| 2017/0165365 | A1 | 6/2017 | Lantto et al. |

FOREIGN PATENT DOCUMENTS

| CN | 100408097 C | 8/2008 |
| CN | 1703243 B | 5/2011 |
| WO | 2000078347 | 12/2000 |
| WO | 2004008099 | 1/2004 |
| WO | WO 2004/008099 | * 1/2004 |

(Continued)

OTHER PUBLICATIONS

Arpino et al., "Treatment of human epidermal growth factor receptor 2-overexpressing breast cancer xenografts with multiagent HER-targeted therapy," Journal of National Cancer Institute, 99(6):694-705 (2007).
Baselga et al., "Novel anticancer targets: revisiting ERBB2 and discovering ERBB3," Nature Reviews—Cancer, 9:463-475 (2009).
Ben-Kasus et al., "Persistent elimination of ErbB-2/HER2-overexpressing tumors using combinations of monoclonal antibodies: relevance of receptor endocytosis," Proceedings of the National Academy of Sciences, 106(9):3294-3299 (2009).
Bhattacharyya et al., "Nanoconjugation modulates the trafficking and mechanism of antibody induced receptor endocytosis," PNAS 107(33):14541-14546 (2010).

(Continued)

*Primary Examiner* — Laura B Goddard
(74) *Attorney, Agent, or Firm* — Steptoe & Johnson LLP; Z. Ying Li; Wyan-Ching M. Lee

(57) ABSTRACT

The present invention is directed to improved therapeutics against receptors within the EGFR/ErbB/HER family that more broadly interfere with multiple members of the HER family (pan-HER inhibition). More particularly, the invention is directed to the use of antibody compositions for human cancer therapy. In vitro studies have shown that the antibody compositions of the invention targeting multiple HER family receptors are superior to antibody compositions targeting only one HER family receptor.

8 Claims, 23 Drawing Sheets

Specification includes a Sequence Listing.

(56) References Cited

FOREIGN PATENT DOCUMENTS

| WO | 2004032960 | 4/2004 |
| WO | 2004032961 | 4/2004 |
| WO | 2005099756 | 10/2005 |
| WO | 2007076923 | 7/2007 |
| WO | 2007077028 | 7/2007 |
| WO | 2008031531 | 3/2008 |
| WO | 2008104183 | 9/2008 |
| WO | 2010022736 | 3/2010 |
| WO | 2010108127 | 9/2010 |
| WO | 2011060206 | 5/2011 |
| WO | 2011107957 | 9/2011 |
| WO | 2012059857 | 5/2012 |
| WO | 2012125573 | 9/2013 |

OTHER PUBLICATIONS

Coyne et al., "Dual potency anti-HER2/neu and anti-EGFR anthracycline immunoconjugates in chemotherapeutic-resistant mammary carcinoma combined with cyclosporine-A and verapamil P-glycoprotein inhibition," Journal of Drug Targeting, 17(6):474-489 (2009).

Friedman et al., "Synergistic down-regulation of receptor tyrosine kinases by combinations of mAbs: implications for cancer immunotherapy," Proceedings of the National Academy of Sciences, 102(6):1915-1920 (2005).

Half et al., "Anti-EGFR and ErbB-2 antibodies attenuate cyclooxygenase-2 expression and cooperatively inhibit survival of human colon cancer cells," Cancer Letters, 251(2):237-246 (2006).

Huang et al., "A pan-HER approach for cancer therapy: background, current status and future development," Expert Opinion on Biological Therapy 9(1):97-110 (2009).

Huhalov et al., "MM-111, an Erb82/Erb83 bispecific antibody with potent activity in Erb82-overexpressing cells, positively combines with trastuzumab to inhibit growth of breast cancer cells driven by the Erb82/Erb83 oncogenic unit," AACR, Annual Meeting, Presentation Abstract, 2 pages, American Association for Cancer Research, United States (2010).

Kawaguchi et al., "Targeting EGFR and HER-2 with cetuximab- and trastuzumab-mediated immunotherapy in pesophageal squamous cell carcinoma," British Journal of Cancer, 97:494-501 (2007).

Khan et al., "Microbead arrays for the analysis of ErbB receptor tyrosine kinase activation and dimerization in breast cancer cells," Assays and Drug Development Technologies, 8(1):27-36 (2010).

Kuwada et al., "Effects of Trastuzumab on Epidermal Growth Factor Receptor-Dependent and -Independent Human Colon Cancer Cells," International Journal of Cancer, I09:291-301 (2004).

Larbouret et al., "In Vivo Therapeutic Synergism of Anti-Epidermal Growth Factor Receptor and Anti-HER2 Monoclonal Antibodies against Pancreatic Carcinomas," Clinical Cancer Research, 13:3356-3362 (2007).

Larbouret et al., "Combined cetuximab and trastuzumab are superior to gemcitabine in the treatment of human pancreatic carcinoma xenografts," Annals of Oncology 21(1):98-103 (2010).

Larbouret et al., "In pancreatic carcinoma, dual EGFR/HER2 targeting with cetuximab/trastuzumab is more effective than treatment with trastuzumab/erlotinib or lapatinib alone: implication of receptors' down-regulation and dimers' disruption," Neoplasia, 14(2):121-130 (2012).

Maneval et al., "Pan-HER Biologics (Hermodulins) for the Treatment of Cancer," Drug Development Research, 69:472-479 (2008).

Meira et al., "Combination of cetuximab with chemoradiation, trastuzumab or MAPK inhibitors: mechanisms of sensitisation of cervical cancer cells," British Journal of Cancer, 101:782-791 (2009).

Narayan et al., "Trastuzumab-Induced HER Reprogramming in "Resistant" Breast Carcinoma Cells," Cancer Research, 69(6):2191-2194 (2009).

Normanno et al., "Cooperative inhibitory effect of ZD1839 (Iressa) in combination with trastuzumab (Herceptin) on human breast cancer cell growth," Annals of Oncology, 13:65-72 (2002).

Patel et al., "Anti-epidermal growth factor receptor monoclonal antibody cetuximab inhibits EGFR/HER-2 heterodimerization and activation," International Journal of Oncology, 34:25-32 (2009).

Pedersen et al., "Sym004: A Novel Synergistic Anti-Epidermal Growth Factor Receptor Antibody Mixture with Superior Anticancer Efficacy," Cancer Research, 70(2):588-597 (2010).

Schoeberl et al., "An ErbB3 antibody, MM-121, is active in cancers with ligand-dependent activation," Cancer Research 70(6):2485-2494 (2010).

United States Patent and Trademark Office, "Notice of Allowance and Fee(s) Due," U.S. Appl. No. 13/286,471, dated Jun. 3, 2015.

United States Patent and Trademark Office, "Notice of Allowability," U.S. Appl. No. 13/286,471, dated Jun. 3, 2015.

Ye et al., "Augmentation of a humanized Anti-HER2 mAb 4D5 induced growth inhibition by a human-mouse chimeric anti-EGF receptor mAb C225," Oncogene, 18:731-738 (1999).

Yoshida et al., "Matuzumab and cetuximab activate the epidermal growth factor receptor but fail to trigger downstream signaling by Akt or Erk," International Journal of Cancer, 122:1530-1538 (2008).

Zhu et al.,"Controlled internalization of Her-2/ neu receptors by cross-linking for targeted delivery," Cancer Biology & Therapy, 6(12):1960-1966 (2007).

\* cited by examiner

PAN-HER ANTIBODY COMPOSITION

CROSS-REFERENCE TO RELATED APPLICATIONS

This application is a divisional application of U.S. patent application Ser. No. 14/863,292, filed Sep. 23, 2015, which is a continuation application of U.S. patent application Ser. No. 13/286,471, filed Nov. 1, 2011 and issued as U.S. Pat. No. 9,155,802 on Oct. 13, 2015, which claims the benefit of U.S. Provisional Application No. 61/408,782, filed Nov. 1, 2010, U.S. Provisional Application No. 61/531,407, filed Sep. 6, 2011, and Danish Application No. PA 2011 00672, filed Sep. 5, 2011, all of which are incorporated by reference in their entirety.

SEQUENCE LISTING INFORMATION

The content of the electronically submitted sequence listing in ASCII text file (Name: 022675D1041.txt; Size 81,665 bytes; and Date of Creation: Nov. 27, 2016) filed with the application is incorporated by reference in its entirety.

FIELD OF THE INVENTION

The present invention relates to novel recombinant antibodies targeting the epidermal growth factor receptor (EGFR) family and compositions comprising two or more of these antibodies for use in human cancer therapy.

BACKGROUND OF THE INVENTION

The epidermal growth factor receptor family (EGFR or ErbB/HER family) is a subgroup of the receptor tyrosine kinases (RTKs) and consist of four members: EGFR/ErbB, HER2/ErbB2, HER3/ErbB3 and HER4/ErbB4. The members of the EGFR family are closely related single-chain modular glycoproteins with an extracellular ligand binding region, a single transmembrane domain and an intracellular tyrosine kinase. In normal physiological settings the ErbB family regulates key events in coordination of cell growth, differentiation and migration. EGFR, HER2 and HER3 are believed to play crucial roles in the malignant transformation of normal cells and in the continued growth of cancer cells. EGFR and HER2 have been found to be overexpressed by many epithelial cancers. Overexpression of EGFR and HER2 has furthermore been linked to disease progression, reduced survival, poor response and chemotherapy resistance in several human epithelial cancers. The role of HER4 in malignant transformation and cancer progression is controversial and will not be discussed further here.

EGFR and HER2 are validated cancer targets and both monoclonal antibodies and small molecule inhibitors of their tyrosine kinase have been approved for the treatment of various cancers. HER3 is currently being explored as a potential therapeutic target. However, patients who initially respond to these therapies often relapse due to evolution of acquired resistance. Pre-clinical research points to the involvement of the one or both of the non-targeted receptors in the resistance development. Thus, it appears that the ErbB receptors have the ability to replace one another in order to maintain growth stimulatory signaling and a malignant phenotype. Simultaneous targeting of two or all three receptors could therefore be a more efficient way of inhibiting cancer cells with ErbB family dependency.

EGFR is a 170 kDa cell surface glycoprotein consisting of a single polypeptide chain of 1186 amino acid residues as originally determined and described by cloning and sequencing of human cDNAs from a human vulval carcinoma cell line. EGFR contains three major domains: an extracellular domain, a transmembrane domain and an intracellular domain containing the tyrosine kinase. The catalytic activity of EGFR resides in the tyrosine kinase domain (residue 685-953) and is activated upon ligand binding.

The EGFR exists in two different conformations, namely a tethered conformation (closed) and an extended conformation (open). The receptor shifts between the two conformations. In the tethered conformation domain II and IV of the extracellular region of EGFR interact, leaving the receptor in an autoinhibited state. Furthermore, domain III is held at a significant distance from domain I, whereby binding of EGF to both domains simultaneously is impossible. In the extended conformation of EGFR, domain I, II and III are sterically arranged in a C shape, giving room for EGF binding. Furthermore, the conformational changes induce exposure of a β-hairpin consisting of a 20 residue region in domain II, also known as the "dimerization arm". The dimerization arm extending from domain II of the EGFR makes extensive contacts with the domain II of another EGFR, thereby forming an EGFR homodimer.

Dimerization brings the active cytoplasmic tyrosine kinase domains of the receptors close enough for phosphorylation of the tyrosine residues in the regulatory regions of the receptors. Furthermore, the juxtamembrane regions of the two receptors form an antiparallel dimer which has been found to be important in stabilizing the tyrosine kinase dimer. The "receptor-mediated" dimerization mechanism is unique for the ErbB family compared to other tyrosine kinase receptors where "ligand-mediated" dimerization is the more common theme.

A number of modes of activation of the intracellular tyrosine kinase domain of EGFR have been suggested. Unlike other receptor tyrosine kinases, the EGFR tyrosine kinase domain by default adopts a conformation normally observed only in phosphorylated and activated kinases. This indicates that the kinase domain of EGFR is constitutively active. Regulation of a constitutive tyrosine kinase would thus occur through the delivery of a dimerization partner's C-terminal regulator region for trans-phosphorylation. Another possibility is that activation of the tyrosine kinase domain involves displacement of inhibitory interactions that have not been visualized in crystallographic studies. However, crystal structure analyses of the juxtamembrane and tyrosine kinase of EGFR have revealed that an asymmetric dimer of tyrosine kinases formed upon dimerization of two EGFRs is important for regulation of the tyrosine kinase activity. In this asymmetric homodimer one of the tyrosine kinases plays the receiver while the other tyrosine kinase plays the donor. Only the receiver kinase domain has catalytic activity and proceeds to phosphorylate tyrosine residues in the C-terminal tail of the receptor (whether in cis or trans, or both is unknown).

The clathrin-mediated endocytosis is the most important mechanism of down-regulation of EGFR. The destiny of EGFR depends on the stability of the ligand-receptor complex. Upon EGF binding to EGFR the EGFR homodimer is rapidly targeted to clathrin-coated pits and internalized through ligand-induced endocytosis. Simultaneously EGFR is heavily ubiquitinated by the attachment of both monoubiquitin and polyubiquitin. The ubiquitin ligase Cbl is responsible for the ubiquitination of EGFR. Cbl binds either directly or indirectly through an adaptor protein such as Grb2 to phosphorylated tyrosine residues at the regulatory region of EGFR. The binding of Cbl to EGFR via Grb2 is necessary for receptor internalization. Esp15 also play a role in EGFR internalization. The exact role of Esp15 is however still controversial. The ubiquitination is involved in endocytic downregulation of EGFR and endosomal sorting of EGFR to lysosomes. The ubiquitin chains are recognized by the endosomal sorting complex required for transport (ESCRT) and the Hrs/STAM, which retains ubiquinated proteins in the membrane of early endosomes, thereby hindering recycling of EGFR. Subsequently EGFR is sorted into intra luminal vesicles (ILVs) which leads to delivery of EGFR to the late endosome and finally degradation in the lysosomes.

In contrast to the degradation of EGFR when bound to EGF, TGF-α binding allows receptor recycling. The TGF-α ligand dissociates rapidly from EGFR in the early endosome due to the acidic environment, leading to receptor dephosphorylation, de-ubiquitination and thereby recycling of the receptor back to the cell surface. EPR binding to EGFR has the same effect on endocytic sorting of EGFR as TGF-α. HB-EGF and BTC both target all EGFRs for lysosomal degradation while AR causes fast as well as slow EGFR recycling.

Human epidermal growth factor receptor 2 (HER2, ErbB2 or Neu) was first described in 1984 by Schechter et al. HER2 consists of 1234 amino acids and is structurally similar to EGFR with an extracellular domain consisting of four subdomains I-IV, a transmembrane domain, a juxtamembrane domain, an intracellular cytoplasmic tyrosine kinase and a regulatory C-terminal domain.

The domain II-IV contact that restricts the domain arrangement in the tethered EGFR is absent in HER2. Three of the seven conserved residues important for stabilizing the tether in the unactivated EGFR are different in HER2. HER2 thus resembles EGFR in its extended (open) form with the dimerization arm exposed and apparently poised to drive receptor-receptor interactions. The absence of a tethered HER2 conformation indicates that the receptor lacks autoinhibition as seen for the other members of the ErbB family. A stable interface of subdomain I-III seems to keep HER2 in the extended configuration similar to the extended configuration of the EGFR-EGF complex. The interaction between domains I and III involves regions corresponding to ligand-binding sites in domains I and III of EGFR, leaving no space sterically for ligands, rendering HER2 incapable of binding ligands. Domains II and IV form two distinct interfaces that stabilize the heterodimer formation of HER2 and another member of the ErbB family.

Biophysical studies have failed to detect significant HER2 homodimerization in solution or in crystals. The residues of domain II of EGFR and HER2 are similar. However Arg285 at the dimer interface is not conserved between EGFR and HER2. In HER2 residue 285 is Leu. Mutation studies indicate that Leu at this position is partly responsible for the absence of HER2 homodimers in solution. Dimerization of intact HER2 in vivo may require additional interactions of sites in the transmembrane domain of HER2.

HER2 is the only member of the ErbB family that does not bind known ligands. HER2 is instead activated via formation of heteromeric complexes with other ErbB family members and thereby indirectly regulated by EFGR and HER3 ligands. HER2 is the preferred heterodimerization partner of the three other ErbB receptors. HER2 enhances the affinity of the other ErbB receptors for their ligands by slowing down the rate of ligand-receptor complex dissociation, whereby HER2 enhances and prolongs signaling. The ability of HER2 to enhance the ligand affinity of other ErbB receptors may reflect the promiscuous behavior of HER2 as a heterodimerization partner. Heterodimerization of HER2 and another ligand-bound receptor of the ErbB family induces cross-phosphorylation, leading to phosphorylation of the C-terminal tyrosine residues. The most active HER2 heterodimer is the HER2-HER3 complex. HER2 complements the kinase-deficient HER3 by providing an active kinase.

In contrast to EGFR, HER2 is internalization resistant when overexpressed. Overexpression of HER2 has further been reported to inhibit endocytosis of the other ErbB family members. Two mechanisms by which HER2 escapes lysosomal degradation and thereby remains at the plasma membrane have been suggested. Either HER2 avoids internalization or it becomes efficiently recycled from endosomes back to the plasma membrane. Studies using labeled antibodies have shown that HER2 is constantly internalized and recycled. Other studies in contrast failed to identify intracellular HER2 in cells treated with compounds known to inhibit recycling.

It has been proposed that the carboxyl terminus of HER2 does not possess all signals required for internalization or that it contains an inhibitory signal essential for clathrin-mediated endocytosis. Additionally, studies have shown that HER2 heterodimers are not delivered to endosomes. A Cbl docking site like the one found on EGFR has also been identified on HER2 (Y1112). Thereby Cbl can be recruited to HER2, leading to ubiquitination of HER2, but the actual binding efficiency of Cbl is unclear. It has been proposed that HER2 is internalization resistant due to its association with membrane protrusions. Finally, other studies have shown that the endocytosis resistance of HER2-EGFR heterodimers is associated with inefficient EGF-induced formation of clathrin-coated pits.

The third member of the ErbB family, known as human epidermal growth factor receptor 3 (HER3, ErbB3) was identified in 1989 by Kraus M. H. et al. The HER3 gene encodes a protein of 1342 amino acids with striking structural similarities to EGFR and HER2. Features such as overall size, four extracellular subdomains (I-IV) with two cysteine clusters (domains II and IV), and a tyrosine kinase domain show structural similarities to EGFR and HER2. The tyrosine kinase domain of HER3 shows 59% sequence homology to the tyrosine kinase domain of EGFR.

Just like EGFR, HER3 exists in a tethered conformation and in an extended conformation. In the tethered conformation the dimerization arm is buried by interactions with domain IV, leaving domains I and III too far apart for efficient ligand binding. Ligand binding to the extracellular domains I and III occurs in the extended conformation of HER3 and leads to heterodimerization with other members of the ErbB family. No HER3 homodimers are formed upon ligand binding. The extended and ligand-bound HER3 molecule preferentially heterodimerizes with HER2.

In contrast to EGFR and HER2, the tyrosine kinase of HER3 has impaired catalytic activity, insufficient for any detectable biological response. Two amino acid residues which are highly conserved in the catalytic domains of protein kinases are altered in the catalytic domain of HER3. These are the substitution of aspargine for aspartic acid at residue 815 and substitution of histamine for glutamate at residue 740. The two amino acid substitutions may be the reason why HER3 lacks catalytic activity of its tyrosine kinase domain. Because of the impaired intrinsic kinase activity of HER3 the receptor needs to heterodimerize with another ErbB family member in order to respond to its own ligand binding.

Little is known about endocytosis of HER3. Moreover, different studies have suggested that HER3 is endocytosis impaired to the same extent as HER2. In agreement with this, the HER3-NRG1 complex was found to be internalized less efficiently and slower than the EGFR-EGF complex, supporting the view that HER3 is not endocytosed as efficiently as EGFR. However, when the C-terminal tail of EGFR was replaced with the C-terminal tail of HER3, EGFR became endocytosis impaired, suggesting that a region in the C-terminus of HER3 protects the receptor against internalization. It has also been suggested that NRG1 does not efficiently target HER3 to degradation due to the dissociation of the ligand-receptor complexes in endosomes, as it is observed when EGF is activated by TGFα.

Targeting the ErbB family has been intensely pursued in the last decade as a cancer treatment strategy. Different treatment modalities have been explored such as tyrosine kinase inhibitors (TKIs), monoclonal antibodies (mAbs) and ligand-traps. An advantage of monoclonal antibodies for treatment of cancer is the target specificity, ensuring a low toxicity compared to conventional cytotoxic cancer chemotherapy. Monoclonal antibodies have been approved for the treatment of solid tumors with abnormally high levels of EGFR or HER2, and numerous mAbs targeting EGFR or HER2 are in clinical trials. TKIs inhibit receptor signaling by binding to the ATP-binding site in the tyrosine kinase domain of EGFR and HER2. Erlotinib/Tarceva® inhibits tyrosine kinases of EGFR while lapatinib/Tykerb® inhibits tyrosine kinases of both EGFR and HER2. Both erlotinib and laptinib are FDA approved TKIs for use in the treatment of non-small lung cancer (NSCLC) and HER2 overexpressing metastatic breast cancer, respectively.

However, despite the clinical usefulness of monoclonal antibody therapy and TKIs, development of acquired resistance to the treatment is an increasing issue. Combinatory therapy of mAbs and conventional cytotoxic chemotherapy is one of the approaches being carried out in order to increase treatment efficacy. Furthermore, several strategies are being explored to increase the efficacy of monoclonal antibodies, including enhancement of effector functions, and direct and indirect arming of the antibodies with radionuclides or toxins. Another strategy is combinations of mAbs against different targets.

The scientific rationale for dual inhibition of the ErbB receptors is built on a number of preclinical in vitro and in vivo studies which have resulted in superior antitumor activity utilizing a dual ErbB approach rather than single receptor targeting. Simultaneous targeting of multiple epitopes on EGFR and HER2 by monoclonal antibody mixtures has proven superior to mAbs in vitro and in vivo (Friedman et al., PNAS 2005, 102:1915-20) and the combination between the TKI gefitinib, and the two mAbs trastuzumab and pertuzumab provided significantly improved antitumor efficacy compared with any single agent in mice carrying xenograft tumors of HER2-overexpressing breast cancer cells (Arpino et al., J Natl Cancer Inst 2007, 99:694-705).

The ability of co-activation of the receptor tyrosine kinases in the ErbB receptor family has been observed to occur during oncogenic transformation in vitro and appears to play an essential role in development and progression of human primary tumors. The cooperative role of the ErbB family members has furthermore been supported by in vitro and in vivo studies demonstrating that resistance to mAbs and TKIs in ErbB overexpressing cancer cells is associated with increased activity of other ErbB family members. RTK co-activation enables cancer cells to simultaneously activate two or more RTKs in order to attain network robustness and increase the diversity of signaling outcome. RTK co-activation has been recapitulated in multiple cancer types, particularly in the context of acquired resistance to TKIs, suggesting that oncogene switching as a result of RTK co-activation may be a general mechanism by which cancer cells achieve chemoresistance through continued activity of downstream signaling molecules. RTK coactivation has been described further in a study by Pillay et al, Neplasia 2009; 11: 448-58, 2 demonstrating a hierarchy of activated receptor tyrosine kinases, thus allowing for a rapid compensation of a secondary RTK after the inactivation of the dominant RTK. Co-activation of secondary RTKs may occur through autocrine-paracrine growth factor secretion, direct transphosphorylation by the dominant RTK, indirect phosphorylation through a signaling intermediate such as Src, or transcriptional regulation. Examples of dominant RTKs include EGFR and HER2, whereas secondary RTKs may include HER3.

A potential strategy to overcome resistance to mAbs and TKIs used for treatment of cancer with high levels of ErbB family receptors may include simultaneous targeting of multiple ErbB receptors in order to shut down oncogenic RTK signaling and overcome the compensatory mechanism. Such a strategy would induce uncommon perturbations into the robust ErbB signaling network and thereby hopefully overcome development of resistance.

SUMMARY OF THE INVENTION

The present invention is directed to improved therapeutics against receptors within the HER family that more broadly interfere with multiple members of the HER family (pan-HER inhibition). More particularly, the invention is directed to the use of antibody compositions for human cancer therapy, e.g. for the treatment of breast cancer, ovarian cancer, gastric cancer, lung cancer and other cancers with dependency on one or more of the receptors EGFR, HER2 and HER3. Compared to the currently available treatments for such cancers, including available monoclonal and combinations of antibodies as well as small molecules directed against receptors of the HER family, it is contemplated that the antibody composition of the invention may provide a superior clinical response either alone or optionally in combination with other treatments such as chemotherapy.

In one aspect, the invention relates to a recombinant antibody composition, wherein at least one distinct anti-HER antibody molecule binds to an antigen of a first HER family receptor and at least one distinct anti-HER antibody molecule binds to an antigen of a second HER family receptor.

In a further aspect, the invention relates to a recombinant antibody composition, wherein at least one distinct anti-HER antibody molecule binds to an antigen of a first HER family receptor and at least one distinct anti-HER antibody molecule binds to an antigen of a second HER family receptor, and at least one distinct anti-HER antibody molecule binds to an antigen of a third HER family receptor.

Preferably, the invention relates to a recombinant antibody composition, wherein the composition comprises at least one anti-EGFR antibody with CDRs from, or which is capable of inhibiting the binding of and/or which binds the same epitope, as 1254, 1277 or 1565; at least one anti-HER2 antibody with CDRs from, or which is capable of inhibiting the binding of and/or which binds the same epitope as, 4384, 4385, 4517 or 4518; and at least one anti-HER3 antibody with CDRs from, or which is capable of inhibiting the binding of and/or which binds the same epitope as, 5038 or 5082. In a particular preferred embodiment of the invention, the antibody composition comprises antibodies with the CDRs of antibodies 1277+1565+4384+4517+5038+5082, or antibodies that are capable of inhibiting the binding of and/or bind the same epitope as said antibodies.

Representative antibody compositions of the invention have proven effective in inhibition of proliferation of representative cancer cell lines, which is indicative of an in vivo use in the treatment of cancer. These indicative results have been confirmed in a xenograft model of human cancer in mice.

In a further aspect, the invention relates to an immunoconjugate comprising a recombinant antibody composition of the invention conjugated to an anti-cancer agent.

In a further aspect, the invention relates to nucleic acid molecules encoding the antibodies of the invention, expression vectors comprising said nucleic acids and host cells comprising said nucleic acids or expression vectors.

In a further aspect, the invention relates to a method for producing an antibody composition of the invention.

In a still further aspect, the invention relates to a pharmaceutical composition comprising an antibody composition of the invention and a pharmaceutically acceptable carrier.

Furthermore, the invention relates to a method for treating cancer in a human or other mammal comprising administering to a subject in need thereof a therapeutically effective amount of an antibody composition of the invention.

In a still further aspect, the invention relates to an antibody composition of the invention for use as a medicament, for use in treatment of cancer, and/or for use in treatment of cancer in a human or other mammal having acquired resistance to the treatment with antibodies and/or TKIs.

In a further aspect, the invention relates to a pharmaceutical article comprising an antibody composition of the invention and at least one chemotherapeutic or antineoplastic compound as a combination for the simultaneous, separate or successive administration in cancer therapy. It is likely that the antibody composition of the invention can be used for a second line treatment, i.e. after or simultaneously with treatment using conventional chemotherapeutic or antineoplastic agents, or after or simultaneously with radiation therapy and/or surgery.

DETAILED DESCRIPTION OF THE INVENTION

Definitions

Figure 1:
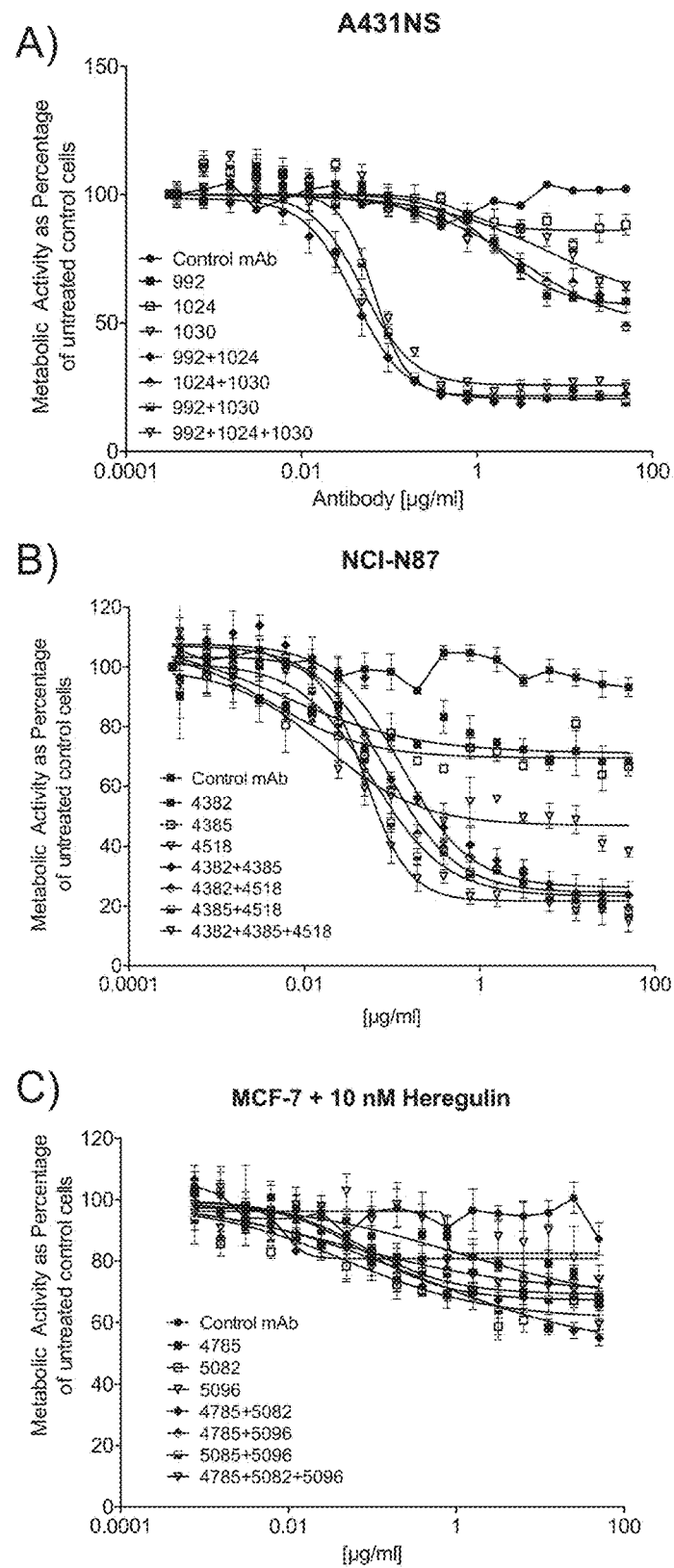
FIG. 1: A) Metabolic activity of A431NS cells treated with different concentrations of the indicated antibodies and antibody mixtures for 96 hours. B) Metabolic activity of NCI-N87 cells treated with different concentrations of the indicated antibodies and antibody mixtures for 96 hours. C) Metabolic activity of MCF7 cells treated with different concentrations of the indicated antibodies and antibody mixtures in the presence of 10 nM heregulin beta for 96 hours.

The term "antibody" or "antibody molecule" describes a functional component of serum and is often referred to either as a collection of molecules (antibodies or immunoglobulin) or as one molecule (the antibody molecule or immunoglobulin molecule). An antibody is capable of binding to or reacting with a specific antigenic determinant (the antigen or the antigenic epitope), which in turn may lead to induction of immunological effector mechanisms. An individual antibody is usually regarded as monospecific, and a composition of antibodies may be monoclonal (i.e., consisting of identical antibody molecules) or polyclonal (i.e., consisting of two or more different antibodies reacting with the same or different epitopes on the same antigen or even on distinct, different antigens). Each antibody has a unique structure that enables it to bind specifically to its corresponding antigen, and all natural antibodies have the same overall basic structure of two identical light chains and two identical heavy chains. Antibodies are also known collectively as immunoglobulins.

The terms "antibody" or "antibodies" as used herein are also intended to include chimeric and single chain antibodies, as well as binding fragments of antibodies, such as Fab, Fv fragments or single chain Fv (scFv) fragments, as well as multimeric forms such as dimeric IgA molecules or pentavalent IgM. Also included are antibody mimetics. An antibody may be of human or non-human origin, for example a murine or other rodent-derived antibody, or a chimeric, humanized or reshaped antibody based e.g. on a murine antibody. Each heavy chain of an antibody typically includes a heavy chain variable region (VH) and a heavy chain constant region. The heavy chain constant region typically includes three domains, referred to as CH1, CH2 and CH3. Each antibody light chain typically includes a light chain variable region (VL) and a light chain constant region. The light chain constant region typically includes a single domain, referred to as CL. The VH and VL regions may be further subdivided into regions of hypervariability ("hypervariable regions", which may be hypervariable in sequence and/or in structurally defined loops). These are also referred to as complementarity determining regions (CDRs), which are interspersed with regions that are more conserved, termed framework regions (FRs). Each VH and VL typically includes three CDRs and four FRs, arranged from the amino terminus to the carboxy terminus in the following order: FR1, CDR1, FR2, CDR2, FR3, CDR3, FR4. The amino acid residues in the variable regions are often numbered using a standardized numbering method known as the Kabat numbering scheme (Kabat et al. (1991) Sequences of Proteins of Immunological Interest, 5th Ed. Public Health Service, National Institutes of Health, Bethesda, Md., USA).

When an antibody is said to be "derived from" or "based on" a specified antibody described herein, this means that the "derived" antibody comprises, depending on the particular context, one of the following: the heavy chain CDR3 sequence of said specified antibody; the heavy chain CDR3 sequence and the light chain CDR3 sequence of said specified antibody; the heavy chain CDR1, CDR2 and CDR3 sequences and light chain CDR1, CDR2 and CDR3 sequences of said specified antibody; or the heavy chain variable region sequence and the light chain variable region sequence of said specified antibody, or a humanized and/or affinity matured variant of said heavy chain variable region sequence and/or light chain variable region sequence, or a heavy chain and/or light chain variable region sequence having at least 80%, 85%, 90% or 95% sequence identity, such as at least 96%, 97%, 98% or 99% sequence identity, with the respective heavy chain and light chain variable region sequences. An antibody that is derived from or based on a specified antibody described herein will generally bind the same epitope as said specified antibody and will preferably exhibit substantially the same activity as said specified antibody. An antibody is considered to bind the same HER epitope as the specified antibody if it competes for binding with said specified antibody.

The specificity of an antibody's interaction with a target antigen resides primarily in the amino acid residues located in the six CDRs of the heavy and light chain. The amino acid sequences within CDRs are therefore much more variable between individual antibodies than sequences outside of CDRs. Because CDR sequences are responsible for most antibody-antigen interactions, it is possible to express recombinant antibodies that mimic the properties of a specific naturally occurring antibody, or more generally any specific antibody with a given amino acid sequence, by constructing expression vectors that express CDR sequences from the specific antibody grafted into framework sequences from a different antibody. As a result, it is possible to "humanize" a non-human antibody and still substantially maintain the binding specificity and affinity of the original antibody. A more detailed discussion of humanization is provided below.

A "chimeric antibody" refers in its broadest sense to an antibody that contains one or more regions from one antibody and one or more regions from one or more other antibodies. As used herein, a "chimeric antibody" is generally an antibody that is partially of human origin and partially of non-human origin, i.e. derived in part from a non-human animal, for example a mouse or other rodent, or an avian such as a chicken. Chimeric antibodies are preferred over non-human antibodies in order to reduce the risk of a human anti-antibody response, e.g. a human anti-mouse antibody response in the case of a murine antibody. An example of a typical chimeric antibody is one in which the variable region sequences are murine sequences derived from immunization of a mouse, while the constant region sequences are human. In the case of a chimeric antibody, the non-human parts, i.e. typically the framework regions of the variable region sequences, may be subjected to further alteration in order to humanize the antibody.

The term "humanize" refers to the fact that where an antibody is wholly or partially of non-human origin, for example a murine antibody obtained from immunization of mice with an antigen of interest or a chimeric antibody based on such a murine antibody, it is possible to replace certain amino acids, in particular in the framework regions and constant domains of the heavy and light chains, in order to avoid or minimize an immune response in humans. It is known that all antibodies have the potential for eliciting a human anti-antibody response, which correlates to some extent with the degree of "humanness" of the antibody in question. Although it is not possible to precisely predict the immunogenicity and thereby the human anti-antibody response of a particular antibody, non-human antibodies tend to be more immunogenic than human antibodies. Chimeric antibodies, where the foreign (usually rodent) constant regions have been replaced with sequences of human origin, have been shown to be generally less immunogenic than antibodies of fully foreign origin, and the trend in therapeutic antibodies is towards humanized or fully human antibodies.

For chimeric antibodies or other antibodies of non-human origin, it is therefore preferred that they be humanized to reduce the risk of a human anti-antibody response. For chimeric antibodies, humanization typically involves modification of the framework regions of the variable region sequences. Amino acid residues that are part of a complementarity determining region (CDR) will typically not be altered in connection with humanization, although in certain cases it may be desirable to alter individual CDR amino acid residues, for example to remove a glycosylation site, a deamidation site or an undesired cysteine residue. N-linked glycosylation occurs by attachment of an oligosaccharide chain to an asparagine residue in the tripeptide sequence Asn-X-Ser or Asn-X-Thr, where X may be any amino acid except Pro. Removal of an N-glycosylation site may be achieved by mutating either the Asn or the Ser/Thr residue to a different residue, preferably by way of conservative substitution. Deamidation of asparagine and glutamine residues can occur depending on factors such as pH and surface exposure. Asparagine residues are particularly susceptible to deamidation, primarily when present in the sequence Asn-Gly, and to a lesser extent in other dipeptide sequences such as Asn-Ala. When such a deamidation site, in particular Asn-Gly, is present in a CDR sequence, it may therefore be desirable to remove the site, typically by conservative substitution to remove one of the implicated residues. Substitution in a CDR sequence to remove one of the implicated residues is also intended to be encompassed by the present invention.

Numerous methods for humanization of an antibody sequence are known in the art; see e.g. the review by Almagro & Fransson (2008) *Front Biosci.* 13: 1619-1633. One commonly used method is CDR grafting, which for e.g. a murine-derived chimeric antibody involves identification of human germline gene counterparts to the murine variable region genes and grafting of the murine CDR sequences into this framework. CDR grafting may be based on the Kabat CDR definitions, although a recent publication (Magdelaine-Beuzelin et al. (2007) *Crit Rev. Oncol Hematol.* 64: 210-225) has suggested that the IMGT definition (www.imgt.org) may improve the result of the humanization. Since CDR grafting may reduce the binding specificity and affinity, and thus the biological activity, of a CDR grafted non-human antibody, back mutations may be introduced at selected positions of the CDR grafted antibody in order to retain the binding specificity and affinity of the parent antibody. Identification of positions for possible back mutations can be performed using information available in the literature and in antibody databases. Amino acid residues that are candidates for back mutations are typically those that are located at the surface of an antibody molecule, while residues that are buried or that have a low degree of surface exposure will not normally be altered. An alternative humanization technique to CDR grafting and back mutation is resurfacing, in which non-surface exposed residues of non-human origin are retained, while surface residues are altered to human residues.

In certain cases, it may also be desirable to alter one or more CDR amino acid residues in order to improve binding affinity to the target epitope. This is known as "affinity maturation" and may optionally be performed in connection with humanization, for example in situations where humanization of an antibody leads to reduced binding specificity or affinity and it is not possible to sufficiently improve the binding specificity or affinity by back mutations alone. Various affinity maturation methods are known in the art, for example the in vitro scanning saturation mutagenesis method described by Burks et al. (1997) *PNAS USA*, vol. 94, pp. 412-417 and the stepwise in vitro affinity maturation method of Wu et al. (1998) *PNAS USA*, vol. 95, pp. 6037-6042.

As noted above, the present invention encompasses humanized antibodies, i.e. antibodies as otherwise described that have been subjected to humanization. These may also be referred to as "humanized variants" of an antibody of the invention. In particular, the terms "heavy chain variable region sequence" and "light chain variable region sequence" as used herein with reference to any specific amino acid sequence are intended to encompass not only that specific sequence but also any humanized variant thereof. Affinity matured variants of the anti-HER antibodies described herein are also intended to be encompassed by the present invention.

As used herein, a reference to a heavy chain variable region sequence or a light chain variable region sequence with a particular minimum level of sequence identity compared to a specified heavy chain or light chain variable region sequence, e.g. having at least 90% or 95% sequence identity with the reference sequence, such as at least 96%, 97%, 98% or 99% sequence identity, is intended to include, but not to be limited to, humanized and/or affinity matured variants of such reference sequence.

The term "recombinant antibody" refers to an antibody that is expressed from a cell or cell line transfected with an expression vector (or possibly more than one expression vector, typically two expression vectors) comprising the coding sequence of the antibody, where said coding sequence is not naturally associated with the cell.

The term "vector" refers to a nucleic acid molecule into which a nucleic acid sequence can be inserted for transport between different genetic environments and/or for expression in a host cell. A vector that carries regulatory elements for transcription of the nucleic acid sequence (at least a suitable promoter) is referred to as an "an expression vector". The terms "plasmid" and "vector" may be used interchangeably. Expression vectors used in the context of the present invention may be of any suitable type known in the art, e.g. a plasmid or a viral vector.

The terms "polyclonal antibody" or "mixture of [monoclonal] antibodies" refer to a composition of two or more different antibody molecules which are capable of binding to or reacting with different specific antigenic determinants on the same or on different antigens. In the context of the present invention, the individual antibodies of a polyclonal antibody bind to different antigenic determinants of the HER family. Preferably the individual antibodies of a polyclonal antibody of the invention bind to different epitopes of the HER family, more preferably distinct and substantially non-overlapping epitopes. The variability of a polyclonal antibody is generally thought to be located in the variable regions of the antibody molecules.

It is well-known in the art that antibodies exist as different isotypes, such as the human isotypes IgG1, IgG2, IgG3, IgG4, IgA1 and IgA2, or the murine isotypes IgG1, IgG2a, IgG2b, IgG3 and IgA. An antibody of the invention may be of any isotype. Although it is possible for the individual antibodies of a polyclonal antibody composition of the invention to include antibodies of more than one isotype, they are preferably all of the same isotype.

The term "HER dependency" refers to a cancer cell with dependency on one or more of the HER family receptors for maintaining malignant properties such as proliferation, growth, motility, invasion, survival and/or chemo resistance. Dependency may be caused by receptor overexpression, receptor mutations, autocrine growth factor production, and/or cross-talk with other receptor systems.

The term "pan-HER" or "pan-HER antibody composition" refers to a composition of antibody molecules which are capable of binding to at least two different antigens on at least two HER family receptors. In the context of the present invention, the individual antibodies of an antibody composition bind to different antigenic determinants of the HER family. Preferably, the individual antibodies of the antibody composition bind to EGFR and HER2, EGFR and HER3, HER2 and HER3, or EGFR, HER2 and HER3, respectively.

The term "HER" stands for "Human Epidermal growth factor Receptor" as described above in the "Background of the invention" section and is used interchangeably with the term "ErbB" to characterize the subgroup of the receptor tyrosine kinases (RTKs) consisting of the four members EGFR/ErbB, HER2/ErbB2, HER3/ErbB3 and HER4/ErbB4. Together, these four receptors constitute the "HER family" receptors. As used herein, it is intended to include variants, isoforms and species homologs of HER.

The term "CDR" or "complementarity determining region" refers to the "hypervariable" regions found in the variable domains of an antibody that are primarily responsible for determining the antibody's binding specificity. See the definition in Lefranc et al. (2003), IMGT unique numbering for immunoglobulin and T cell receptor variable domains and Ig superfamily V-like domains, *Dev. Comp Immunol.* 27, 55-77. Each of the heavy and light chains of an antibody contain three CDR regions, referred to as CDR1, CDR2 and CDR3, of which CDR3 shows the greatest variability.

The term "epitope" is used to describe a part of a larger molecule (e.g. antigen or antigenic site) having antigenic or immunogenic activity in an animal. An epitope having immunogenic activity is a portion of a larger molecule that elicits an antibody response in an animal. An epitope having antigenic activity is a portion of a larger molecule to which an antibody immunospecifically binds as determined by any method known in the art. Antigenic epitopes are not necessarily immunogenic. An antigen is a substance to which an antibody or antibody fragment immunospecifically binds, e.g. a toxin, virus, bacteria, protein or DNA. An antigen or antigenic site often has more than one epitope, unless it is very small, and is often capable of stimulating an immune response. Epitopes may be linear or conformational. A linear epitope generally consists of about 6 to 10 adjacent amino acids on a protein molecule that are recognized by an antibody. In contrast, a conformational epitope consists of amino acids that are not arranged sequentially, but where an antibody recognizes a particular three-dimensional structure. When a protein molecule folds into a three-dimensional structure, the amino acids forming the epitope are juxtaposed, enabling the antibody to recognize the conformational epitope. In a denatured protein only linear epitopes are recognized. A conformational epitope, by definition, must be on the outside of the folded protein.

The term "distinct epitopes" refers to the fact that when two different antibodies of the invention bind distinct epitopes, there is less than 100% competition for antigen binding, preferably less than 80% competition for antigen binding, more preferably less than 50% competition for antigen binding, and most preferably as little competition as possible, such as less than about 25% competition for antigen binding. Antibodies capable of competing with each other for binding to the same antigen may bind the same or overlapping epitopes or may have a binding site in the close vicinity of one another, so that competition is mainly caused by steric hindrance. An analysis for "distinct epitopes" of antibody pairs may be performed by methods known in the art, for example by way of binding experiments under saturating antibody conditions using either FACS (fluorescence activated cell sorting) or other flow cytometry analysis on cells expressing HER families and individual fluorescent labeled antibodies, or by Surface Plasmon Resonance (SPR) using HER family antigen captured or conjugated to a flow cell surface. A method for determining competition between antibodies using SPR is described in the examples.

The distinct epitopes are preferably "non-overlapping" in the sense that two different anti-HER antibodies in a composition of the invention have a sufficiently low competition for antigen binding that the two antibodies are able to bind their respective epitopes simultaneously. It will be understood by persons skilled in the that there can be different degrees of overlap, and that distinct epitopes can be considered to be "non-overlapping" in spite of the presence of some degree of overlap, as long as the respective antibodies are able to substantially bind their epitopes. This is generally considered to be the case when the competition for antigen binding between two antibodies is less than about 50%.

Similarly, an antibody that "competes for binding" with an antibody of the invention may be defined as one that exhibits competition for antigen binding of about 50% or more.

Antibodies binding to different epitopes on the same antigen can have varying effects on the activity of the antigen to which they bind, depending on the location of the epitope. An antibody binding to an epitope in an active site of the antigen may block the function of the antigen completely, whereas another antibody binding at a different epitope may have no or little effect on the activity of the antigen alone. Such antibodies may, however, still activate complement and thereby result in the elimination of the antigen, and may result in synergistic effects when combined with one or more antibodies binding at different epitopes on the same antigen. In the context of the present invention, the epitope is preferably a portion of the extracellular domain of the HER family. Antigens of the present invention are preferably extracellular domain HER family proteins, polypeptides or fragments thereof to which an antibody or antibody fragment immunospecifically binds. A HER family associated antigen may also be an analog or derivative of the extracellular domain of HER polypeptide or fragment thereof to which an antibody or antibody fragment immunospecifically binds.

The term "immunoglobulin" is commonly used as a collective designation of the mixture of antibodies found in blood or serum, but may also be used to designate a mixture of antibodies derived from other sources.

The term "cognate $V_H$ and $V_L$ coding pair" describes an original pair of $V_H$ and $V_L$ coding sequences contained within or derived from the same antibody-producing cell. Thus, a cognate $V_H$ and $V_L$ pair represents the $V_H$ and $V_L$ pairing originally present in the donor from which such a cell is derived. The term "an antibody expressed from a $V_H$ and $V_L$ coding pair" indicates that an antibody or an antibody fragment is produced from a vector, plasmid or other polynucleotide containing the $V_H$ and $V_L$ coding sequence. When a cognate $V_H$ and $V_L$ coding pair is expressed, either as a complete antibody or as a stable fragment thereof, they preserve the binding affinity and specificity of the antibody originally expressed from the cell they are derived from. A library of cognate pairs is also termed a repertoire or collection of cognate pairs, and may be kept individually or pooled.

By "protein" or "polypeptide" is meant any chain of amino acids, regardless of length or post-translational modification. Proteins can exist as monomers or multimers, comprising two or more assembled polypeptide chains, fragments of proteins, polypeptides, oligopeptides, or peptides.

The term "head-to-head promoters" refers to a promoter pair being placed in close proximity so that transcription of two gene fragments driven by the promoters occurs in opposite directions. Head-to-head promoters are also known as bi-directional promoters.

The term "transfection" is herein used as a broad term for introducing foreign DNA into a cell. The term is also meant to cover other functional equivalent methods for introducing foreign DNA into a cell, such as e.g., transformation, infection, transduction or fusion of a donor cell and an acceptor cell.

As used herein, the term "inhibits growth" (e.g., referring to cells) is intended to include any measurable decrease in the proliferation (increase in number of cells) or metabolism of a cell when contacted with the antibody composition of the invention as compared to the growth of the same cells in the absence of said antibody composition, e.g. inhibition of growth of a cell culture by at least about 10%, and preferably more, such as at least about 20% or 30%, more preferably at least about 40% or 50%, such as at least about 60%, 70%, 80%, 90%, 99% or even 100%.

The term "treatment" as used herein refers to administration of an antibody composition of the invention in a sufficient amount to ease, reduce, ameliorate or eradicate (cure) symptoms or disease states. Administration of two or more antibodies of the invention will generally be by way of simultaneous administration of the antibodies, preferably in the form of a composition containing all of the antibodies to be used for treatment. However, it is also possible to administer two or more antibodies of the invention separately. References herein to e.g. administration of a recombinant antibody composition comprising at least two antibodies should therefore be understood as encompassing not only administration of a composition comprising the at least two antibodies as such, but also separate administration of the antibodies. Combinations of two or more antibodies of the invention can thus be administered simultaneously, sequentially or separately.

The percent identity between two sequences, e.g. variable region sequences, refers to the number of identical positions shared by the sequences (calculated as # of identical positions/total # of positions×100), taking into account gaps that must be introduced for optimal alignment of the two sequences. The comparison of sequences and determination of percent identity between two sequences may be accomplished using readily available software. Suitable software programs are available from various sources, both for online use and for download, and for alignment of both protein and nucleotide sequences. One suitable program is ClustalW (Thompson et al. (1994) *Nucleic Acids Res.* 11; 22(22): 4673-80), available from www.clustal.org, or alternatively e.g. from the European Bioinformatics Institute (www.ebi.ac.uk), which also provides various other protein and nucleotide informatics tools.

When specific anti-EGFR antibodies are mentioned herein, e.g. antibodies referred to as 992, 1024, 1030, 1254 and 1277, these antibody numbers generally refer to the anti-EGFR antibodies described in WO 2008/104183.

When specific anti-HER2 antibodies are mentioned herein, e.g. antibodies referred to as 4382, 4384, 4385 and 4518, these antibody numbers refer to the anti-HER2 antibodies described in WO 2011/107957 A1.

When specific anti-HER3 antibodies are mentioned herein, e.g. antibodies referred to as 4785, 5038, 5082 and 5096, these antibody numbers refer to the anti-HER3 antibodies with the DNA and amino acid sequences provided in the sequence listing.

Antibody Mixtures

In one embodiment, the invention relates to a recombinant antibody composition i.e. a composition, wherein at least one distinct anti-HER antibody molecule binds to an antigen of a first HER family receptor and at least one distinct anti-HER antibody molecule binds to an antigen of a second HER family receptor. In a preferred embodiment, the invention relates to a recombinant antibody composition i.e. a composition, wherein at least one distinct anti-HER antibody molecule binds to an antigen of a first HER family receptor, at least one distinct anti-HER antibody molecule binds to an antigen of a second HER family receptor and at least on distinct anti-HER antibody molecule binds to an antigen of a third HER family receptor. In a further preferred embodiment, the antibody composition comprises at least one distinct anti-HER antibody molecule capable of binding to an antigen of a first HER family receptor and at least two distinct anti-HER antibody molecules capable of binding to an antigen of a second HER family receptor. In a further preferred embodiment, the antibody composition comprises at least two distinct anti-HER antibody molecules capable of binding to an antigen of a first HER family receptor and at least two distinct anti-HER antibody molecules capable of binding to an antigen of a second HER family receptor. In a further preferred embodiment, the antibody composition comprises at least one distinct anti-HER antibody molecules capable of binding to an antigen of a first HER family receptor, at least one distinct anti-HER antibody molecules capable of binding to an antigen of a second HER family receptor and at least two distinct anti-HER antibody molecules binding to an antigen of a third HER family receptor. In a further preferred embodiment, the antibody composition comprises at least one distinct anti-HER antibody molecules capable of binding to an antigen of a first HER family receptor, at least two distinct anti-HER antibody molecules capable of binding to an antigen of a second HER family receptor and at least two distinct anti-HER antibody molecules binding to an antigen of a third HER family receptor. In a even further preferred embodiment, the antibody composition comprises at least two distinct anti-HER antibody molecules capable of binding to an antigen of a first HER family receptor, at least two distinct anti-HER antibody molecules capable of binding to an antigen of a second HER family receptor and at least two distinct anti-HER antibody molecules capable of binding to an antigen of a third HER family receptor.

The first and second HER family receptors are preferably EGFR and HER2, HER2 and EGFR, EGFR and HER3, HER3 and EGFR, HER2 and HER3, HER3 and HER2, respectively. In the embodiment where the antibody molecules bind to three different receptors of the HER family the first, second and third HER family receptors are preferably EGFR and HER2 and HER3, EGFR and HER3 and HER2, HER2 and EGFR and HER3, HER2 and HER3 and EGFR, HER3 and EGFR and HER2, HER3 and HER2 and EGFR, respectively.

The distinct anti-HER antibodies bind to non-overlapping epitopes on the receptors.

The non-overlapping nature of the antibodies is preferably determined using differently labelled antibodies in a FACS analysis with HER expressing cells or by using Surface Plasmon Resonance using HER antigen captured or conjugated to a flow cell surface. A composition binding non-overlapping epitopes can be used against a wider range of HER dependent cancer types as it may be less vulnerable to differences in HER conformation and less vulnerable to mutations compared to compositions of monoclonal antibodies targeting one or two epitopes. Furthermore, the antibody composition binding non-overlapping epitopes may provide superior efficacy compared to compositions targeting fewer epitopes. In particular, the antibody composition may provide superior efficacy with respect to terminal differentiation of cancer cells in vivo.

While it is preferred to include in an antibody composition of the invention at least two distinct anti-HER antibody molecules that bind to an antigen of a first HER family receptor and at least two distinct anti-HER antibody molecules that bind to an antigen of a second HER family receptor, antibody compositions capable of binding at least three different receptors of the HER family are more preferred. These preferred compositions are described in more detail below together with guidance relating to how to design antibody compositions of the invention.

The antibodies of the composition may be chimeric antibodies with non-human variable chains and human constant chains. The non-human variable chains may be from a mouse, rat, sheep, pig, chicken, non-human primate or other suitable animal. In order to obtain fully human antibodies the antibodies can be generated in a transgenic animal with human antibody genes. The antibodies may also be humanized antibodies as described above, where the non-human CDR sequences have been grafted into human framework sequences.

Preferably the human constant chain is of the IgG1 or IgG2 isotype. More preferably all antibodies in the composition have the same isotype for ease of manufacturing. However, it may in some cases be advantageous to include in the composition antibodies with different isotypes.

Preferably the antibody compositions of the invention comprise antibodies capable of binding to a HER family receptor selected from the group consisting of human EGFR, HER2 and HER3, mutated human EGFR, HER2 and HER3, and deletion variants of human EGFR, HER2 and HER3. Preferably the antibodies are capable of binding both human and non-human primate EGFR, HER2 and/or HER3, so that they can be tested in relevant toxicology studies prior to clinical experiments. Preferably, the non-human primate is a cynomolgus monkey (*Macaca fascicularis*).

Results obtained with cancer cell lines A431NS and MCF7 (Example 3) and have shown that combinations of anti-EGFR mixtures and anti-HER3 or anti-HER2 mixtures give rise to synergistic increases in inhibition of cancer cell growth and that a combination of mixtures against all three receptors is superior to individual mixtures and to combinations of mixtures against two receptors.

The combination of mixtures against all three receptors was compared to the marketed monoclonal antibodies cetuximab (anti-EGFR) and trastuzumab (anti-HER2) and a mixture of these two antibodies. The results show that a combination of antibody mixtures against the three receptors EGFR, HER2 and HER3 is superior to both cetuximab and trastuzumab and also to a mixture of these two antibodies in different cell lines.

Overall the results have shown that the optimal targeting of more than one of the HER family receptors is obtained by combining mixtures of antibodies against each receptor and that targeting three receptors is superior to targeting two receptors.

Results obtained with cell lines MCF7, HCC202, BT474, NCI-N87, MDA-MB-175, A431NS, HN5, H292, DU145 and MDA-MB-468 (Example 4) have also shown that the combination of the anti-EGFR mixture and the anti-HER2 mixture inhibits all the tested cell lines. Targeting only one of these receptors results in inhibition of the cell lines that are dependent on that particular receptor. Overall, these results show that a combination of mixtures of antibodies against EGFR and HER2 gives a much broader inhibitory profile and may thus ultimately be used to treat patients whose tumors are dependent on either of the receptors.

The results from the Western Blot investigation (Examples 5 and 7) show that mixtures of antibodies against a single receptor (EGFR, HER2 and HER3) induce degradation of their respective target and that a combination of antibody mixtures against each target is able to induce efficient degradation of all three receptors simultaneously.

Results obtained with cancer cell lines A431NS, H358, HC202, OE19, and H820 (Example 6) show that although the effect of the antibody mixtures and individual antibodies varies among the different cell lines, the antibody mixtures containing antibodies against each of the three receptors EGFR, HER2 and HER3 are generally efficacious at inhibiting cell growth and proliferation. The mixtures containing six antibodies, i.e. two antibodies against each of the three receptors, are in general the most efficacious across the different cell lines.

The results from Example 8 show that although the effect of the antibody mixtures and individual antibodies varies between the different cell lines, the antibody mixtures comprised of three, four or six antibodies against the three receptors EGFR, HER2 and HER3 are generally very efficacious at inhibiting cancer cell growth and proliferation.

The results from Example 9 demonstrate that the optimal targeting of more than one receptor in the HER family is obtained by combining mixtures of antibodies against each receptor, that targeting of three receptors is superior to targeting of two receptors, and that targeting of each receptor with a mixture of antibodies is superior to targeting of each receptor with a single antibody.

Finally, the results from the in vivo efficacy experiment (Example 10) shows that treating A431NS tumor xenografts with a combination of antibodies or antibody mixtures against EGFR+HER3 or EGFR+HER2+HER3 is more effective compared to targeting the tumors with monoclonal antibodies and antibody mixtures against the individual targets EGFR, HER2 and HER3, or combinations of monoclonal antibodies and antibody mixtures against EGFR+HER2 or HER2+HER3.

What is evident from these experiments is that combinations of antibodies provided by the present inventors display efficacy against a very wide range of cancer cell lines.

In a preferred embodiment, the antibody composition of the invention comprises at least two distinct anti-EGFR antibody molecules selected from the group consisting of antibodies capable of inhibiting the binding of and/or which bind the same epitope as an antibody having the CDRs of antibodies: 992, 1024, 1030, 1254, 1277 and 1565.

In another preferred embodiment, the antibody composition comprises at least two distinct anti-EGFR antibody molecules selected from the group of combinations consisting of antibodies with the CDRs of antibodies: 992+1030, 992+1024, 1024+1030, 1030+1254, 1030+1277, 1030+1565, 1254+1277, 1254+1565, and 1277+1565. In a particular embodiment, the anti-EGFR antibodies have the CDRs of antibodies 1277+1565 or 1254+1565.

In another preferred embodiment, the antibody composition comprises least two distinct anti-HER2 antibody molecules selected from the group consisting of antibodies capable of inhibiting the binding of and/or which bind the same epitope as an antibody having the CDRs of antibodies: 4382, 4384 4385, 4517 and 4518.

In another preferred embodiment, the antibody composition comprises at least two distinct anti-HER2 antibody molecules selected from the group of combinations consisting of antibodies with the CDRs of antibodies: 4382+4384, 4382+4385, 4382+4517, 4382+4518, 4384+4385, 4384+4517, 4384+4518, 4517+4518, and 4385+4518. In a particular embodiment, the anti-HER2 antibodies have the CDRs of antibodies 4384+4517 or 4385+4518.

In another preferred embodiment, the antibody composition comprises at least two distinct anti-HER3 antibody molecules selected from the group consisting of antibodies capable of inhibiting the binding of and/or which bind the same epitope as an antibody having the CDRs of antibodies: 4785, 5038, 5082, and 5096.

In another preferred embodiment, the antibody composition comprises at least two distinct anti-HER3 antibody molecules selected from the group of combinations consisting of antibodies with the CDRs of antibodies: 4785+5038, 4785+5082, 4785+5096, 5038+5082, 5038+5096, and 5082+5096. In a particular embodiment, the anti-HER3 antibodies have the CDRs of antibodies 5038+5082.

In another preferred embodiment, the antibody composition is selected from the group of combinations consisting of antibodies with the CDRs of antibodies: 992+1024+4785+5082, 992+1024+4382+4385+4518, 992+1024+4382+4385+4518+4785+5082, 4382+4385+4518+4785+5082, 1565+4517+5082, 1277+4517+5082, 1277+4384+5038, 1277+4384+5082, 1277+1565+5038+5082, 1277+1565+4384+4517, 4384+4517+5038+5082, 1277+4384+4517+5082, 1277+4384+4517+5038, 1277+1565+4384+4517+5038+5082, and 1277+1565+4385+4518+5038+5082.

A preferred embodiment of the invention includes a recombinant antibody composition comprising antibody molecules as defined wherein the heavy chain variable region sequence and light chain variable region sequence each having at least 90% sequence identity, preferably at least 95% sequence identity, such as at least 96%, at least 97%, at least 98% or at least 99% sequence identity, with the heavy chain variable region and light chain variable region sequences, respectively, of any one of these antibodies, and which competes for binding with said antibody.

In a particular embodiment, the antibody composition of the invention comprises at least one anti-EGFR antibody with CDRs from, or which is capable of inhibiting the binding of and/or which binds the same epitope, as 1254, 1277 or 1565; at least one anti-HER2 antibody with CDRs from, or which is capable of inhibiting the binding of and/or which binds the same epitope as, 4384, 4385, 4517 or 4518; and at least one anti-HER3 antibody with CDRs from, or which is capable of inhibiting the binding of and/or which binds the same epitope as, 5038 or 5082.

In a preferred embodiment, the antibody composition comprises two antibodies directed against each of EGFR, HER2 and HER3, wherein the anti-EGFR antibodies have the CDRs from, or are capable of inhibiting the binding of and/or bind the same epitope as, 1277+1565 or 1254+1565; the anti-HER2 antibodies have the CDRs from, or are capable of inhibiting the binding of and/or bind the same epitope as, 4384+4517 or 4385+4518; and the anti-HER3 antibodies have the CDRs from, or are capable of inhibiting the binding of and/or bind the same epitope as, 5038+5082.

In a further preferred embodiment, the antibody composition comprises antibodies with the CDRs of antibodies 1277+1565+4384+4517+5038+5082, or antibodies that are capable of inhibiting the binding of and/or bind the same epitope as said antibodies.

In a further preferred embodiment, the antibody composition comprises antibodies with the CDRs of antibodies 1277+1565+4385+4518+5038+5082, or antibodies that are capable of inhibiting the binding of and/or bind the same epitope as said antibodies.

Table 1 below shows the sequence ID numbers, as set forth in the appended sequence listing, for the DNA and amino acid sequences of the heavy chain variable regions (VH) and the light chains (LC) of antibodies 992, 1024, 1030, 1254, 1277, 1565, 4382, 4384, 4385, 4517, 4518, 4785, 5038, 5082, and 5096.

TABLE 1

Sequence ID numbers for the DNA and amino acid sequences of the heavy chain variable regions and light chains of selected anti-HER antibodies

| Antibody Number | VH DNA seq. | VH protein seq. | LC DNA seq. | LC protein seq. |
|---|---|---|---|---|
| 992 | 1 | 2 | 3 | 4 |
| 1024 | 5 | 6 | 7 | 8 |
| 1030 | 9 | 10 | 11 | 12 |
| 1254 | 13 | 14 | 15 | 16 |
| 1277 | 17 | 18 | 19 | 20 |
| 1565 | 21 | 22 | 23 | 24 |
| 4382 | 25 | 26 | 27 | 28 |
| 4384 | 29 | 30 | 31 | 32 |
| 4385 | 33 | 34 | 35 | 36 |
| 4517 | 37 | 38 | 39 | 40 |
| 4518 | 41 | 42 | 43 | 44 |
| 4785 | 45 | 46 | 47 | 48 |
| 5038 | 49 | 50 | 51 | 52 |
| 5082 | 53 | 54 | 55 | 56 |
| 5096 | 57 | 58 | 59 | 60 |

Tables 2 and 3 below show the CDR1, CDR2 and CDR3 amino acid sequences of the heavy chain (Table 2) and the light chain (Table 3) of various anti-HER antibodies according to the invention. The amino acid sequences of the heavy chain variable region and the light chain, including the light chain variable region, of these antibodies, as well as the encoding DNA sequences (optimized for expression in CHO cells) are provided in the appended sequence listing. See Table 1 above for an overview of the SEQ ID numbers for these sequences.

TABLE 2

Heavy chain CDR1, CDR2 and CDR3 sequences of selected anti-HER antibodies

| Antibody Number | H CDR1 | H CDR2 | H CDR3 | SEQ IN NOs (CDR1/2/3) |
|---|---|---|---|---|
| 92 | GYTFTSYW | IYPGSRST | CTRNGDYYVSSGDAMDYW | 61-63 |
| 1024 | GYTFTSHW | INPSSGRN | CVRYYGYDEAMDYW | 64-66 |
| 1030 | GFTFSSYA | ISGVGST | CARGSDGYFYAMDYW | 67-69 |
| 1254 | GFAYSTYD | ISSGGDAA | CARSRYGNYGDAMDYW | 70-72 |
| 1277 | GFAFSYSD | MSSAGDVT | CVRHRDVAMDYW | 73-75 |
| 1565 | GYTFTSYW | INPSNGGT | CARDGGLYDGYYFDFW | 76-78 |
| 4382 | GYTFTDYY | INPNNGGT | CVPGGLRSYFDYW | 79-81 |

TABLE 2-continued

Heavy chain CDR1, CDR2 and CDR3 sequences of selected anti-HER antibodies

| Antibody Number | H CDR1 | H CDR2 | H CDR3 | SEQ IN NOs (CDR1/2/3) |
|---|---|---|---|---|
| 4384 | GYTFTSHW | INPSNGGT | CARAYYDFSWFVYW | 82-84 |
| 4385 | GYTFTGYW | ILPGSGST | ARWGDGSFAY | 85-87 |
| 4517 | GFTFSSYG | ISGGGSYT | CARKGNYGNYGKLAYW | 88-90 |
| 4518 | GFNIKDIF | IDPANDNP | CAGGPAYFDYW | 91-93 |
| 4785 | GYSFTSYY | IYPGSGHT | CARPPYYSNYADVW | 94-96 |
| 5038 | GYSITSGFY | ISYDGSN | CARGGGYYGNLFDYW | 97-99 |
| 5082 | GYSITSAYY | IGYDGRN | CSREGDYGYSDYW | 100-102 |
| 5096 | GYTFTSYL | INPYNDGA | CAREGDYVRYYGMDYW | 103-105 |

TABLE 3

Light chain CDR1, CDR2 and CDR3 sequences of selected anti-HER antibodies

| Antibody Number | L CDR1 | L CDR2 | L CDR3 | SEQ ID NOs (CDR1/2/3) |
|---|---|---|---|---|
| 992 | QDIGNY | YTS | CQHYNTVPPTF | 106-108 |
| 1024 | KSLLHSNGITY | QMS | CAQNLELPYTF | 109-111 |
| 1030 | KSVSTSGYSF | LAS | CQHSREFPLTF | 112-114 |
| 1254 | QSLVHSNGNTY | KVS | CSQNTHVYTF | 115-117 |
| 1277 | QSLVHSNGNTY | KVS | CSQSTHVPTF | 118-120 |
| 1565 | QDVDTA | WAS | CQQYSSYPLTF | 121-123 |
| 4382 | QDVSAA | WAS | CQQHYTTPPTF | 124-126 |
| 4384 | QDISNY | YIS | CQQGNTLPLTF | 127-129 |
| 4385 | QNVGTA | STS | CQQYRSYPFTF | 130-132 |
| 4517 | ENIYSN | AAT | CQHFWGTPWTF | 133-135 |
| 4518 | QDVIAA | WAS | CQQHYSTPWTF | 136-138 |
| 4785 | QSLLNSGNQKNY | WAS | CQSDYSYPYTF | 139-141 |
| 5038 | QDISNY | HTS | CQQGITLPWTF | 142-144 |
| 5082 | QDINNY | YTS | CQQSETLPWTF | 145-147 |
| 5096 | QSVLYISNERNY | WAS | CHQHLSSYTF | 148-150 |

Furthermore, in order to be able to perform a toxicology study in a non-human primate, it is preferable that all antibodies in the composition bind to human as well as to at least one further primate ErbB family receptor, such as ErbB from chimpanzee (Pan troglodytes), Rhesus monkey (Macaca mulatta), cynomolgus monkey (Macaca fascicularis) or other monkeys. Cynomolgus monkey is a relatively small animal, and very well suited for toxicology studies. Therefore, the further primate ErbB family receptor is preferably cynomolgus ErbB. Preferably the antibodies bind with approximately the same affinity to human and non-human primate ErbB.

A further preferred feature of the antibodies of the compositions is protein homogeneity, so that the antibodies can be purified easily. For the individual antibody members, an ion exchange chromatography profile with one distinct peak is preferred for ease of characterisation. A clear ion exchange chromatography profile is also preferred for ease of characterisation of the final antibody composition. It is also preferable when combining the antibodies that they can be distinguished using ion exchange chromatography, so that the composition with all the antibodies can be characterised in one run.

The antibodies may be of any origin such as human, murine, rabbit, chicken, pig, lama, sheep, and camel. The antibodies may also be chimeric as described in the examples or may be humanised, superhumanised or reshaped versions thereof using well-known methods described in the art.

The antibodies may be formulated in one container for administration. However, they may be manufactured, purified and characterised individually and be provided in separate containers as a kit of parts, with one antibody in each container. As such they may be administered simultaneously, successively or separately.

Another aspect of the invention relates to nucleic acid molecules comprising a nucleotide sequence that encodes an antibody of the invention, i.e. an antibody selected from the group consisting of antibodies 992, 1024, 1030, 1254, 1277, 1565, 4382, 4384, 4385, 4517, 4518, 4785, 5038, 5082, and 5096, or a humanized variant thereof; or encoding a heavy and/or light chain variable region sequence of such an antibody, or a heavy and/or light chain sequence having at least having at least 90% or 95% sequence identity with the reference sequence, such as at least 96%, 97%, 98% or 99% sequence identity with such a heavy and/or light chain variable region sequence.

A further aspect of the invention relates to an expression vector comprising a nucleic acid molecule as defined above. As noted above, expression vectors for use in the context of the present invention may be of any suitable type known in the art, e.g. a plasmid or a viral vector.

A still further aspect of the invention relates to a host cell comprising a nucleic acid molecule as defined above, wherein said host cell is capable of expressing an antibody encoded by said nucleic acid molecule.

Production of Antibodies of the Invention and Antibody Compositions

An additional aspect of the invention relates to methods for producing recombinant antibodies targeting the epidermal growth factor receptor (HER) family and compositions comprising the antibodies of the invention. One embodiment of this aspect of the invention relates to a method for producing the antibodies as defined herein, comprising providing a host cell as defined above capable of expressing an antibody, cultivating said host cell under conditions suitable for expression of the antibody, and isolating the resulting antibody.

In another embodiment, the invention relates to method for producing a recombinant antibody composition comprising recombinant anti-HER antibodies as described herein, the method comprising providing a number of cells, wherein each cell is capable of expressing a recombinant anti-HER antibody, cultivating cells under conditions suitable for expression of the antibodies of the composition, and isolating the resulting antibodies.

An antibody or antibody composition of the present invention may be produced by methods generally known in the art for production of recombinant monoclonal or polyclonal antibodies. Thus, in the case of production of a single antibody of the invention, any method known in the art for production of recombinant monoclonal antibodies may be used. For production of an antibody composition of the invention, the individual antibodies may be produced separately, i.e. each antibody being produced in a separate bioreactor, or the individual antibodies may be produced together in single bioreactor. If the antibody composition is produced in more than one bioreactor, the purified anti-HER antibody composition can be obtained by pooling the antibodies obtained from individually purified supernatants from each bioreactor. Various approaches for production of a polyclonal antibody composition in multiple bioreactors, where the cell lines or antibody preparations are combined at a later point upstream or prior to or during downstream processing, are described in WO 2009/129814 (incorporated by reference).

In the case of production individual antibodies in a single bioreactor, this may be performed e.g. as described in WO 2004/061104 or WO 2008/145133 (both of which are incorporated herein by reference). The method described in WO 2004/061104 is based on site-specific integration of the antibody coding sequence into the genome of the individual host cells, ensuring that the $V_H$ and $V_L$ protein chains are maintained in their original pairing during production. Furthermore, the site-specific integration minimises position effects, and therefore the growth and expression properties of the individual cells in the polyclonal cell line are expected to be very similar. Generally, the method involves the following: i) a host cell with one or more recombinase recognition sites; ii) an expression vector with at least one recombinase recognition site compatible with that of the host cell; iii) generation of a collection of expression vectors by transferring the selected $V_H$ and $V_L$ coding pairs from the screening vector to an expression vector such that a full-length antibody or antibody fragment can be expressed from the vector (such a transfer may not be necessary if the screening vector is identical to the expression vector); iv) transfection of the host cell with the collection of expression vectors and a vector coding for a recombinase capable of combining the recombinase recognition sites in the genome of the host cell with that in the vector; v) obtaining/generating a polyclonal cell line from the transfected host cell and vi) expressing and collecting the antibody composition from the polyclonal cell line.

WO 2008/145133 describes an alternative approach to production of antibodies in a single bioreactor. This method involves generation of a polyclonal cell line capable of expressing a polyclonal antibody or other polyclonal protein comprising two or more distinct members by a) providing a set of expression vectors, wherein each of said vectors comprises at least one copy of a distinct nucleic acid encoding a distinct member of the polyclonal protein, separately transfecting host cells with each of the expression vectors under conditions avoiding site-specific integration of the expression vectors into the genome of the cells, thereby obtaining two or more compositions of cells, each composition expressing one distinct member of the polyclonal protein, and c) mixing the at least two compositions of cells to obtain a polyclonal cell line. The methods of WO 2004/061104 and WO 2008/145133 both have the advantage of allowing all of the members constituting the recombinant polyclonal antibody to be produced in a single bioreactor and to be purified in a single process, thereby avoiding the need for separate production and purification processes for each antibody, while at the same time resulting in a surprisingly uniform production of the different antibodies. The method of WO 2008/145133 has the further advantage of providing an increased yield, since each production cell can carry multiple copies of the polynucleotide encoding a particular antibody.

The antibodies of the invention may be produced in various types of cells, including mammalian cells as well as non-mammalian eukaryotic or prokaryotic cells, such as plant cells, insect cells, yeast cells, fungi, *E. coli* etc. However, the antibodies are preferably produced in mammalian cells, for example CHO cells, COS cells, BHK cells, myeloma cells (e.g. Sp2/0 or NS0 cells), fibroblasts such as NIH 3T3, or immortalized human cells such as HeLa cells, HEK 293 cells or PER.C6 cells.

Methods for transfecting a nucleic acid sequence into a host cell are well-known in the art (see, e.g., Sambrook et al., Molecular Cloning: A Laboratory Manual, Cold Spring Harbor Laboratory Press, 3rd Edition, 2001). For site-specific integration e.g. as described in WO 2004/061104, a suitable host cell will comprise one or more recombinase recognition sites in its genome. In this case, a suitable expression vector comprises a recombination recognition site matching the recombinase recognition site(s) of the host cell. Further details regarding e.g. transfer of selected VH and VL coding pairs from a screening vector using the site-specific integration approach may be found in WO 2004/061104.

A recombinant antibody composition of the present invention may be manufactured in a single bioreactor by culturing one ampoule from a polyclonal working cell bank (pWCB) in an appropriate medium for a period of time to allow for a sufficient level of antibody expression while maintaining substantial uniformity in the relative expression levels of the individual antibodies expressed by the polyclonal cell line. A production time of between approximately 15 and 50 days will normally be suitable. Culturing methods known in the art such as fed batch or perfusion culturing may be used. The culture medium is preferably a serum-free medium, more preferably a serum-free and protein free medium, e.g. a chemically defined medium. Such culture media are typically designed for growth of the particular cell type being used for production, and numerous suitable media formulations are commercially available.

The recombinant antibody composition is obtained from the culture medium and purified by conventional purification techniques. These may include, for example, affinity chromatography combined with subsequent purification steps such as ion-exchange chromatography, hydrophobic interaction chromatography and gel filtration, as these purification techniques have frequently been used for the purification of recombinant antibodies. When two or more antibodies are produced by a polyclonal cell line in a single bioreactor, the presence of all the individual members in the polyclonal antibody composition is typically assessed subsequent to purification, for example by ion-exchange chromatography. Characterization of a polyclonal antibody composition may be performed e.g. as described in WO 2006/007853 and WO 2009/065414 (incorporated herein by reference).

Therapeutic Compositions

Another aspect of the invention is a pharmaceutical composition comprising as an active ingredient an antibody composition of the invention, or a recombinant Fab or another recombinant antibody fragment composition. Such compositions are intended for amelioration, prevention and/or treatment of cancer. The pharmaceutical composition may be administered to a human or to a domestic animal or pet, but will typically be administered to humans.

The ratio between the individual antibodies in a therapeutic composition of the invention, or, in the case of individual antibodies of the invention being administered simultaneously, sequentially or separately, will often be such that the antibodies are administered in equal amounts, but this needs not necessarily be the case. Thus, a composition of the invention comprising two anti-HER antibodies will often contain them in a 1:1 ratio, and a composition comprising three anti-HER antibodies will often contain them in a 1:1:1 ratio. Depending on the characteristics of the individual antibodies, however, it may be desirable to use non-equal amounts of the different antibodies. Suitable ratios for the different anti-HER antibodies in compositions of the invention may be determined as described in WO 2010/040356 (incorporated herein by reference), which describes methods for identifying and selecting the optimal stoichiometric ratio between chemical entities in a combinatorial drug product, e.g. a polyclonal antibody composition, to obtain a combinatorial drug with optimal potency and efficacy.

In addition to the antibody composition of the invention or fragments thereof, the pharmaceutical composition will further comprise at least one pharmaceutically acceptable diluent, carrier or excipient. These may for example include preservatives, stabilizers, surfactants/wetting agents, emulsifying agents, solubilizers, salts for regulating the osmotic pressure and/or buffers. Solutions or suspensions may further comprise viscosity-increasing substances, such as sodium carboxymethylcellulose, carboxymethylcellulose, dextran, polyvinylpyrrolidone or gelatin. A suitable pH value for the pharmaceutical composition will generally be in the range of about 5.5 to 8.5, such as about 6 to 8, e.g. about 7, maintained where appropriate by use of a buffer.

Conventional pharmaceutical practice may be employed to provide suitable formulations or compositions to administer to e.g. cancer patients. The administration will typically be therapeutic, meaning that it is administered after a cancer condition has been diagnosed. Any appropriate route of administration may be employed, for example parenteral, intravenous, intra-arterial, subcutaneous, intramuscular, intraperitoneal, intranasal, aerosol, suppository or oral administration. Pharmaceutical compositions of the invention will typically be administered in the form of liquid solutions or suspensions, more typically aqueous solutions or suspensions, in particular isotonic aqueous solutions or suspensions.

The pharmaceutical compositions of the invention are prepared in a manner known per se, for example, by means of conventional dissolving, lyophilizing, mixing, granulating or confectioning processes. The pharmaceutical compositions may be formulated according to conventional pharmaceutical practice (see, for example, Remington: The Science and Practice of Pharmacy (21st edition), ed. A. R. Gennaro, 2005, Lippincott Williams & Wilkins, Philadelphia, Pa., USA; and Encyclopedia of Pharmaceutical Technology, ed. J. Swarbrick, $3^{rd}$ edition, 2006, Informa Healthcare, New York, N.Y., USA).

As an alternative to a liquid formulation, the compositions of the invention may be prepared in lyophilized form comprising the at least one antibody alone or together with a carrier, for example mannitol, in which case the composition is reconstituted with a liquid such as sterile water prior to use.

The pharmaceutical compositions comprise from approximately 1% to approximately 95%, preferably from approximately 20% to approximately 90%, active ingredient. Pharmaceutical compositions according to the invention may e.g. be produced in unit dose form, such as in the form of ampoules, vials, suppositories, tablets or capsules. The formulations can be administered to human individuals in therapeutically or prophylactically effective amounts (e.g., amounts which prevent, eliminate, or reduce a pathological condition) to provide therapy for a cancerous disease or other condition. The preferred dosage of therapeutic agent to be administered is likely to depend on such variables as the severity of the cancer, the overall health status of the particular patient, the formulation of the compound excipients, and its route of administration.

Therapeutic Uses of Antibodies Compositions According to the Invention

The pharmaceutical compositions according to the present invention may be used for the treatment or amelioration of a disease in a mammal, in particular treatment of cancer in humans. One embodiment of the invention is a method of preventing, treating or ameliorating one or more symptoms associated with cancer in a human or other mammal, comprising administering an effective amount of the pharmaceutical antibody composition of the present invention to said mammal.

A particular embodiment relates to a method for treating a human patient with a disorder characterized by overexpression or dependency of any of the HER family members, in particular cancer, the method comprising administering to said patient a recombinant antibody composition as defined herein.

In a further embodiment, the invention relates to a method for treating cancer in a human or other mammal having acquired resistance to the treatment with antibodies and/or TKIs, the method comprising administering to said mammal an effective amount of an antibody composition as defined herein.

Based upon a number of factors, the following tumor types in particular may be indicated for treatment with an antibody composition of the invention: breast, ovarian, gastric, colon, rectum, prostate, bladder, pancreas, melanoma, head and neck, and non-small cell lung cancer. Antibody compositions of the invention are contemplated to be particularly applicable to treatment of cancers that overexpress EGFR or HER2, for example certain epithelial cancers such as many breast cancers, ovarian cancers and gastric (stomach) cancers.

In connection with each of these indications, two main clinical pathways are contemplated, namely 1) adjunctive therapy in connection with at least one additional therapeutic treatment or 2) as a monotherapy. These two options are briefly discussed below.

1) Adjunctive therapy: In adjunctive therapy, also known as combination therapy, patients will be treated with antibodies of the present invention in combination with at least one additional therapeutic treatment, typically a chemotherapeutic or antineoplastic agent and/or radiation therapy. Alternatively or additionally, the composition of the invention may also be used in combination with a different anti-cancer antibody, e.g. an antibody targeting VEGF. The primary cancer targets listed above may thus be treated by administration of an antibody or composition of the invention in addition to standard first line and second line therapy. Protocol designs will address effectiveness as assessed e.g. by reduction in tumor mass as well as the ability to reduce usual doses of standard chemotherapy. Such dosage reductions may allow additional and/or prolonged therapy by reducing dose-related toxicity of the chemotherapeutic agent.

By combining the antibody compositions of the invention with agents known to induce terminal differentiation of cancer cells, the effect may be improved further. Such compounds may, for example, be selected from the group consisting of retinoic acid, trans-retinoic acids, cis-retinoic acids, phenylbutyrate, nerve growth factor, dimethyl sulfoxide, active form vitamin D3, peroxisome proliferator-activated receptor gamma, 12-O-tetradecanoylphorbol 13-acetate, hexamethylene-bis-acetamide, transforming growth factor-beta, butyric acid, cyclic AMP, and vesnarinone. Preferably, the compound is selected from the group consisting of retinoic acid, phenylbutyrate, all-trans-retinoic acid, and active form vitamin D.

Pharmaceutical articles comprising an antibody composition of the invention and at least one chemotherapeutic or antineoplastic compound may be used as a combination treatment for the simultaneous, separate or successive administration in cancer therapy. The chemotherapeutic compound may by any chemotherapeutic agent suitable for treatment of the particular cancer in question, for example an agent selected from the group consisting of alkylating agents, for example platinum derivatives such as cisplatin, carboplatin and/or oxaliplatin; plant alkoids, for example paclitaxel, docetaxel and/or irinotecan; antitumor antibiotics, for example doxorubicin (adriamycin), daunorubicin, epirubicin, idarubicin mitoxantrone, dactinomycin, bleomycin, actinomycin, luteomycin, and/or mitomycin; topoisomerase inhibitors such as topotecan; and/or antimetabolites, for example fluorouracil and/or other fluoropyrimidines.

It is also contemplated that antibody composition of the invention may be used in adjunctive therapy in connection with tyrosine kinase inhibitors (TKIs). These are synthetic, mainly quinazoline-derived, low molecular weight molecules that interact with the intracellular tyrosine kinase domain of receptors and inhibiting ligand-induced receptor phosphorylation by competing for the intracellular Mg-ATP binding site. Several tyrosine kinase inhibitors that block HER2 kinase are currently in clinical development. Some of these also target EGFR or other EGFR family receptors. For a review of these TKIs see Spector et al. (2007) *Breast Cancer Res.* 9(2): 205. Pharmaceutical articles comprising an antibody composition of the invention and at least one TKI targeting HER2 may thus also be used as a combination treatment for the simultaneous, separate or successive administration in cancer therapy.

In other embodiments, the antibody compositions of the present invention may be used in combination with other antibody therapeutics. Examples of these include e.g. antibodies against EGFR (Erbitux® or Vectibix®) or VEGF (Avastin®). In yet other embodiments, the antibody compositions of the present invention may be used in combination with an agent known to stimulate cells of the immune system, such combination treatment leading to enhanced immune-mediated enhancement of the efficacy of the antibody compositions of the invention. Examples of such immune-stimulating agents include recombinant interleukins (e.g. IL-21 and IL-2).

2) Monotherapy: In connection with the use of the antibody composition in accordance with the present invention in monotherapy of tumors, the antibody composition may be administered to patients without concurrent use of a chemotherapeutic or antineoplastic agent, i.e. as a stand-alone therapy.

Immunoconjugates

Another option for therapeutic use of the compositions of the invention is in the form of immunoconjugates, i.e. antibodies conjugated to one or more anti-cancer agents. In particular in the case of compositions of the invention that bind distinct epitopes, it is contemplated that this may generate a cross-linked antibody-receptor lattice on the cell surface, thereby potentially resulting in an increased level of receptor internalization as compared to the use of a single monoclonal antibody. Conjugation of one or more of the individual antibodies of such a composition to one or more anti-cancer agents therefore has the potential to specifically and effectively deliver the conjugated anti-cancer agents to the interior of tumor cells, thereby augmenting the effect of the antibody composition of the invention to provide an improved tumor cell-killing activity.

Various types of anti-cancer agents may be conjugated to the antibodies of the invention, including cytotoxic agents (including conventional chemotherapy agents and other small molecule anti-cancer drugs), cytokines (in which case the conjugate may be termed an "immunocytokine"), toxins (in which case the conjugate may be termed an "immunotoxin") and radionuclides, and a few immunoconjugates have already been approved for clinical use. These include Zevalin® (a murine anti-CD20 antibody conjugated to $^{90}$Y), Bexxar® (a murine anti-CD20 antibody conjugated to $^{131}$I) and Mylotarg® (a humanized anti-CD33 antibody conjugated to calicheamicin). Other immunoconjugates that have been tested in clinical trials include antibodies conjugated to e.g. doxorubicin or a maytansinoid compound. Immunotoxins that have been tested in clinical trials include several antibodies conjugated to a truncated *Pseudomonas* exotoxin A. An immunocytokine comprising a humanized EpCAM antibody conjugated to IL-2 has also been tested.

In the case of antibodies of the invention conjugated to cytotoxic agents, these may e.g. belong to any of the major classes of chemotherapy drugs, including alkylating agents (e.g. carboplatin, cisplatin, oxaliplatin), antimetabolites (e.g. methotrexate, capecitabine, gemcitabine), anthracyclines (e.g. bleomycin, doxorubicin, mitomycin-C) and plant alkaloids (e.g. taxanes such as docetaxel and paclitaxel, and *vinca* alkaloids such as vinblastine, vincristine and vinorelbine). Since the use of immunoconjugates specifically directs the anti-cancer agent to the tumors, and in particular to the interior of the tumor cells subsequent to internalization, immunoconjugates based on the antibodies of the invention may advantageously be based on highly cytotoxic agents such as calicheamicin or maytansine derivatives, or on toxins such as bacterial toxins (e.g. *Pseudomonas* exotoxin A, diphtheria toxin) or plant toxins (e.g. ricin).

The conjugated anti-cancer agent in an immunoconjugate is generally linked to the antibody by means of a labile linker that is relatively stable in serum but which allows release of the agent when the immunoconjugate is internalized into the target cell. Suitable linkers include, for example, chemical linkers that are stable at neutral pH in serum but are subjected to acid hydrolysis in the mildly acidic conditions within the lysosomes subsequent to internalization, disulfide linkers that are cleaved by intracellular thiols, and peptide linkers that are stable in serum but which are subjected to enzymatic cleavage in intracellular compartments.

Various conjugation arrangements can be envisioned in compositions containing two or more antibodies of the invention. For example, with two antibodies it would be possible to conjugate the antibodies to two or more different anti-cancer drugs or to conjugate one antibody to a prodrug which is activated by an agent such as an enzyme conjugated to the other antibody. The general concept of antibody-directed enzyme prodrug therapy (ADEPT) has been described for monoclonal antibodies, where a prodrug is activated by an enzyme targeted to the tumor by a mAB-enzyme conjugate, but the present invention may provide an opportunity for tailoring this approach to particular conditions. It may thus be possible to specifically increase tumor cell killing while sparing or reducing damage to normal tissues.

For further information on anti-cancer immunoconjugates, see Wu et al. (2005) *Nature Biotechnology* 23(9): 1137-1146; Schrama et al. (2006) *Nature Reviews/Drug Discovery* 5:147-159; and Rohrer (2009) *chimica oggi/Chemistry Today* 27(5):56-60.

Dose and Route of Administration

The antibody compositions of the invention will be administered in an effective amount for treatment of the condition in question, i.e. at dosages and for periods of time necessary to achieve a desired result. A therapeutically effective amount may vary according to factors such as the particular condition being treated, the age, sex and weight of the patient, and whether the antibodies are being administered as a stand-alone treatment or in combination with one or more additional anti-cancer treatments.

An effective amount for tumor therapy may be measured by its ability to stabilize disease progression and/or ameliorate symptoms in a patient, and preferably to reverse disease progression, e.g. by reducing tumor size. The ability of an antibody or composition of the invention to inhibit cancer may be evaluated by in vitro assays, e.g. as described in the examples, as well as in suitable animal models that are predictive of the efficacy in human tumors. Suitable dosage regimens will be selected in order to provide an optimum therapeutic response in each particular situation, for example, administered as a single bolus or as a continuous infusion, and with possible adjustment of the dosage as indicated by the exigencies of each case.

While specific dosing for antibodies in accordance with the invention has not yet been determined, certain dosing considerations can be determined through comparison with a similar product (e.g. a monoclonal antibody directed against HER2 or EGFR) that has been approved for therapeutic use. It is thus contemplated that an appropriate dosage of an antibody composition of the invention will be similar to the recommended dosage for the anti-HER2 monoclonal antibody trastuzumab (Herceptin®) or the anti-EGFR monoclonal antibody panitumumab (Vectibix®). Depending on the particular condition, Herceptin® is administered (by way of infusion) for treatment of breast cancer at either an initial dose of 4 mg/kg and subsequent weekly doses of 2 mg/kg, or an initial dose of 8 mg/kg and subsequent doses of 6 mg/kg every three weeks, while Vectibix® is administered at a dose of 6 mg/kg every 14 days.

It is contemplated that a suitable dose of an antibody composition of the invention will be in the range of 0.1-100 mg/kg, such as about 0.5-50 mg/kg, e.g. about 1-20 mg/kg. The antibody composition may for example be administered in a dosage of at least 0.25 mg/kg, e.g. at least 0.5 mg/kg, such as at least 1 mg/kg, e.g. at least 1.5 mg/kg, such as at least 2 mg/kg, e.g. at least 3 mg/kg, such as at least 4 mg/kg, e.g. at least 5 mg/kg; and e.g. up to at most 50 mg/kg, such as up to at the most 30 mg/kg, e.g. up to at the most 20 mg/kg, such as up to at the most 15 mg/kg. Administration will normally be repeated at suitable intervals, e.g. once every week, once every two weeks, once every three weeks, or once every four weeks, and for as long as deemed appropriate by the responsible doctor, who may optionally increase or decrease the dosage as necessary.

Three distinct delivery approaches are contemplated for delivery of the antibodies of the invention. Conventional intravenous delivery will presumably be the standard delivery technique for the majority of tumors. However, in connection with tumors in the peritoneal cavity, such as tumors of the ovaries, biliary duct, other ducts, and the like, intraperitoneal administration may prove favourable for obtaining high dose of antibody at the tumor and to minimize antibody clearance. Similarly, certain solid tumors possess vasculature that is appropriate for regional perfusion. Regional perfusion may allow the obtainment of a high dose of the antibody at the site of a tumor and minimise short term clearance of the antibody.

As with any protein or antibody infusion-based therapeutic product, safety concerns are related primarily to (i) cytokine release syndrome, i.e. hypotension, fever, shaking, chills, (ii) the development of an immunogenic response to the protein (i.e. development of human antibodies by the patient to the recombinant antibody product), and (iii) toxicity to normal cells that express the HER family receptors, e.g. many epithelial cells. Standard tests and follow-up procedures are utilised to monitor any such safety concerns.

All patent and non-patent references cited in the present application are hereby incorporated by reference in their entirety.

The invention will be further described in the following non-limiting examples.

EXAMPLES

The antibodies targeting EGFR and HER2 used in the following examples have all been identified in accordance with the methods described in WO 2008/104183 A2 and WO 2011/107957 A1, which are hereby incorporated by reference. The monoclonal antibody used as the control mAb in the examples is Synagis (Palivizumab). In all the Examples, the concentration on the x-axis is the total antibody concentration, i.e., in mixtures of two antibodies, each individual antibody comprises ½ of the total; in mixtures of three antibodies, each individual antibody comprises ⅓ of the total, and so forth.

Example 1

Cloning of Anti-HER3 Antibodies

Immunization

Three female mice, one BALB/cJ, one C57BL/6 mice and one C3H (8-10 weeks old), were used for the immunizations. The mice were immunized with commercially available HER3 protein (R&D Systems cat. #348-RB). For the first four immunizations, HER3 protein was diluted in PBS and mixed 1:1 (v/v) with Freund's adjuvant. The fifth and final immunization was given without adjuvant with the HER3 protein in PBS.

Adjuvant is used to enhance and modulate the immune response. In the first immunization Complete Freund's adjuvant (CFA) was used, whereas Incomplete Freund's adjuvant (IFA) was used for the second, third and fourth immunization. IFA is an oil-in-water emulsion composed of mineral oils, and CFA is IFA containing heat-killed, dried *Mycobacterium* species. Both adjuvants have a depot effect. The *mycobacterium* in CFA results in a strong activation of the immune system which leads to long-term persistence of the immune response. Only stable emulsions were administered to mice.

Ten μg recombinant HER3 protein was used for each immunization. In total, the mice received five injections. All mice were injected subcutaneously (s.c.) with 200 μl antigen-adjuvant emulsion the first four injections and intraperitoneally (i.p.) with 100 μl antigen in PBS for the fifth injection. A summary of the immunizations, adjuvants, injection routes etc. is found in Table 4.

The mice were sacrificed by cervical dislocation, and the spleens and inguinal lymph nodes were harvested. Single cell suspensions were prepared by macerating through a 70 μm cell strainer (Falcon, BD Biosciences, Cat. No. 352350). Cells from the three mice were pooled, re-suspended in cold RPMI-1640 with 10% FBS and spun down.

TABLE 4

Immunization summary.

| Day | Immunization | Adjuvant | Antigen μg/dose | Antigen conc. μg/mL | Dose volume | Route of administration |
|---|---|---|---|---|---|---|
| 0 | 1$^{st}$ | CFA | 10 | 50 | 200 μl | s.c. |
| 21 | 2$^{nd}$ | IFA | 10 | 50 | 200 μl | s.c. |
| 42 | 3$^{rd}$ | IFA | 10 | 50 | 200 μl | s.c. |
| 69 | 4$^{th}$ | IFA | 10 | 50 | 200 μl | s.c. |
| 86 | 5$^{th}$ | PBS | 10 | 100 | 100 μl | i.p. |
| 89 | Organ harvest | — | — | — | — | — |

FACS Sorting of Murine Plasma Cells

To remove red blood cells the pooled cell suspension was lysed in 0.17 M NH$_4$Cl. Following lysis the cells were washed twice in 2% FBS/PBS. Cells were re-suspended in 1 ml 2% FBS/PBS, incubated with Fc-block (anti-mouse CD16/CD32, BD Biosciences, Cat. No. 553141) and washed once. Following re-suspension in 2% FBS/PBS, the cells were stained with anti-mouse CD43-FITC (BD Biosciences, Cat. No. 553270), anti-mouse CD138-PE (BD Biosciences, Cat. No. 553714), anti-mouse IgM-Horizon (BD Biosciences, Cat. No. 560575), anti-mouse IgG1-APC (BD Biosciences, Cat. No. 550874), anti-mouse MHC II (I-A/I-Ed)-biotin (BD Biosciences, Cat. No. 553622) and anti-mouse B220/CD45R-PerCP (BD Biosciences, Cat. No. 553093) for 20 min in the dark. Cells were washed, incubated with Streptavidin-APC-Cy7 (BD Biosciences, Cat. No. 554063) for 20 min and washed. Cells were FACS sorted on a FACSAria cell sorter. Cells that were B220$^{low}$MHCII$^{int}$CD43$^+$CD138$^+$IgM$^-$ were single cell sorted into 384-well micro titer plates containing PCR reaction buffer. Plates were centrifuged, frozen and stored at −80° C.

Linkage of Cognate V$_H$ and V$_L$ Pairs

Linkage of V$_H$ and V$_L$ coding sequences was performed on the single cells gated as plasma cells, facilitating cognate pairing of the V$_H$ and V$_L$ coding sequences. The procedure utilized a two step PCR procedure based on a one-step multiplex overlap-extension RT-PCR followed by a nested PCR. The primer mixes used in the present example only amplify kappa light chains. Primers capable of amplifying lambda light chains could, however, be added to the multiplex primer mix and nested PCR primer mix if desired. If lambda primers are added, the sorting procedure should be adapted such that lambda positive cells are not excluded. The principle for linkage of cognate V$_H$ and V$_L$ sequences is described in detail in WO 2005/042774 and in Meijer et al. (2006) *J Mol Biol.* 358(3):764-72.

96-well PCR plates were thawed and the sorted cells served as template for the multiplex overlap-extension RT-PCR. The sorting buffer added to each well before the single-cell sorting contained reaction buffer (OneStep RT-PCR Buffer; Qiagen), primers for RT-PCR and RNase inhibitor (RNasin, Promega).). The primers used for the overlap extension RT-PCR as well as the primer concentrations were the same as those listed in Table 3 of WO 2008/104183. This was supplemented with OneStep RT-PCR5Enzyme Mix (25× dilution; Qiagen) and dNTP mix (200 μM each) to obtain the given final concentration in a 20 μl reaction volume. The plates were incubated for 30 min at 55° C. to allow for reverse transcription (RT) of the RNA from each cell. Following the RT, the plates were subjected to the following PCR cycle: 10 min at 94° C., 35× (40 sec at 94° C., 40 sec at 60° C., 5 min at 72° C.), 10 min at 72° C.

The PCR reactions were performed in a H2OBIT Thermal Cycler with a Peel Seal Basket for 24 96-well plates (AB-gene) to facilitate a high-throughput. The PCR plates were stored at −20° C. after cycling.

For the nested PCR step, 96-well PCR plates were prepared with the following mixture in each well (20 µl reactions) to obtain the given final concentration: 1× Fast-Start buffer (Roche), dNTP mix (200 µM each), nested primer mix, Phusion DNA Polymerase (0.08 U; Finnzymes) and FastStart High Fidelity Enzyme Blend (0.8 U; Roche). The primers used for the nested PCR as well as the primer concentrations were the same as those listed in Table 4 of WO 2008/104183. As template for the nested PCR, 1 µl was transferred from the multiplex overlap-extension PCR reactions. The nested PCR plates were subjected to the following thermocyling: 35× (30 sec at 95° C., 30 sec at 60° C., 90 sec at 72° C.), 10 min at 72° C. Randomly selected reactions were analyzed on a 1% agarose gel to verify the presence of an overlap-extension fragment of approximately 890 base-pairs (bp). The plates were stored at −20° C. until further processing of the PCR fragments.

The repertoires of linked $V_H$ and $V_L$ coding pairs from the nested PCR were pooled, without mixing pairs from different donors, and were purified by preparative 1% agarose gel electrophoresis. The human kappa constant light chain encoding sequence was spliced by overlap extension to the $V_L$ coding region of the pooled PCR products of linked $V_H$ and $V_L$ coding pairs as described in WO 2008/104183. The human kappa constant light chain encoding sequence was amplified from a plasmid containing the coding sequence of a human antibody with a kappa light chain in a reaction containing: Phusion Enzyme (2 U; Finnzymes), 1× Phusion buffer, dNTP mix (200 µM each), hKCforw-v2 primer and Kappa3' primer (see Table 5 of WO 2008/104183 for primers and concentrations used), and plasmid template pLL138 (10 ng/µl) in a total volume of 50 µl. The reaction was subjected to the following thermocycling: 25× (30 sec at 95° C., 30 sec at 55° C., 45 sec at 72° C.), 10 min at 72° C. The resulting PCR fragment was purified by preparative 1% agarose gel electrophoresis.

The purified pooled PCR fragments from each repertoire were spliced to the amplified and purified PCR fragment of the human kappa constant encoding region (SEQ ID NO:41) by the following splicing by overlap extension PCR (50 µl total volume) containing: human kappa constant encoding region fragment (1.4 ng/µl), purified pooled PCR fragment (1.4 ng/µl), Phusion DNA Polymerase (0.5 U; Finnzymes) and FastStart High Fidelity Enzyme Blend (0.2 U; Roche), 1× FastStart buffer (Roche), dNTP mix (200 µM each), mhKCrev primer and mJH set primers (see Table 5 of WO 2008/104183 for primers and concentrations used). The reaction was subjected to the following thermocycling: 2 min at 95° C., 25× (30 sec at 95° C., 30 sec at 55° C., 1 min at 72° C.), 10 min at 72° C. The resulting PCR fragment (approx. 4518 bp) was purified by preparative 1% agarose gel electrophoresis.

Insertion of Cognate $V_H$ and $V_L$ Coding Pairs into a Screening Vector

In order to identify antibodies with binding specificity to HER3, the $V_H$ and $V_L$ coding sequences obtained were expressed as full-length antibodies. This involved insertion of the repertoire of $V_H$ and $V_L$ coding pairs into an expression vector and transfection into a host cell.

A two-step cloning procedure was employed for generation of a repertoire of expression vectors containing the linked $V_H$ and $V_L$ coding pairs. Statistically, if the repertoire of expression vectors contains ten times as many recombinant plasmids as the number of cognate paired $V_H$ and $V_L$ PCR products used for generation of the screening repertoire, there is a 99% likelihood that all unique gene pairs are represented. Thus, if 400 overlap-extension V-gene fragments were obtained, a repertoire of at least 4000 clones would be generated for screening to have a 99% likelihood of obtaining all unique gene pairs.

Briefly, the purified PCR product of the repertoires of linked $V_H$ and $V_L$ coding pairs, spliced to the human kappa constant coding region, were cleaved with XhoI and NotI DNA endonucleases at the recognition sites introduced into the termini of PCR products. The cleaved and purified fragments were ligated into an XhoI/NotI digested mammalian IgG expression vector, OO-VP-002 (described in WO 2008/104183), by standard ligation procedures. The ligation mix was electroporated into *E. coli* and added to 2×YT plates containing the appropriate antibiotic and incubated at 37° C. overnight. The amplified repertoire of vectors was purified from cells recovered from the plates using standard DNA purification methods (Qiagen). The plasmids were prepared for insertion of promoter-leader fragments by cleavage using AscI and NheI endonucleases. The restriction sites for these enzymes were located between the $V_H$ and $V_L$ coding gene pairs. Following purification of the vector, an AscI-NheI digested bi-directional mammalian promoter-leader fragment was inserted into the AscI and NheI restriction sites by standard ligation procedures. The ligated vector was amplified in *E. coli* and the plasmid was purified using standard methods. The generated repertoire of screening vectors was transformed into *E. coli* by conventional procedures. Colonies obtained were consolidated into 384-well master plates and stored.

A two-step procedure was employed for amplification of mammalian expression plasmids. First bacteria were lysed and DNA denatured by incubation in sodium hydroxide. Subsequently, the TempliPhi amplification was performed (GE Amersham). This method utilizes bacteriophage Φ29 DNA polymerase to exponentially amplify double-stranded circular DNA templates by rolling circle amplification. For antibody expression in mammalian cells, the 293Freestyle™ expression system (Invitrogen) was applied using standard transfection conditions as recommended by the manufacturer. The cells were supplemented with valproate to 50 mM prior to transfection and the next day Tryptone N1 was added to a final concentration of 1.5% (w/v) of the transfection volume. Supernatants containing antibodies were harvested six days post transfection. Expression levels were estimated with standard anti-IgG ELISA.

Screening for Binding to Recombinant HER3 Protein (ELISA)

Antibody specificity was determined by ELISA using recombinant HER3-protein as antigen.

Briefly, Nunc Maxisorb plates (cat.#464718) were coated with 1 µg/ml HER3 protein (R&D Systems cat.#348-RB), diluted in PBS at 4° C. overnight. Prior to blocking in 50 µl 2% Milk-PBS+0.05% Tween 20 the plates were washed once with PBS-T. The plates were washed once with PBS-T and 20 µl of 2% milk-PBS-T, and 10 µl supernatants from FreeStyle293 transfectants were added and incubated for 1 hour at room temperature, after which the plates were washed once with PBS-T, 20 µl per well. Secondary antibody (HRP-Goat-anti-human kappa light chain, Serotec, cat.# STAR 100P) diluted 1:25000 in 2% milk-PBS-T was added to detect the antibodies bound to the wells and incubated for 1 hour at room temperature. The plates were washed once in PBS-T before addition of 25 µl substrate (Kem-En-Tec Diagnostics, cat.#4518) that was incubated for 5 min. 25 µl 1M sulphuric acid was added after the incubation to stop the reaction. Specific signal was detected on an ELISA reader at 450 nm. From the ELISA data 480 positive antibody clones were identified and selected for sequence analysis and validation of binding to HER3.

Sequence Analysis and Clone Selection

The clones identified as binding to HER3 by ELISA were retrieved from the original master plates (384-well format) and streaked on agar plates to generate single colonies, which were picked to LB-medium cultures and incubated at 37° C. ON with vigorous shaking. Plasmid DNA was isolated from the clones using Qiaprep 96 turbo mini-prep kit (Qiagen, cat. #27193) and submitted for DNA sequencing of the V-genes. The sequences were aligned and all the unique clones were selected. Multiple alignments of obtained sequences revealed the uniqueness of each particular clone and allowed for identification of unique antibodies. Following sequence analysis of the sequenced clones, 33 clusters of related sequences with two to over forty members as well as over 20 clonotypes that were only represented once were identified. Each cluster of related sequences has probably been derived through somatic hypermutations of a common precursor clone. Overall, one to two clones from each cluster were chosen for validation of sequence and specificity. Based on the cluster analysis, 119 clones were selected for small-scale expression and further characterization. Sequences of selected antibody variable regions are shown in the sequence listing. The light chain sequences shown in the sequence listing all include the same human kappa constant region, which starts with amino acids -TVAAP- and ends at the C-terminal -NRGEC. In order to validate the antibody encoding clones, DNA plasmid was prepared and transfection of FreeStyle CHO-S cells (Invitrogen) at 2 ml scale was performed for expression. The supernatants were harvested 6 days after transfection. Expression levels were estimated with standard anti-IgG ELISA, and the specificity was determined by HER3 specific ELISA as described above in "Screening for binding to recombinant HER3 protein" and high throughput screening confocal microscopy of antibody binding to HER3 overexpressing cells (see below).

Screening for Binding to HER3 Overexpressing Cells (OPERA)

The 119 clones were screened for binding to the HER3-overexpressing breast cancer cell line (MCF-7) using confocal microscopy. 10,000 MCF-7 cells were seeded into each well of 384-well cell carrier plates (Perkin Elmer, cat.#6007439) and allowed to attach overnight. The media was again discarded and the cells were washed and fixed with 2% formaldehyde solution (Aldrich cat.#533998). After washing, 40 µl of antibody supernatant was transferred to each well and plates were incubated for 2 hours, after which the media in the wells was discarded and 30 µl new media containing 2 µg/ml of Alexa-488 labeled goat anti-human IgG (H+L, Invitrogen cat.# A11013), 2 µg/ml Cell-Mask Blue (Invitrogen cat.# H34558) and 1 µM Hoechst 33342 (Invitrogen cat.# H3570) was added to each well and plates were incubated for another 30 minutes. The level of fluorescence was then measured using an OPERA high throughput confocal microscope (Perkin Elmer).

From the binding data obtained by ELISA and OPERA validation screens, 64 clones were selected for medium scale expression.

Example 2

Selection of an Optimal Antibody Mixture Against EGFR, HER2 and HER3 Respectively This example demonstrates that mixtures of antibodies against each individual HER family receptor (EGFR, HER2 and HER3) are superior to the individual antibodies.

Methods

Three monoclonal antibodies against each receptor were selected for this study (Table 5). The antibodies against each receptor bind non-overlapping epitopes as confirmed by Surface Plasmon Resonance analyses.

TABLE 5

Antibodies used in the study

| Target | Antibody |
|---|---|
| EGFR | 992 chimeric IgG1 |
| EGFR | 1024 chimeric IgG1 |
| EGFR | 1030 chimeric IgG1 |
| HER2 | 4382 chimeric IgG1 |
| HER2 | 4385 chimeric IgG1 |
| HER2 | 4518 chimeric IgG1 |
| HER3 | 4785 chimeric IgG1 |
| HER3 | 5082 chimeric IgG1 |
| HER3 | 5096 chimeric IgG1 |

The selected antibodies and antibody mixtures were tested for ability to inhibit the growth and proliferation of the cancer cell lines A431NS (EGFR), NCI-N87 (HER2) and MCF-7 cells stimulated with 10 nM heregulin beta (HER3) using a viability assay. Cellular damage will inevitably result in loss of the ability of the cell to maintain and provide energy for metabolic cell function and growth. Metabolic activity assays are based on this premise and usually they measure mitochondrial activity. The Cell Proliferation Reagent WST-1 (Roche Cat. No 11 644 807 001) is a ready-to-use substrate which measures the metabolic activity of viable cells. It is assumed that the metabolic activity correlates with the number of viable cells. In this example the WST-1 assay was used to measure the number of metabolically active cells after treatment of cancer cells with different concentrations of antibodies for 96 hours.

Prior to performing the WST-1 assay the appropriate antibodies and antibody mixes were diluted to a final total antibody concentration of 100 µg/ml in appropriate media supplemented with 2% of FBS and 1% P/S yielding a final total antibody concentration of 50 µg/ml in the well containing the highest antibody concentration. A threefold serial dilution of the antibodies was then performed. Relevant numbers of cells were then added to the experimental wells in a 384-well plate. The plates were incubated for 4 days in a humidified incubator at 37° C. WST-1 reagent was then added to the plates and the plates were incubated for one hour at 37° C. Plates were transferred to an orbital plate shaker for one hour and the absorbance was measured at 450 and 620 nm (reference wavelength) using an ELISA reader. The amount of metabolically active cells (MAC) is calculated as a percentage of the untreated control as follows:

$$\% \ MAC = \left( \frac{(ODexp. - ODmedia)}{(ODuntreat. - ODmedia)} \right) \times 100$$

Results

Results from the titrations of the three anti-EGFR antibodies and all possible mixtures of these on the cell line A431NS are shown in FIG. 1A. It is evident that mixtures of antibodies are superior to the individual antibodies. The antibody mixture consisting of 992 and 1024 was selected as it had the highest efficacy and potency. Results from the titrations of the three anti-HER2 antibodies and all possible mixtures of these on the cell line NCI-N87 are shown in FIG. 1B. Again mixtures of antibodies were superior to the individual antibodies. The antibody mixture consisting of 4382, 4385 and 4518 was selected as it had the highest efficacy and potency. Results from the titrations of the three anti-HER3 antibodies and all possible mixtures of these on the cell line MCF7 stimulated with 10 nM of heregulin beta are shown in FIG. 1C. It was difficult to discriminate between the best monoclonal antibody 5082 and the best antibody mixture 4785+5082. However, there was a slight trend that the mixture was better and therefore it was selected for testing of pan-HER mixtures.

Example 3

Cancer Inhibitory Activity of Pan-HER Antibody Mixtures

This example demonstrates that the optimal targeting of more than one of the HER family receptors is obtained by combining mixtures of antibodies against each receptor and that targeting three receptors is superior to targeting two receptors.

Methods

The optimized mixtures against the three receptors, 992+1024 (EGFR), 4382+4385+4518 (HER2) and 4785+5082 (HER3), as well as all possible mixtures of these were tested for ability to inhibit the growth and proliferation of the cancer cell lines A431NS (EGFR), NCI-N87 (HER2) and MCF-7 cells stimulated with 10 nM heregulin beta (HER3) using a viability assay similar to the one described in Example 2.

Results

Figure 2:
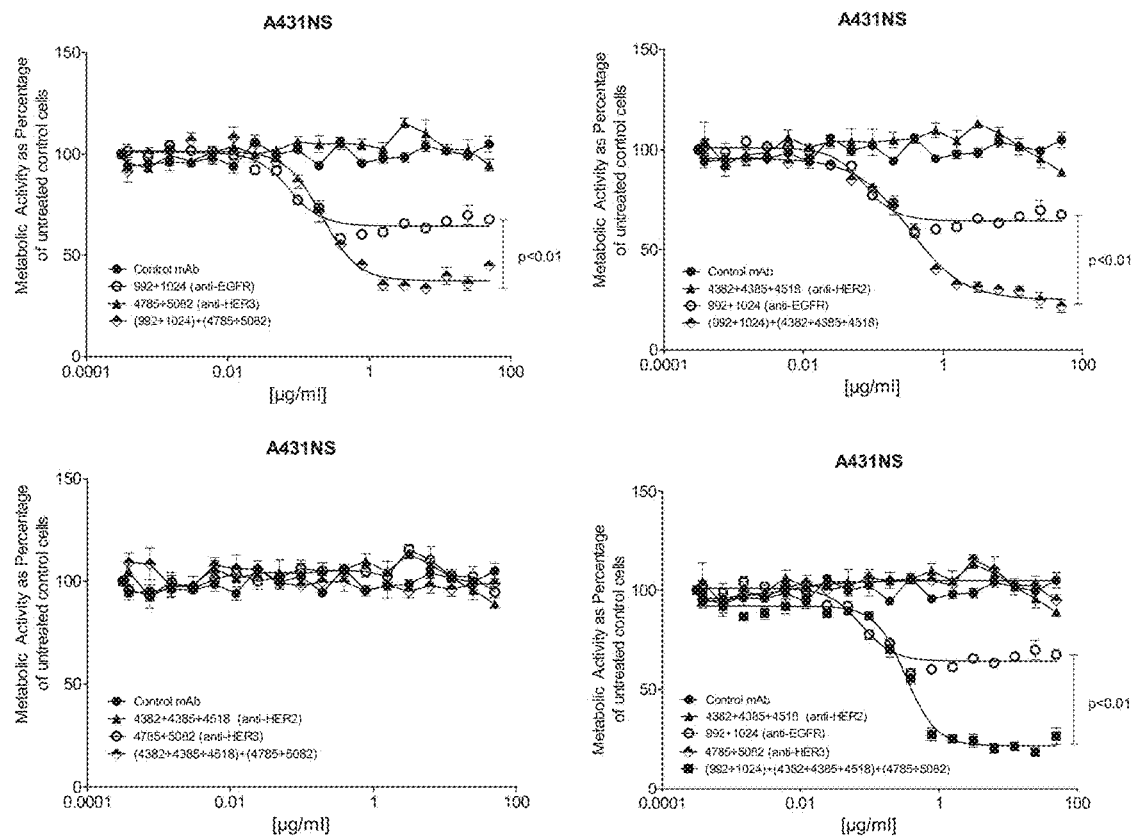
FIG. 2: Metabolic activity of A431NS cells treated with different concentrations of the indicated mixtures for 96 hours.
Figure 3:
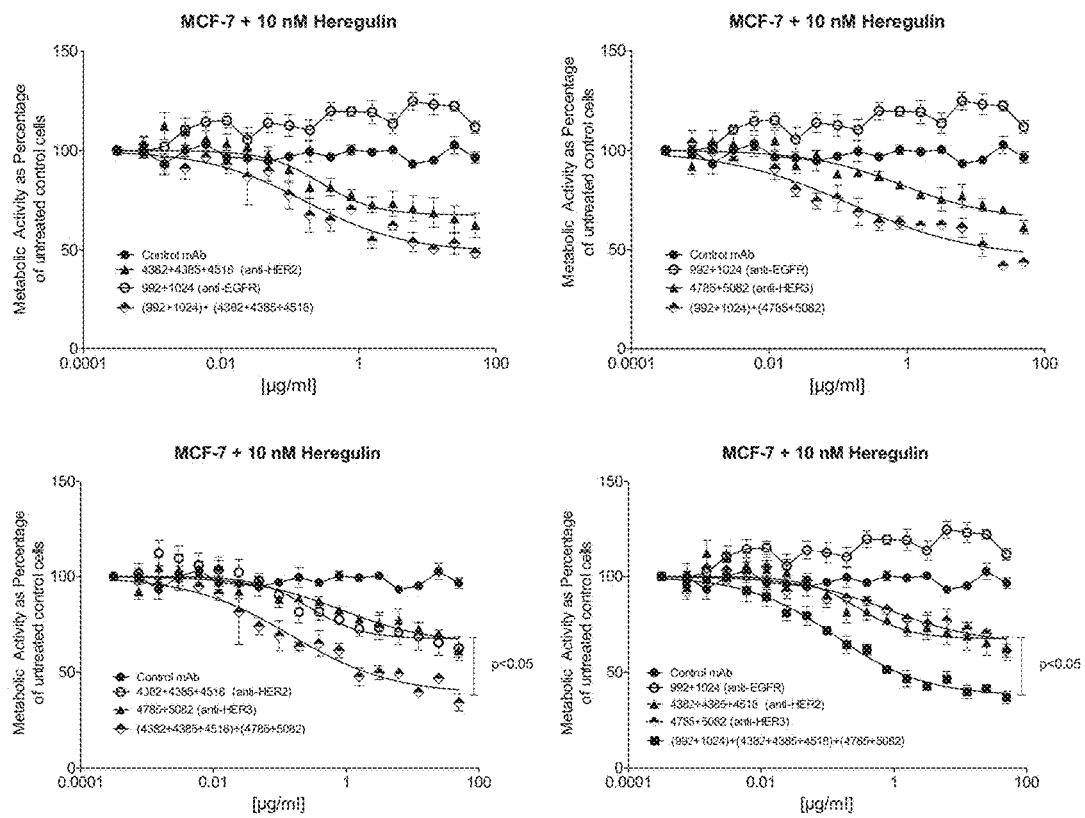
FIG. 3: Metabolic activity of MCF7 cells treated with different concentrations of the indicated antibody mixtures for 96 hours.
Figure 4:
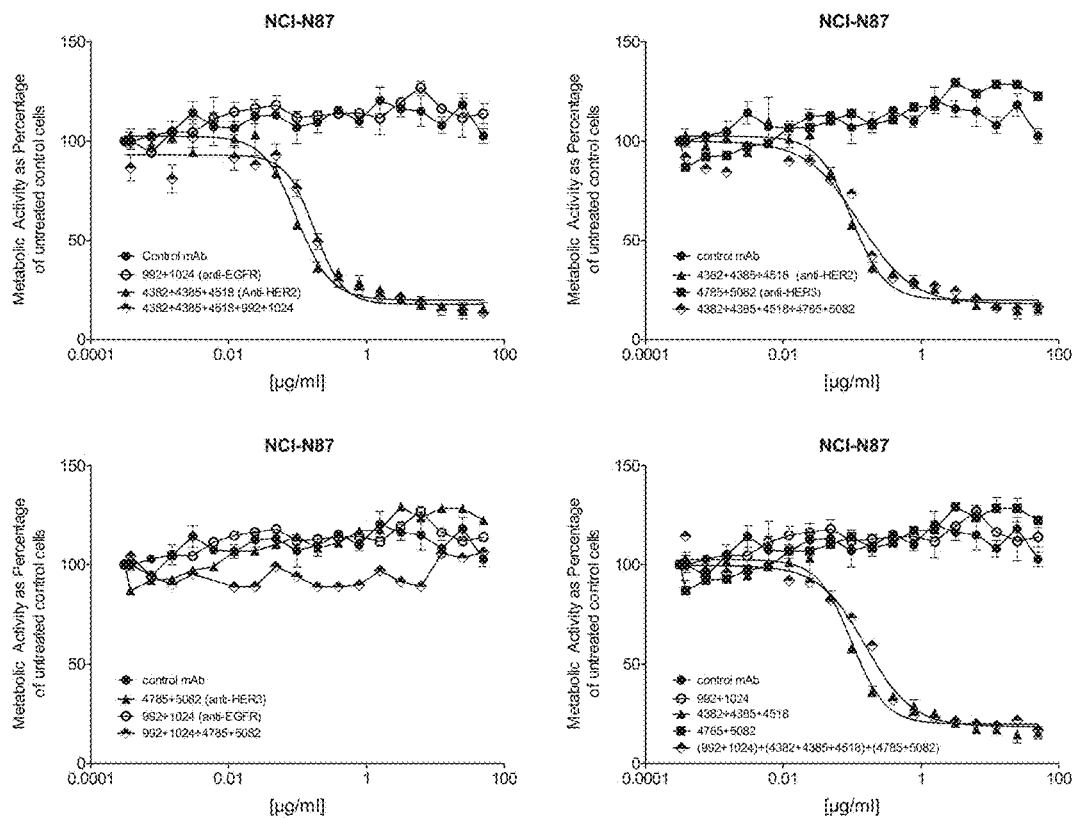
FIG. 4: Metabolic activity of NCI-N87 cells treated with different concentrations of the indicated antibody mixtures in the presence of 10 nM heregulin beta for 96 hours.

Results from the titrations of the three antibody mixtures and all possible mixtures of these on the cell lines A431NS, MCF7 and NCI-N87 are shown in FIGS. 2, 3 and 4 respectively. In A431NS cells combinations of EGFR mixtures and HER3 or HER2 mixtures gave rise to synergistic increases in inhibition of cancer cell growth (FIG. 2). A combination of mixtures against HER2 and HER3 had no inhibitory effect on the A431NS cells. However, a combination of mixtures against all three receptors was superior to individual mixtures and to combinations of mixtures against two receptors.

Similar results were found in the MCF7 cell line (FIG. 3). Combinations of EGFR mixtures and HER3 or HER2 mixtures and HER2 and HER3 mixtures gave rise to synergistic increases in inhibition of cancer cell growth. The combination of mixtures against all three receptors was superior to individual mixtures and to combinations of mixtures against two receptors.

In the NCI-N87 cell line no increases in either potency or efficacy were obtained by combining the efficient anti-HER2 mixture with either an anti-EGFR mixture or an anti-HER3 mixture (FIG. 4). A combination of mixtures against EGFR and HER3 had no inhibitory effect on the NCI-N87 cells. The combination of mixtures against all three receptors had similar potency and efficacy to the anti-HER2 mixture.

Figure 5:
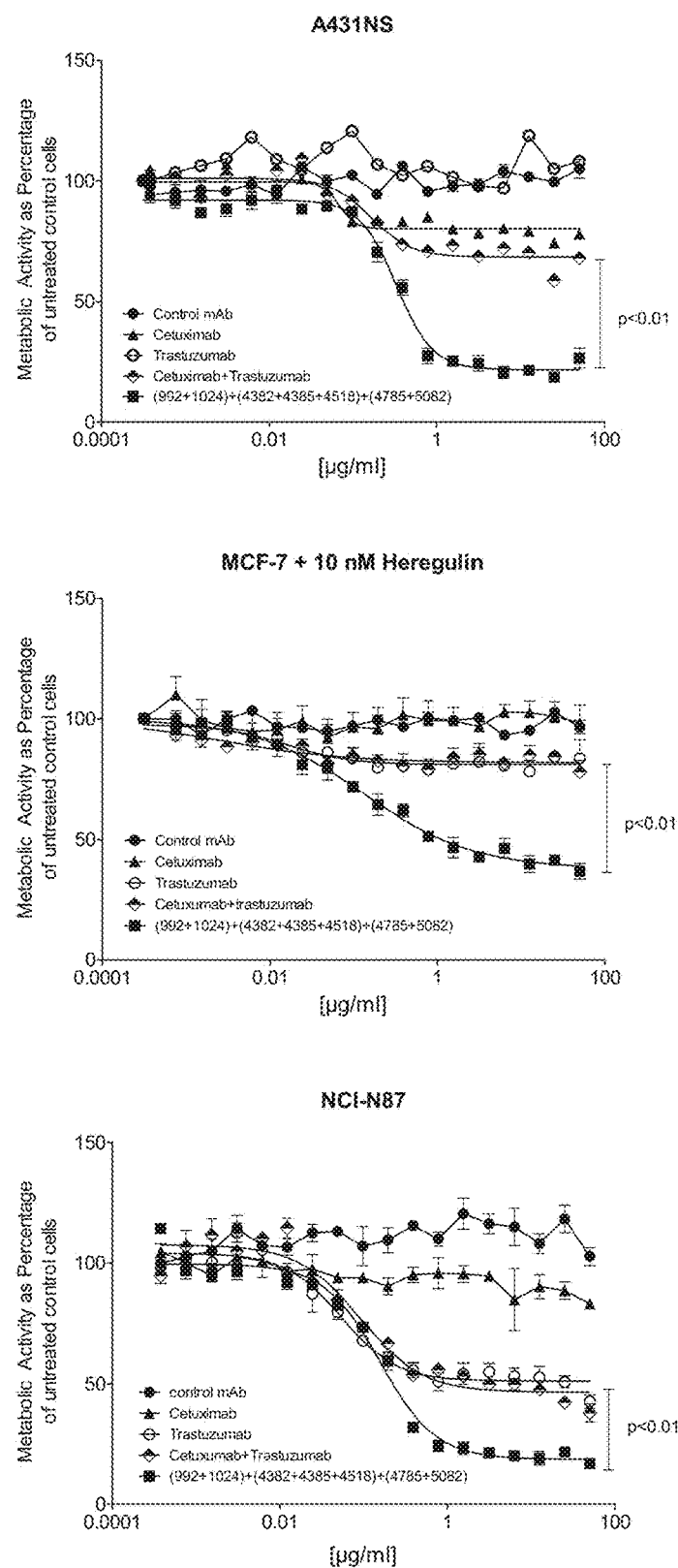
FIG. 5: Metabolic activity of A431NS cells treated with different concentrations of the indicated antibody mixtures and reference monoclonal antibodies cetuximab and trastuzumab for 96 hours, NCI-N87 cells treated with different concentrations of the indicated antibody mixtures and reference monoclonal antibodies cetuximab and trastuzumab for 96 hours and MCF7 cells treated with different concentrations of the indicated antibody mixtures and reference monoclonal antibodies cetuximab and trastuzumab in the presence of 10 nM Heregulin beta for 96 hours.

The combination of mixtures against all three receptors was compared to the marketed monoclonal antibodies cetuximab (EGFR) and trastuzumab (HER2) and a mixture of these two antibodies (FIG. 5). The results demonstrate that the pan-HER mixture is superior to both cetuximab and trastuzumab and also to a mixture of these two antibodies in all three cell lines. Overall the results in this example demonstrate that the optimal targeting of more than one of the HER family receptors is obtained by combining mixtures of antibodies against each receptor and that targeting three receptors is superior to targeting two receptors.

Example 4

Inhibitory Profile by Targeting the Two HER Family Receptors EGFR and HER2 Simultaneously with a Combination of Antibody Mixtures This example demonstrates that the combination of the anti-EGFR mixture and the HER2 mixture inhibits the cancer cell lines MCF7, HCC202, BT474, NCI-N87, MDA-MB-175, A431NS, HN5, H292, DU145 and MDA-MB-468.

Methods

The anti-EGFR mixture (992+1024), the anti-HER2 mixture (4382+4385+4518) and the combination of these two mixtures were investigated for ability to inhibit the growth of ten human cancer cell lines with EGFR or HER2 dependency. The marketed monoclonal antibodies cetuximab and trastuzumab were included as controls.

The cancer cell lines MCF7, HCC202, BT474, NCI-N87, MDA-MB-175, A431NS, HN5, H292, DU145 and MDA-MB-468 were seeded into 96-well plates at a concentration of 1000 cells/well in media containing 2 µg/ml of anti-HER2 antibody. The plates were incubated for 4 days in a humidified incubator at 37° C. Then 20 µl WST-1 reagent was added pr. well and the plates incubated for one hour at 37° C. Plates were then transferred to an orbital plate shaker and left for another hour. The absorbance was measured at 450 and 620 nm (reference wavelength) on an ELISA reader. The levels of growth inhibition were calculated as percentage of the untreated control cells.

Results

Figure 6:
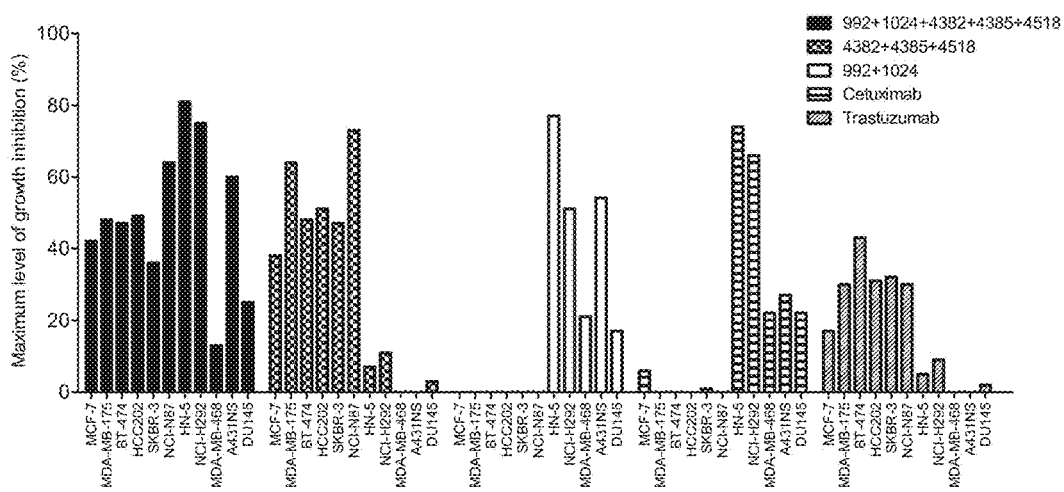
FIG. 6: Maximum level of growth inhibition of the indicated cell lines treated for 96 hours with 2 µg/ml of the indicated antibodies and antibody mixtures.

Results from the investigation of cell growth inhibition can be found in FIG. 6 and show that the combination of the anti-EGFR mixture and the HER2 mixture inhibits all the tested cell lines. Targeting of only one of the receptors results in inhibition of the cell lines that are dependent on that receptor. Overall these results show that a combination of mixtures of antibodies against EGFR and HER2 gives a much broader inhibitory profile and thus may ultimately be used to treat patients whose tumors are dependent on either of the receptors.

Example 5

Degradation of EGFR, HER2 and HER3 with a Combination of Antibody Mixtures

This example demonstrates that mixtures of antibodies induce degradation of their target (EGFR, HER2 or HER3) and that combinations of mixtures against all three targets can induce degradation of all receptors simultaneously.

Methods

Figure 7:
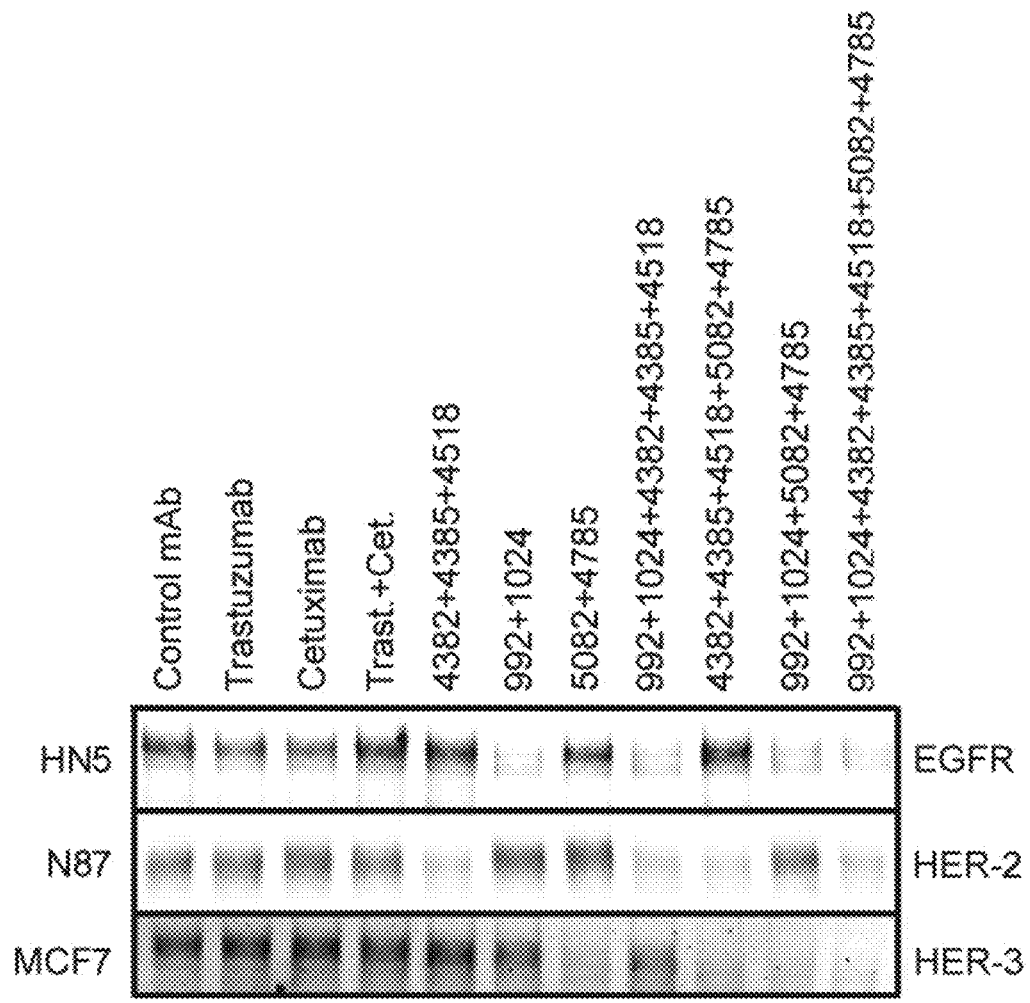
FIG. 7: Western blot analyses of EGFR, HER2 and HER3 levels in the cell lines HN5, NCI-N87 and MCF7 after overnight treatment with the indicated antibodies and antibody mixtures.
Figure 8:
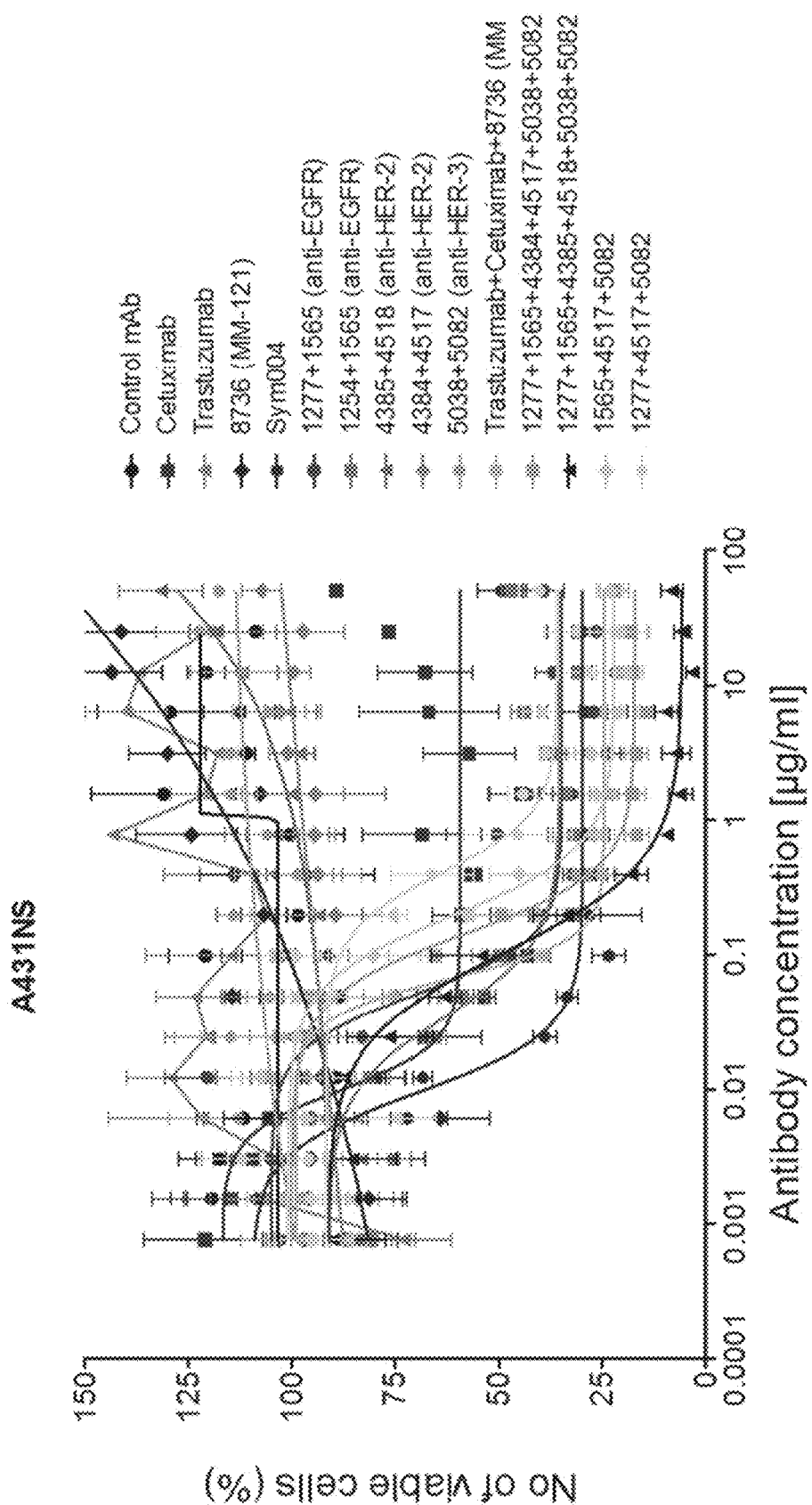
FIGS. 8-12: Titrations showing the effect of different antibody mixtures and antibodies on growth and proliferation of the cancer cell lines A431NS (EGFR-dependent), H358 (EGFR-dependent), HCC202 (HER2-dependent), OE19 (HER2-dependent) and H820 (EGFR-dependent).
Figure 9:
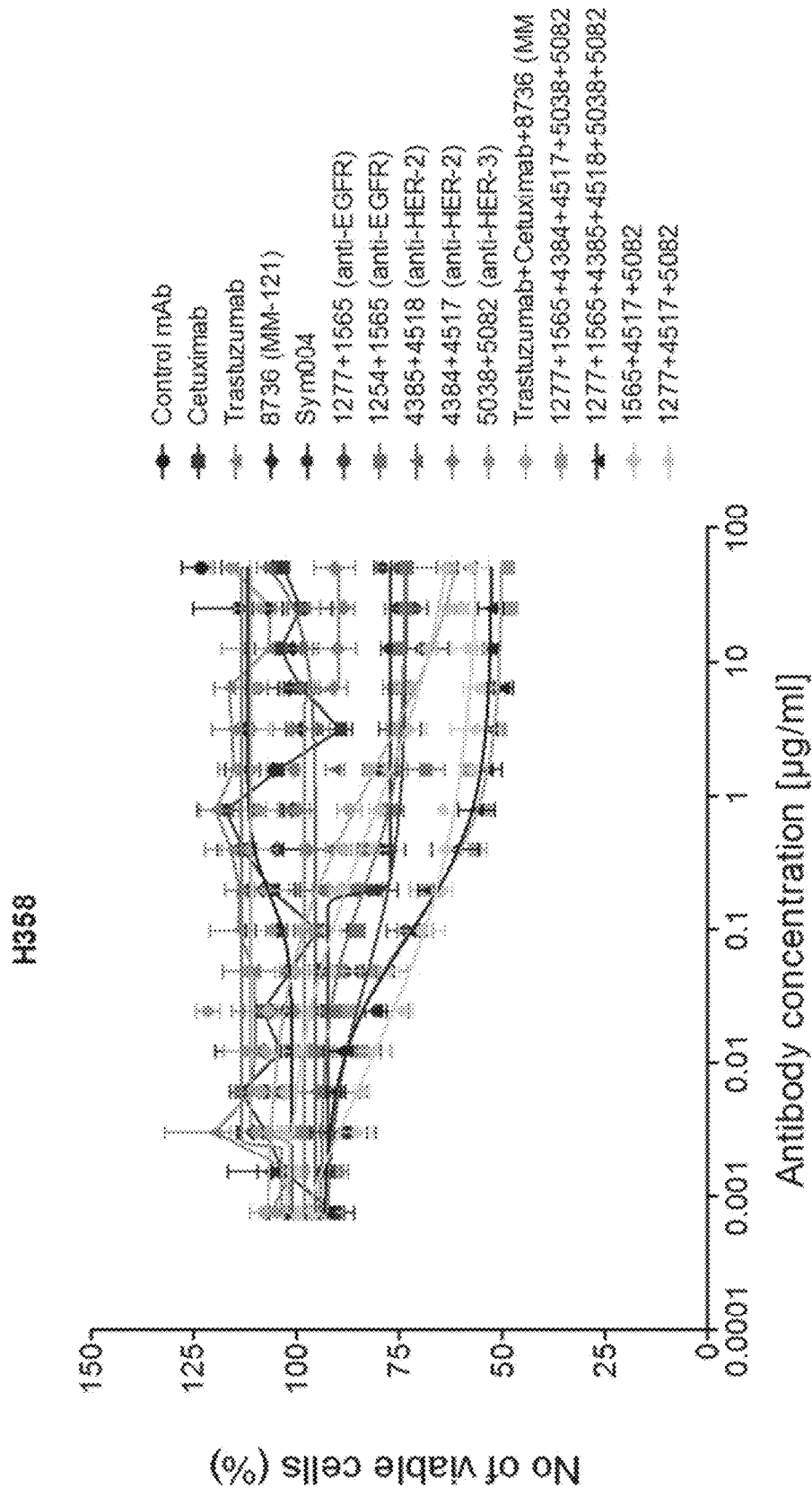
Figure 10:
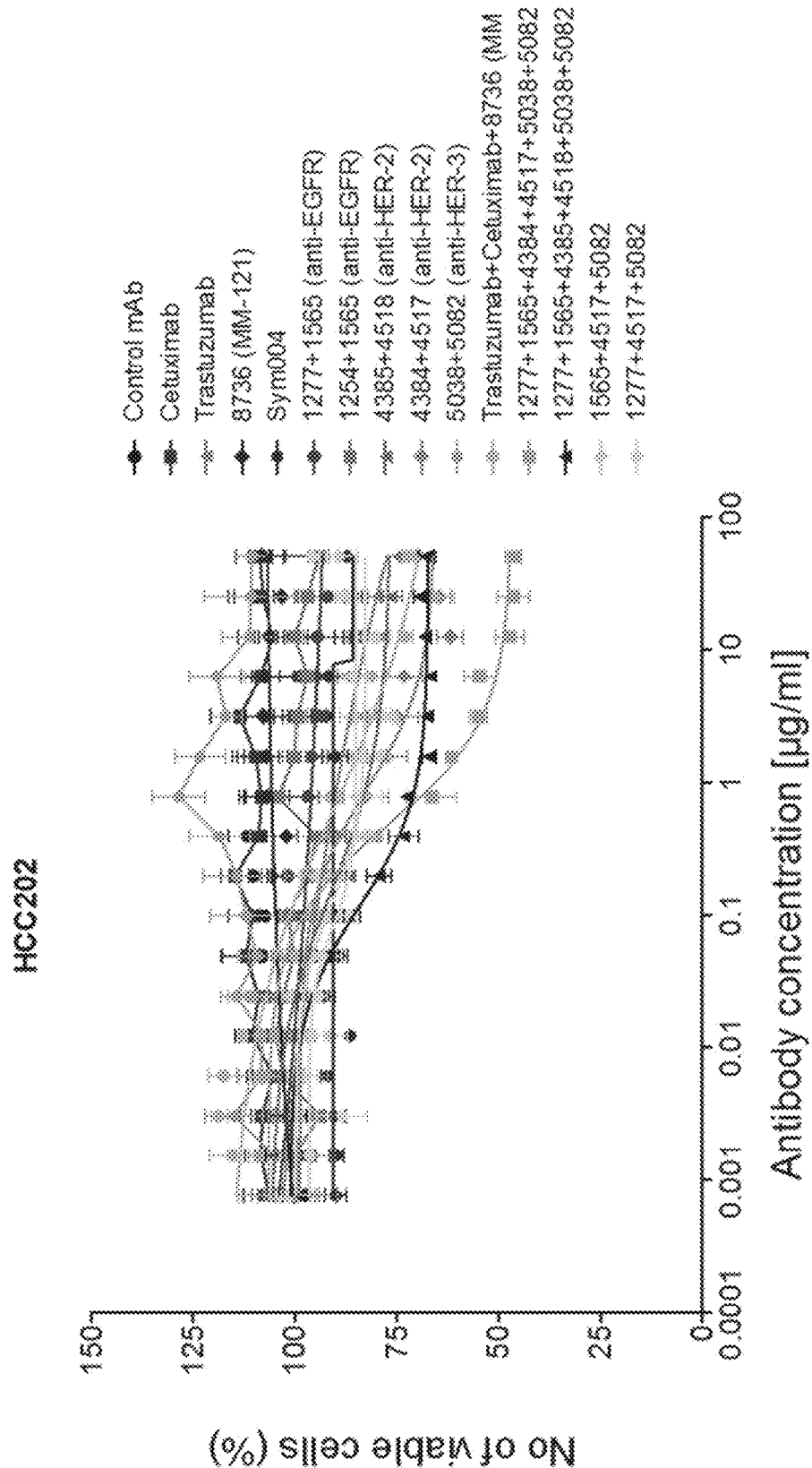
Figure 11:
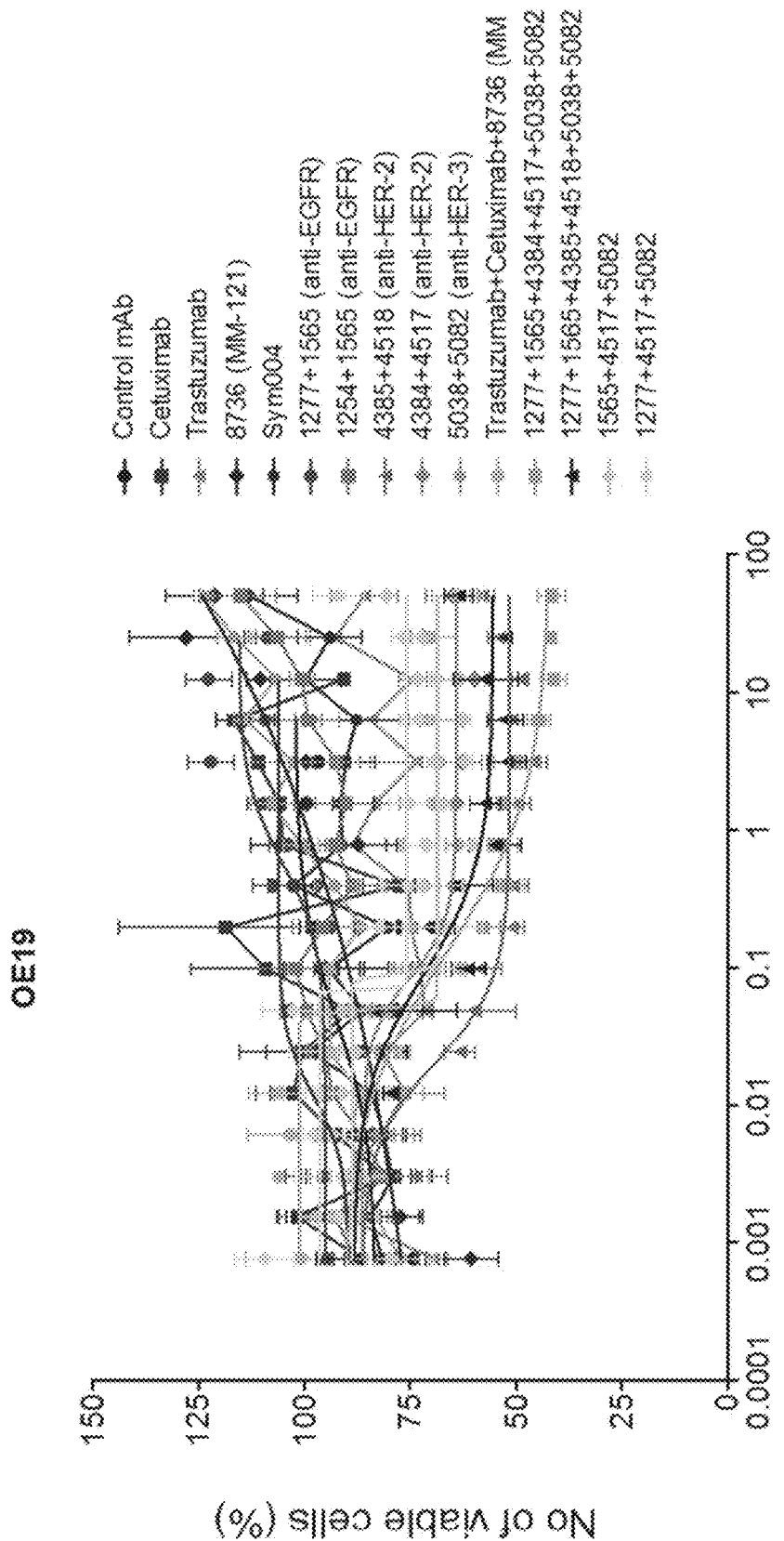
Figure 12:
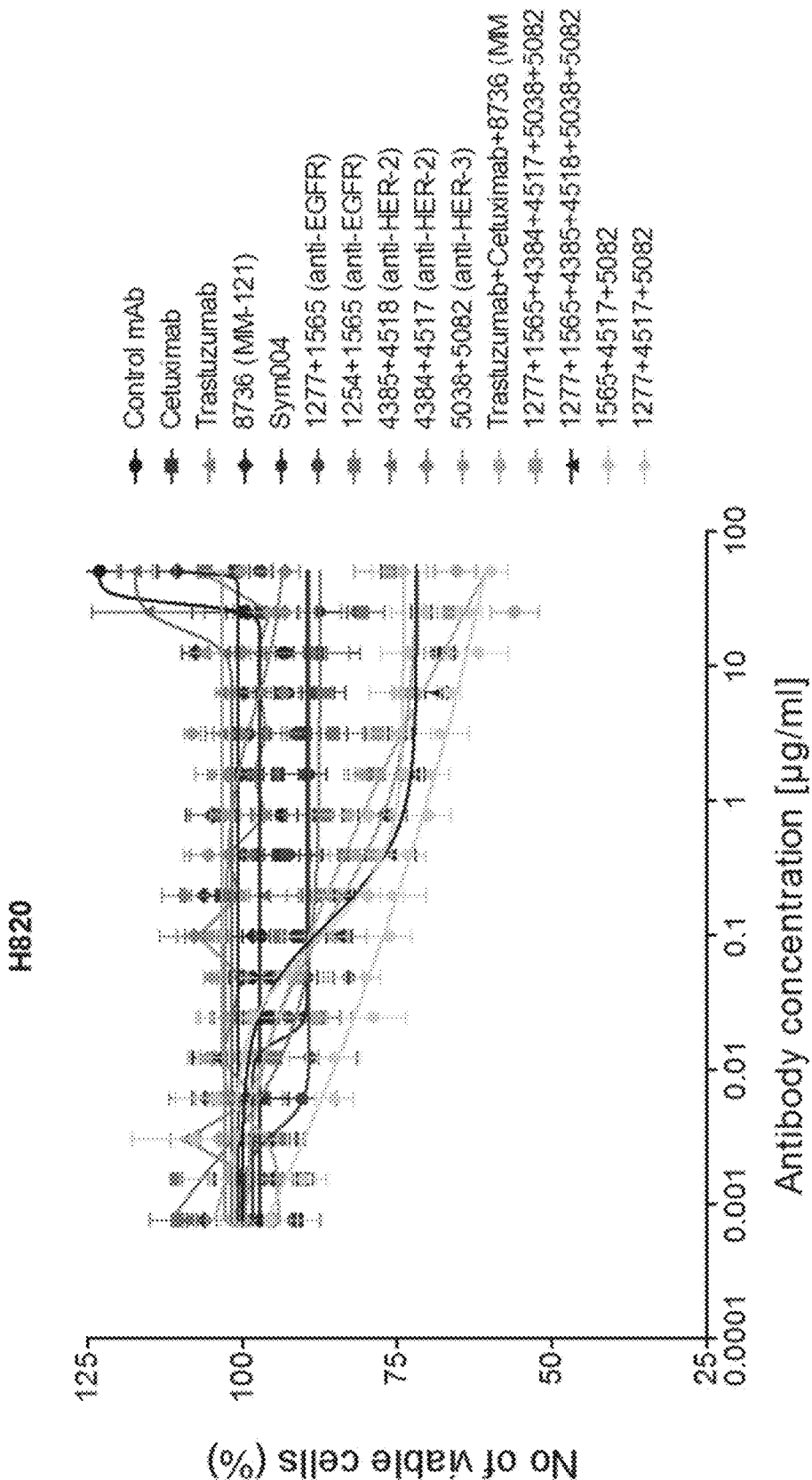

In order to investigate the level of EGFR, HER2 and HER3 degradation induced by antibody mixtures and combinations of mixtures, Western Blot analysis were performed on whole cell lysates of HN5, N87 and MCF7 cells treated with antibody for 48 hours. Cells were grown in T-75 culture flasks and when 50% confluent the culture media were removed, the cells washed in 1×PBS and treated with 20 µg/ml of the antibodies diluted in 5 ml medium containing 0.5% FBS. Cells were treated for 48 hours after which whole cell lysates were prepared using standard RIPA buffer. The total protein concentration was determined in each sample and 1-10 µg protein analyzed by western blotting using primary antibodies against EGFR, HER2 or HER3. An antibody against β-actin was used as loading control.
Results The results from the Western Blot investigation (FIG. 7) shows that mixtures of antibodies against a single receptor (EGFR, HER2 or HER3) induce degradation of their respective target and that a pan-HER mixture consisting of a combination of antibody mixtures against each target is able to induce efficient degradation of all three receptors simultaneously.

Example 6

Cancer Inhibitory Activity of Pan-HER Antibody Mixtures

Using the methods described in Example 3, the antibody mixtures Sym004 (containing the two anti-EGFR antibodies 992+1024 described in WO 2008/104183), 1277+1565 (anti-EGFR), 1254+1565 (anti-EGFR), 4385+4318 (anti-HER2), 4384+4517 (anti-HER2), 5038+5082 (anti-HER3), the pan-HER antibody mixtures 1565+4517+5082 and 1277+4384+5082 (one antibody against each of EGFR, HER2 and HER3), and 1277+1565+4384+4517+5038+ 5082 and 1277+1565+4385+4518+5038+5082 (two antibodies against each of EGFR, HER2 and HER3), the reference antibodies cetuximab (anti-EGFR), trastuzumab (anti-HER2), 8736 (MM-121 analogue; anti-HER3), and a mixture of the three reference antibodies, along with a negative control antibody, were tested for their ability to inhibit the growth and proliferation of 22 cancer cell lines that are dependent on EGFR or HER2, EGFR/HER2, HER2/HER3 or EGFR/HER2/HER3. The results of titrations of the antibody mixtures and antibodies listed above against the five cell lines A431NS (EGFR), H358 (EGFR), HCC202 (HER2), OE19 (HER2) and H820 (EGFR) are shown in FIGS. 8-12.
Results It can be seen from the results in FIGS. 8-12 that although the effect of the antibody mixtures and individual antibodies varies among the different cell lines, the pan-HER antibody mixtures containing antibodies against each of the three receptors EGFR, HER2 and HER3 are generally efficacious at inhibiting cell growth and proliferation. The pan-HER mixtures containing six antibodies, i.e. two antibodies against each of the three receptors, are in general the most efficacious across the different cell lines.

Example 7

Degradation of EGFR, HER2 and HER3 with a Combination of Antibody Mixtures

This example demonstrates that mixtures of antibodies induce degradation of their target (EGFR, HER2 or HER3) and that combinations of mixtures against all three targets can induce degradation of all receptors simultaneously.

Methods

Figure 13:
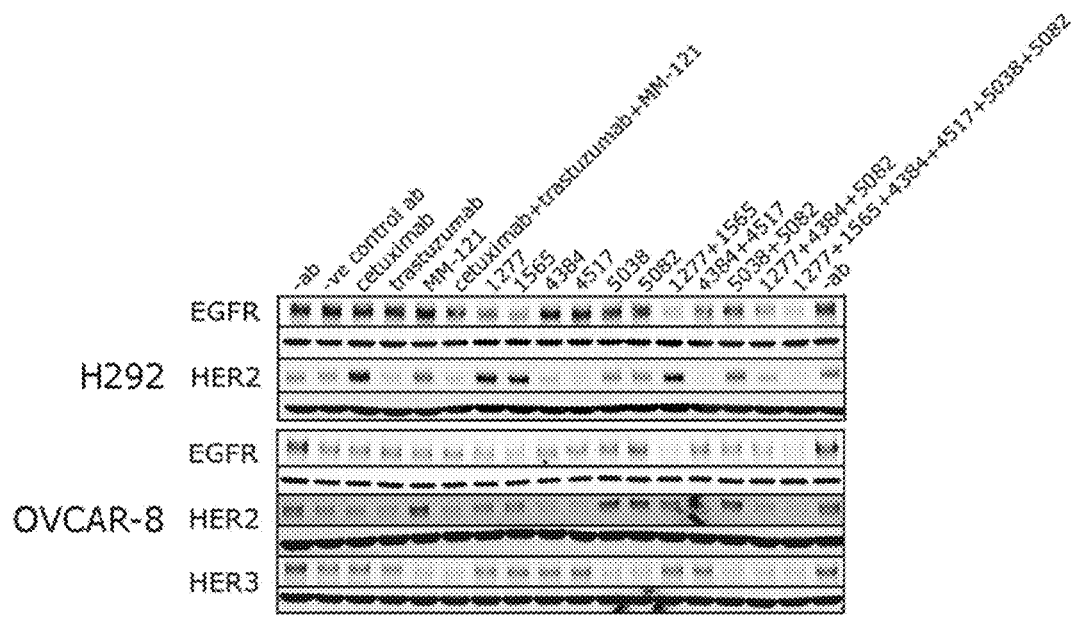
FIG. 13: Western blot analyses of EGFR, HER2 and HER3 levels in the cell lines H292 and OVCAR-8 after overnight treatment with the indicated antibodies and antibody mixtures.
Figure 14:
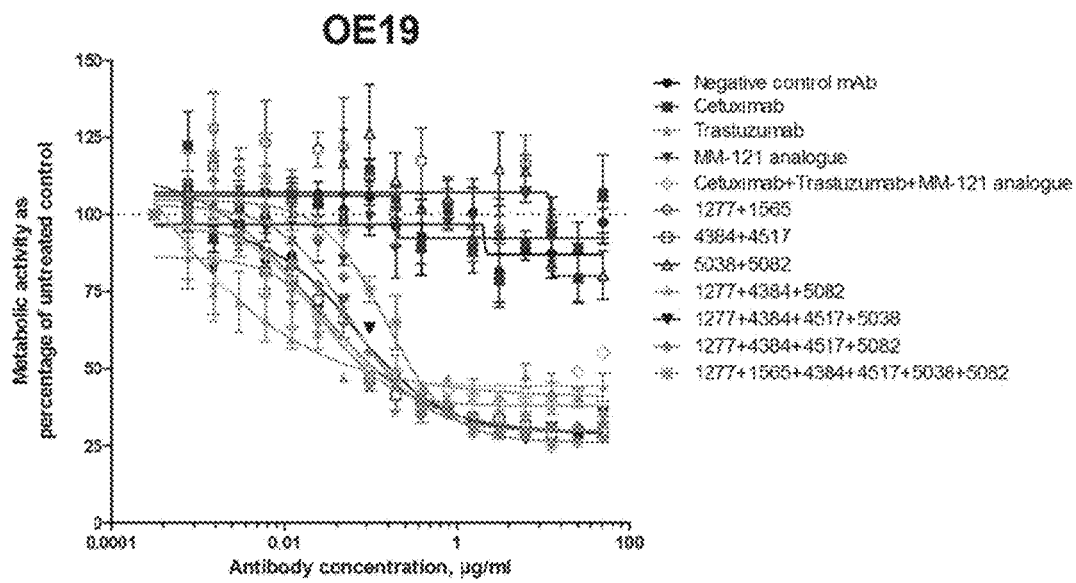
FIGS. 14-20: Titrations showing the effect of different antibody mixtures and antibodies on growth and proliferation of the cancer cell lines OE19, BT474, MDA-MB-175-VII, HCC202, N87, A431NS and A549.
Figure 15:
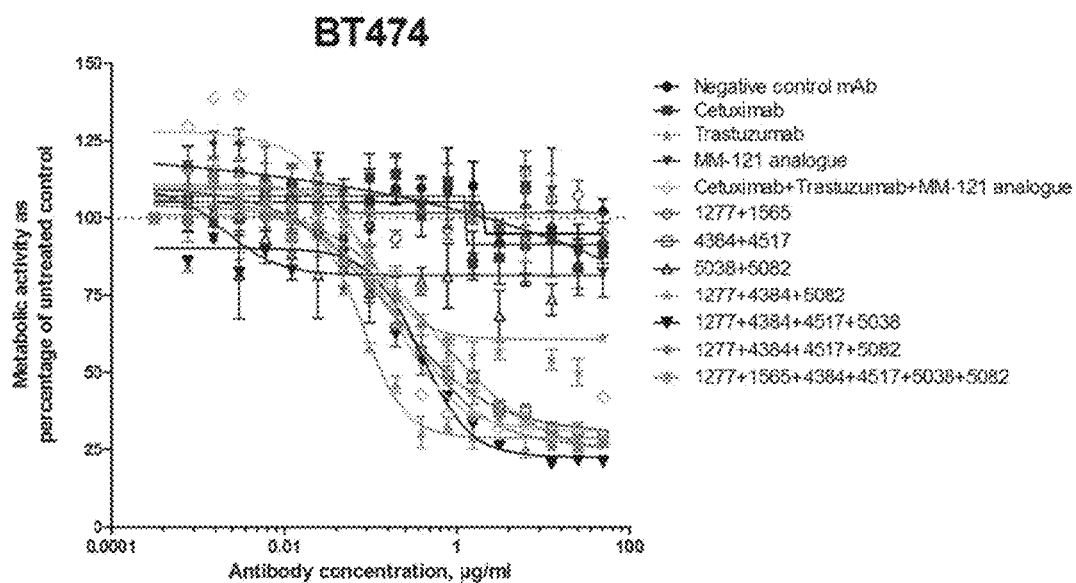
Figure 16:
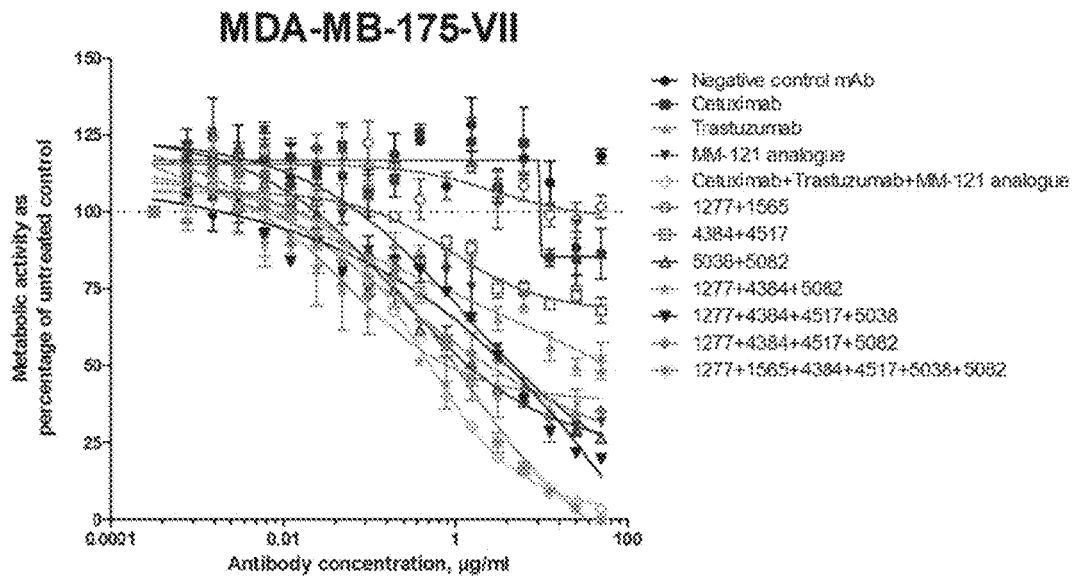
Figure 17:
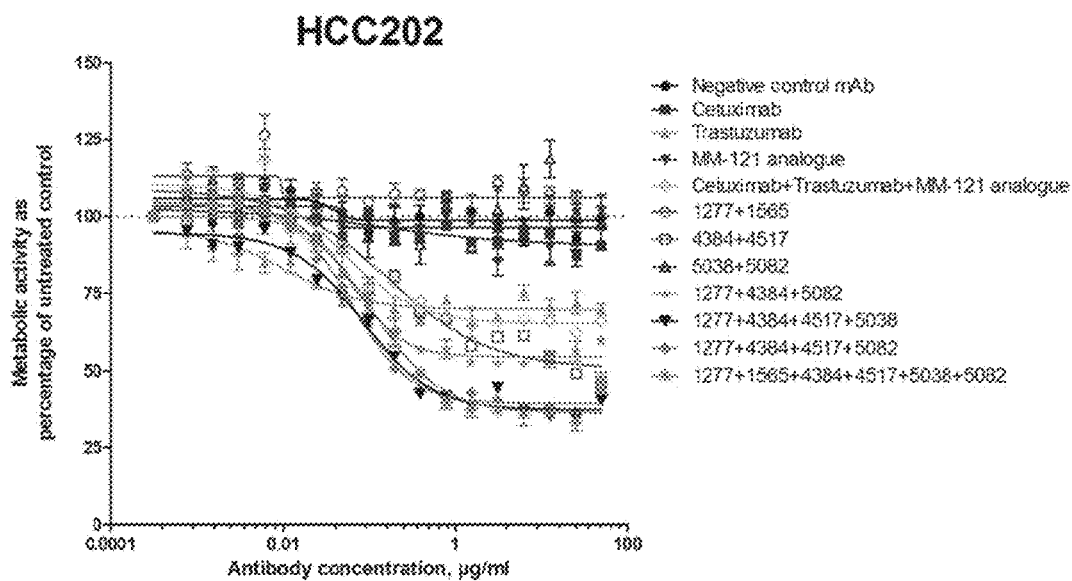
Figure 18:
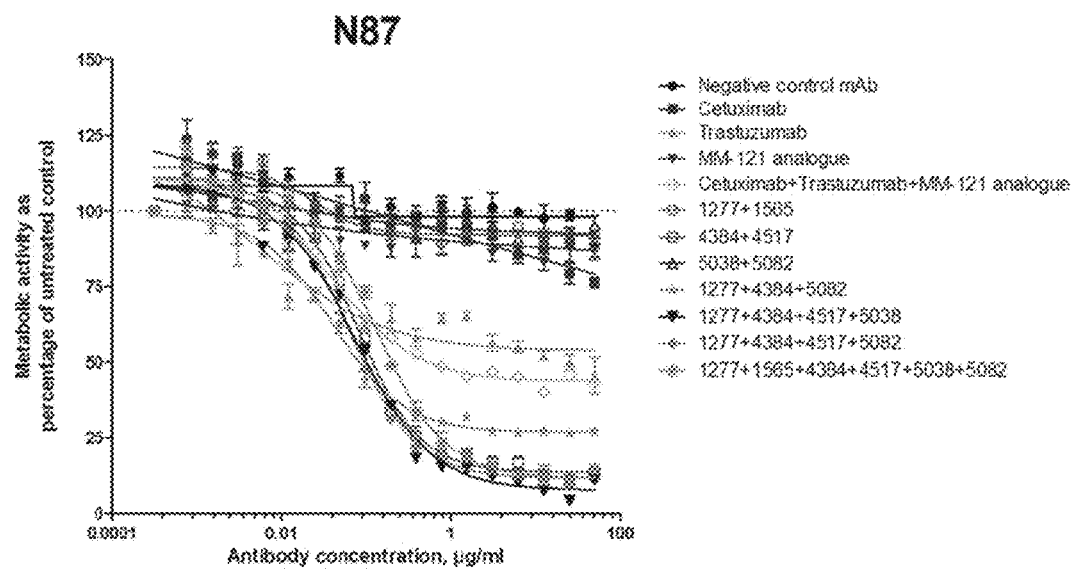
Figure 19:
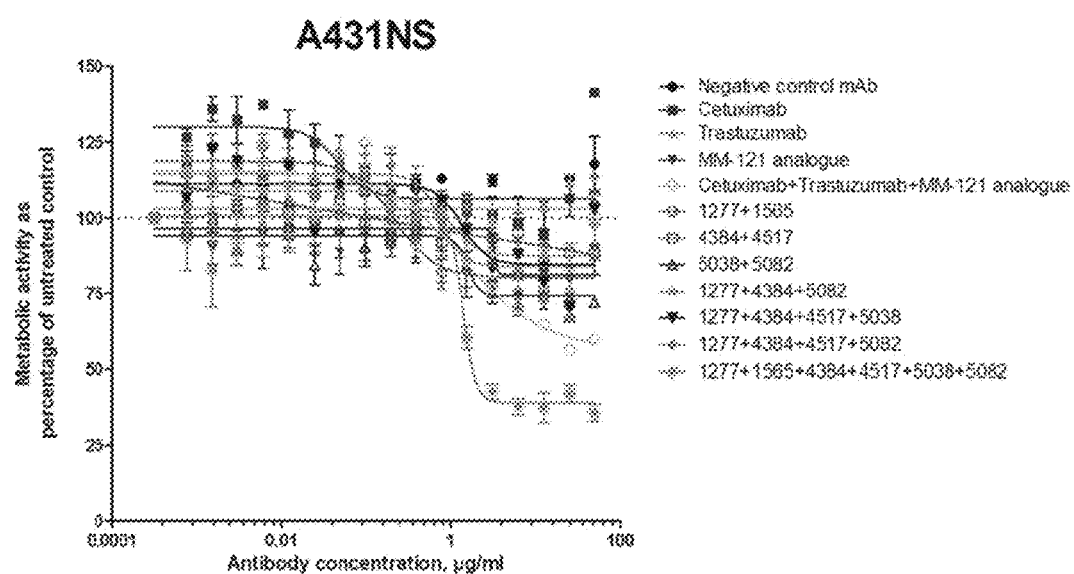
Figure 20:
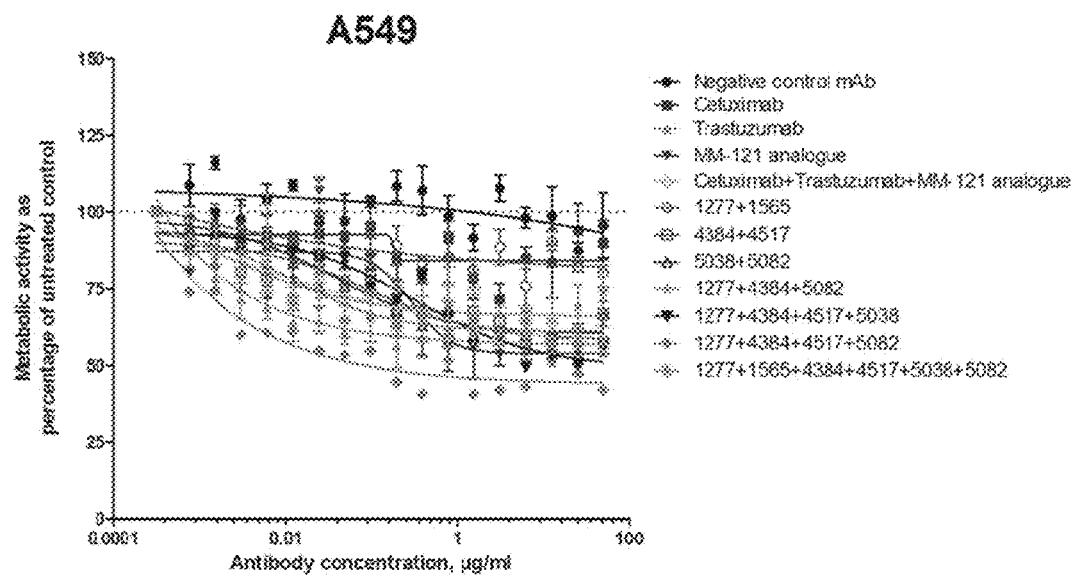
Figure 21:
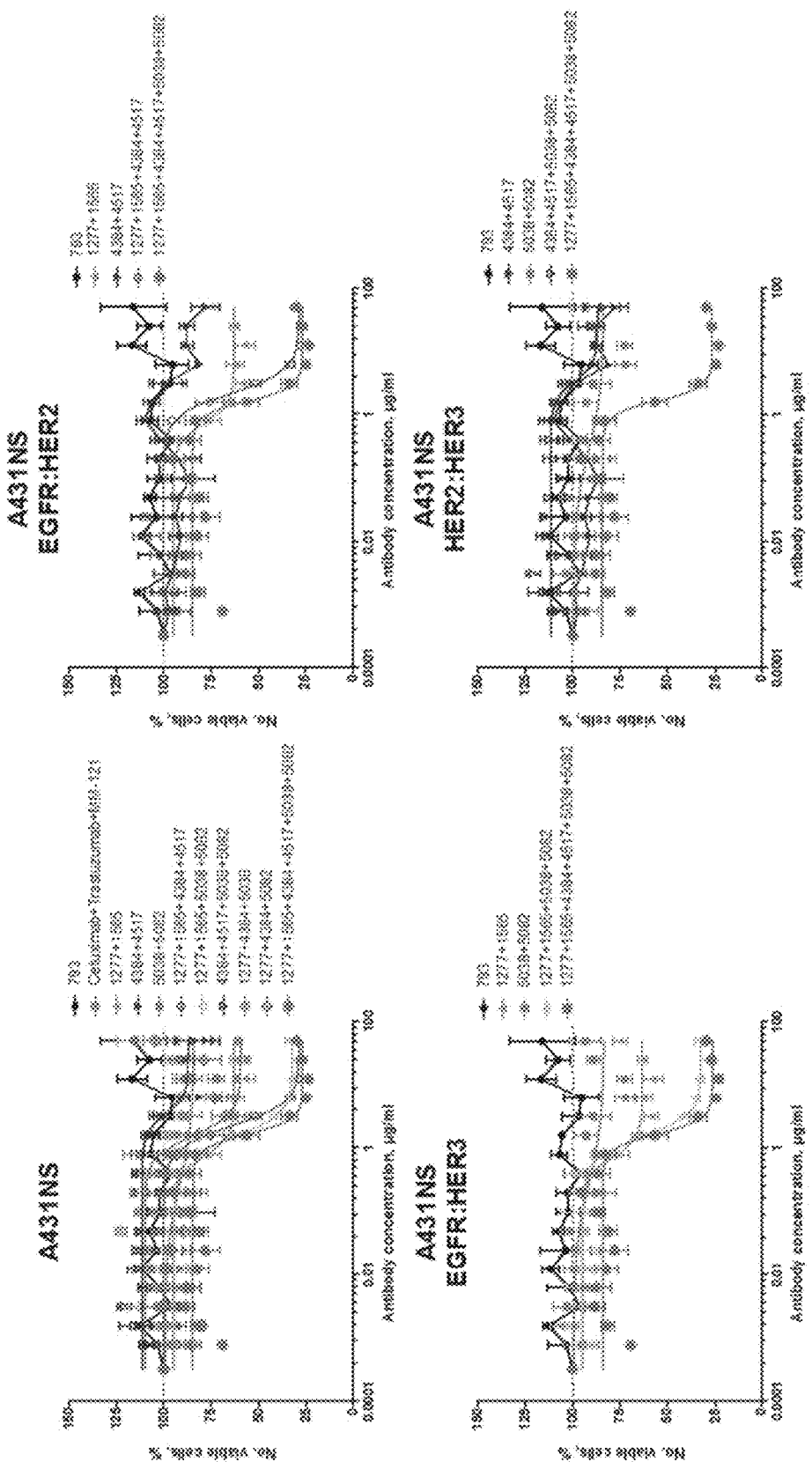
FIGS. 21-25: Titrations showing the effect of different antibody mixtures and antibodies on growth and proliferation of the cancer cell lines A431NS, H1975, HCC202, AU565, and H358.
Figure 22:
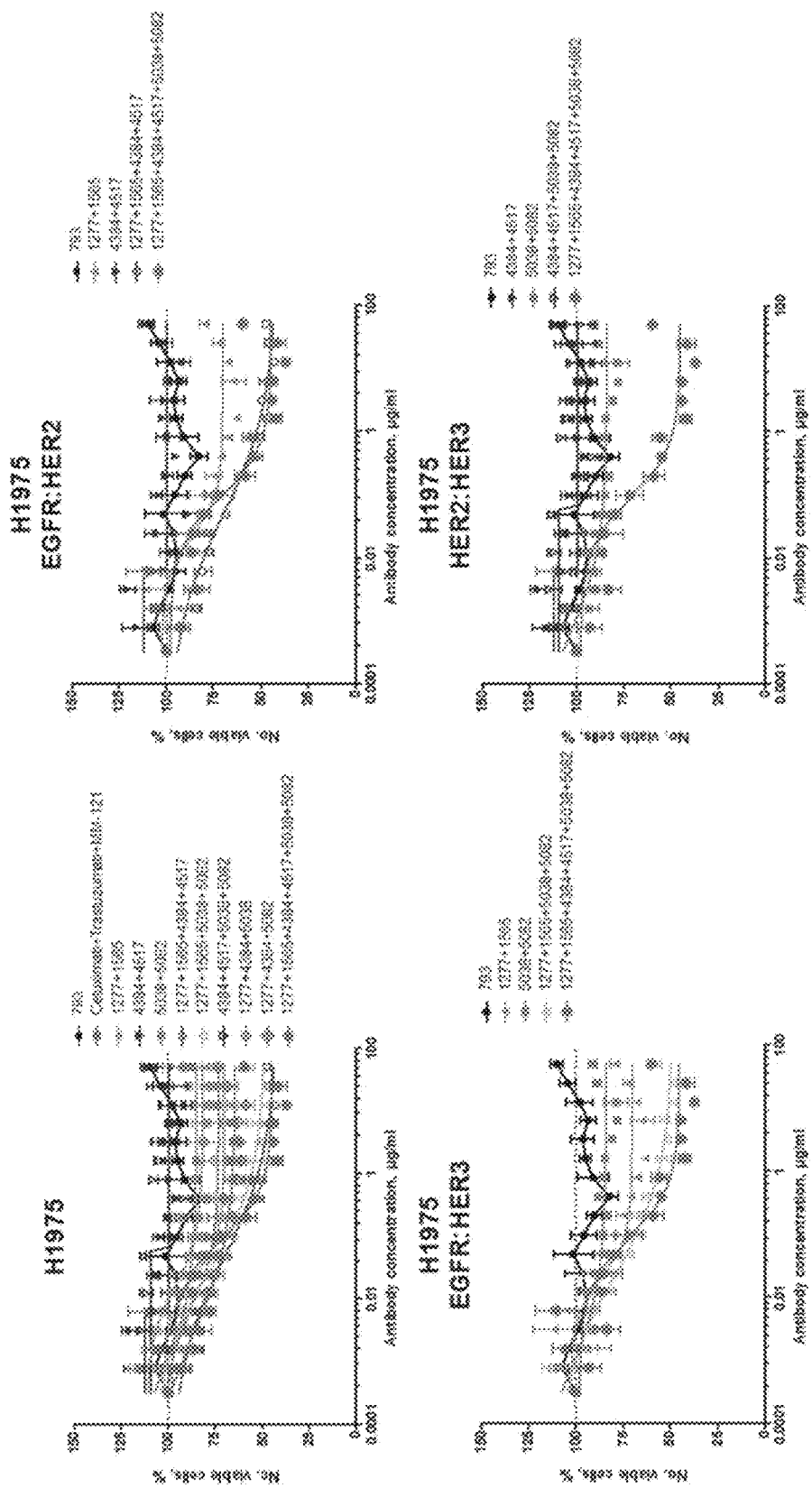
Figure 23:
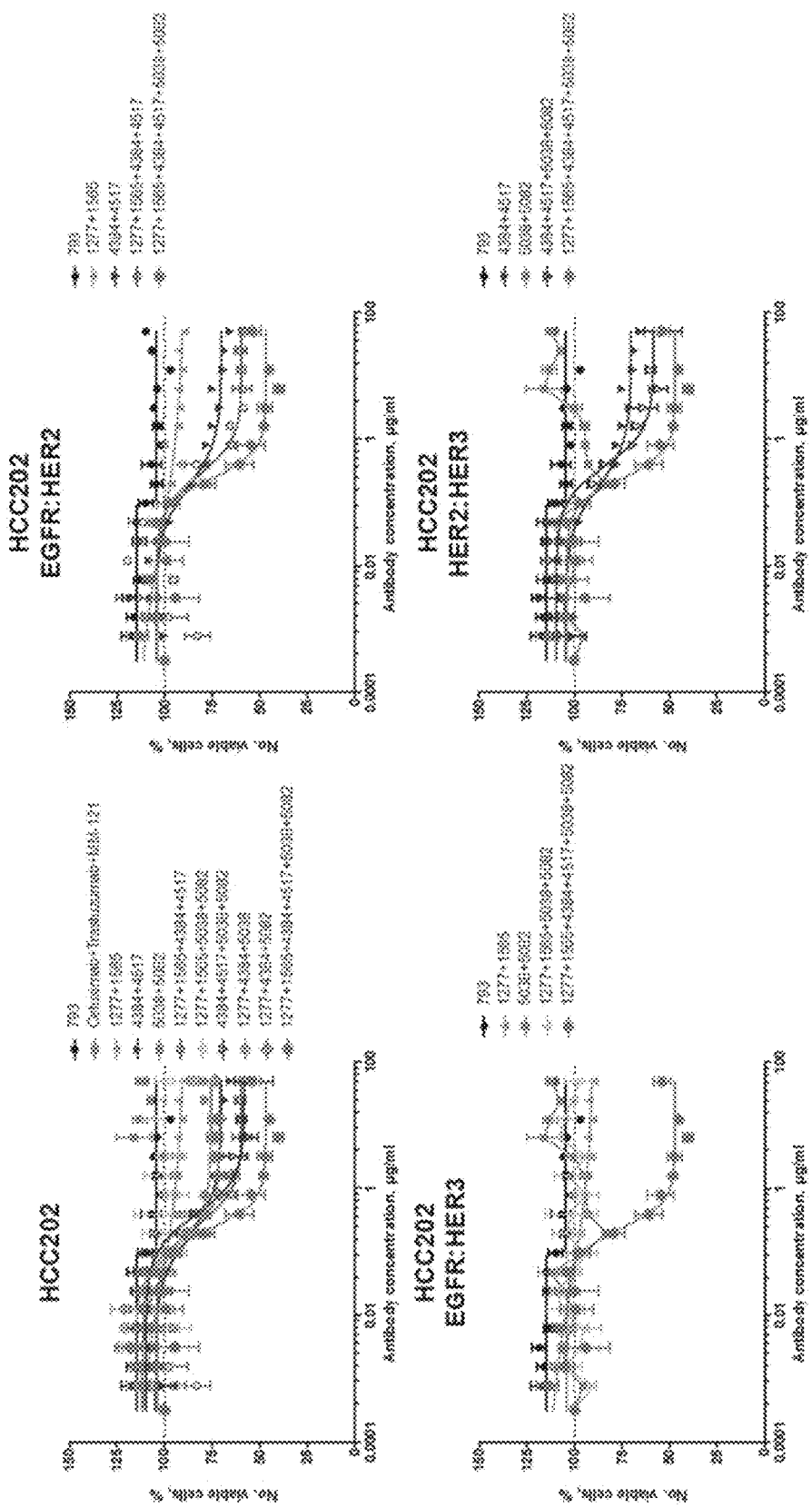
Figure 24:
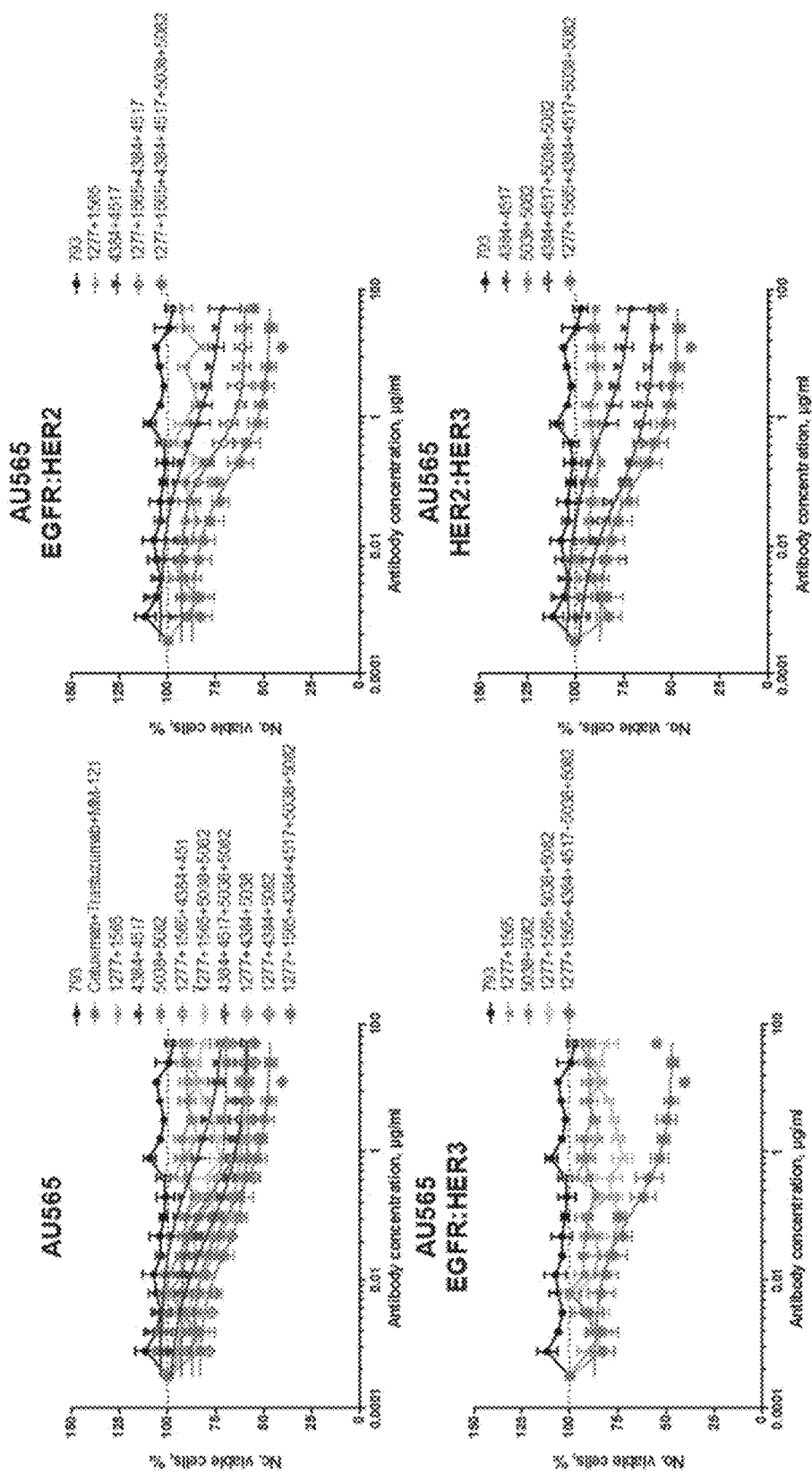
Figure 25:
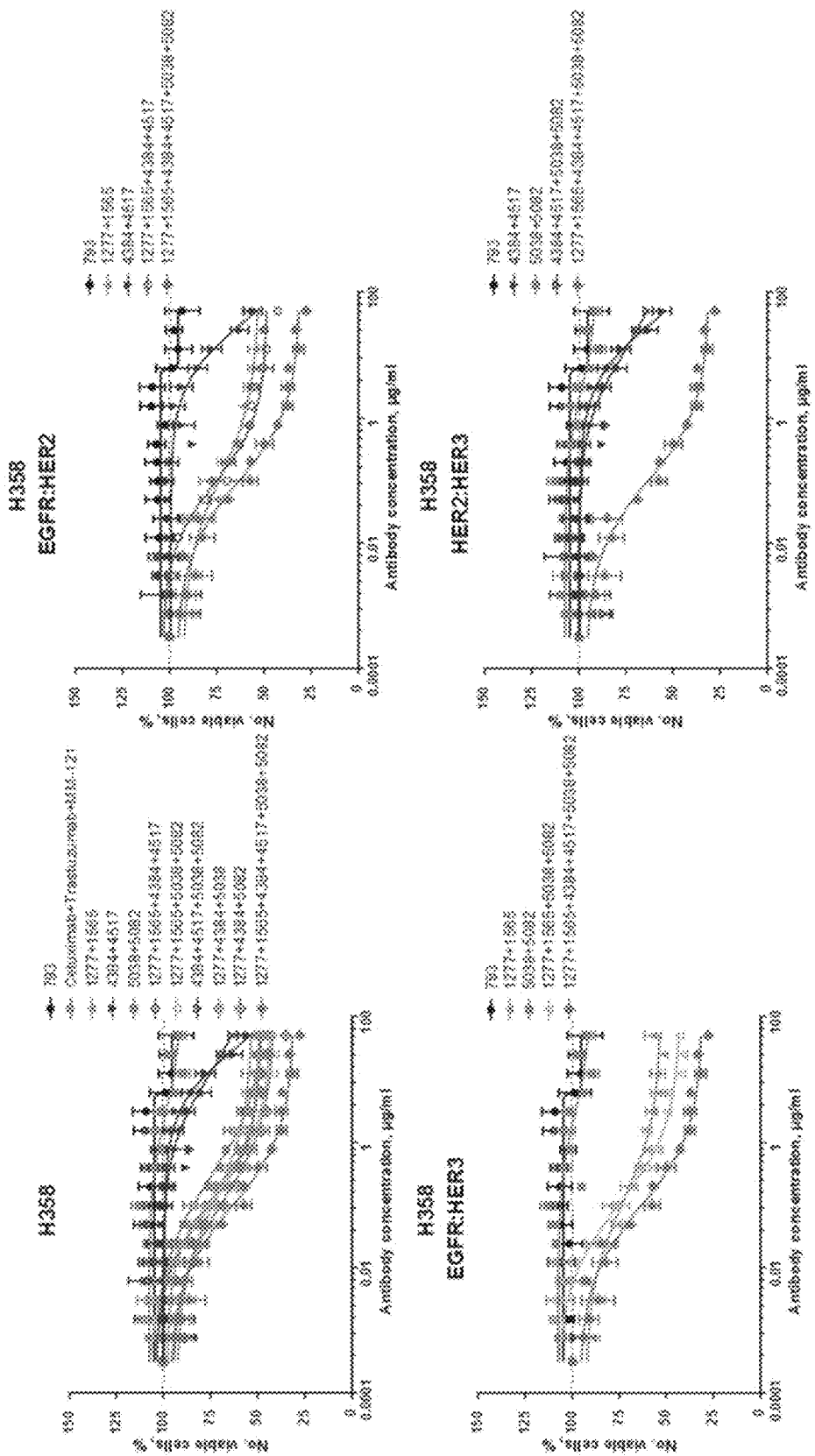

To investigate the level of EGFR, HER2 and HER3 degradation induced by antibody mixtures and combinations of mixtures, Western Blot analysis were performed on whole cell lysates of H292 and OVCAR-8 cells treated with antibody for 48 hours. Cells were grown in T-75 culture flasks and when 50% confluent the culture media were removed, the cells washed in 1×PBS and treated with 20 µg/ml of the antibodies diluted in 5 ml medium containing 0.5% FBS. Cells were treated for 48 hours after which whole cell lysates were prepared using standard RI PA buffer. The total protein concentration was determined in each sample and 1-10 µg protein analyzed by western blotting using primary antibodies against EGFR, HER2 or HER3. An antibody against β-actin was used as loading control.
Results The results from the Western Blot investigation (FIG. 13) shows that mixtures of antibodies against a single receptor (EGFR, HER2 and HER3) induce degradation of their respective target and that a pan-HER mixture consisting of a combination of antibody mixtures against each target is able to induce efficient degradation of all three receptors simultaneously.

In the H292 cell line a small decrease in total EGFR can be observed in cells treated with the anti-EGFR antibodies 1277, 1565 and in the pan-HER mixture consisting of one antibody against each of EGFR, HER2 and HER3 (1277+ 4384+5082), but not in cells treated with the anti-EGFR comparator antibody cetuximab. A mixture of 1277+1565 results in efficient degradation of EGFR, which is also observed with the pan-HER mixture consisting of two antibodies against each target (1277+1565+4384+4517+ 5038+5082). A combination of anti-HER2 antibodies (4384+4517) induced degradation of HER2 both alone and as part of the pan-HER mixture 1277+1565+4384+4517+ 5038+5082.

Like in H292, a small decrease in total EGFR in the OVCAR-8 lysates is observed in cells treated with the individual antibodies 1277 and 1565 and the pan-HER mixture 1277+4384+5082. The combination 1277+1565 and the pan-HER mixture 1277+1565+4384+4517+5038+5082 induced very efficient degradation of EGFR. Anti-HER2 monoclonal antibodies had a minute effect on total HER2 whereas combinations of antibodies against HER2 (4384+ 4517) resulted in efficient degradation of the receptor. Antibodies and antibody mixtures against HER3 all resulted in degradation of the receptor in OVCAR-8 cells.

In H292 cells, an up-regulation of HER2 can be observed in response to treating the cells with individual antibodies (cetuximab, 1277 and 1565) or a mixture of antibodies (1277+1565) against EGFR. This is not observed in cells treated with the pan-HER antibody mixture consisting of two antibodies against each target (1277+1565+4384+ 4517+5038+5082) as the EGFR, HER2 and HER3 are all simultaneously degraded in this setting. In OVCAR-8 cells an up-regulation of HER2 in cells treated with antibodies or mixtures of antibodies against HER3 can be seen. Again, this is not observed in cells treated with the pan-HER antibody mixture consisting of two antibodies against each target (1277+1565+4384+4517+5038+5082) due to simultaneous receptor degradation. Receptor up-regulation was not observed in cells treated with the pan-HER antibody mixture (1277+4384+5082) either. Thus, treating cells with a pan-HER mixture potentially prevents the emergence of resistance as a result of receptor up-regulation since all three receptors (EGFR, HER2 and HER3) are degraded upon treatment with the pan-HER antibody mixture.

Example 8

Cancer Inhibitory Activity of Pan-HER Antibody Mixtures

This example describes the superior cancer inhibitory activity of pan-HER antibody mixtures consisting of one antibody against each of the targets EGFR, HER2 and HER3 i.e. a pan-HER mixture containing one antibody against each target, of pan-HER mixtures containing one antibody against two targets (EGFR and HER3) and two antibodies against one target (HER2) and of a pan-HER mixture consisting of two antibodies against each receptor i.e. EGFR, HER2 and HER3.

Methods

Using the methods described in Example 3 the antibody mixtures against each receptor 1277+1565 (anti-EGFR), 4384+4517 (anti-HER2) and 5038+5082 (anti-HER3), a pan-HER mixture with two antibodies against each receptor (1277+1565+4384+4517+5038+5082), pan-HER mixtures including one antibody against EGFR, two antibodies against HER2 and one antibody against HER3 (1277+4384+4517+5038 or 1277+4384+4517+5082), pan-HER mixtures consisting of one antibody against each receptor (1277+4384+5038 and 1277+4384+5082), the reference antibodies cetuximab (anti-EGFR), trastuzumab (anti-HER2), MM-121 analogue (anti-HER3), a mixture of the three reference antibodies and a negative control antibody were tested for the ability to inhibit the growth and proliferation of 11 cancer cell lines that are dependent on EGFR or HER2, EGFR/HER2, EGFR/HER3, HER2/HER3 or EGFR/HER2/HER3. The results of titrating antibody mixtures and antibodies listed above in the seven cell lines A431NS, N87, A549, OE19, BT474, MDA-MB-175 VII and HCC202 are shown in FIGS. 14-20.

Results

The results presented in FIGS. 14-20 show that although the effect of the antibody mixtures and individual antibodies varies between the different cell lines, the pan-HER antibody mixtures comprised of three, four or six antibodies against the three receptors EGFR, HER2 and HER3 are generally very efficacious at inhibiting cancer cell growth and proliferation. As described in Example 5, the pan-HER mixture containing six antibodies i.e., two antibodies against each of the three receptors is generally the most efficacious across the tested cell lines.

Example 9

Cancer Inhibitory Activity of Pan-HER Antibody Mixtures

This example describes that targeting of three HER family receptors (EGFR/HER2/HER3) simultaneously with a combination of antibody mixtures results in a broader inhibitory profile compared to targeting of two HER family receptors (EGFR/HER2, EGFR/HER3 or HER2/HER3) at the same time or targeting either of the three receptors alone.

Methods

Using the methods described in Example 3 the antibody mixtures against each receptor 1277+1565 (anti-EGFR), 4384+4517 (anti-HER2) and 5038+5082 (anti-HER3), all possible permutation of these i.e. 1277+1565+4384+4517 (anti-EGFR+anti-HER2), 1277+1565+5038+5082 (anti-EGFR+anti-HER2) and 4384+4517+5038+5082 (anti-HER2+antiHER3), a pan-HER mixture with two antibodies against each receptor (1277+1565+4384+4517+5038+5082), pan-HER mixtures consisting of one antibody against each receptor (1277+4384+5038 and 1277+4384+5082), the reference antibodies cetuximab (anti-EGFR), trastuzumab (anti-HER2), MM-121 analogue (anti-HER3), a mixture of the three reference antibodies and a negative control antibody were tested for their ability to inhibit the growth and proliferation of 11 cancer cell lines that are dependent on EGFR or HER2, EGFR/HER2, EGFR/HER3, HER2/HER3 or EGFR/HER2/HER3. The results of titrating the antibody mixtures and antibodies listed above against the five cell lines A431NS, AU565, H358, H1975 and HCC202 are shown in FIGS. 21-25.

Results

In A431NS combinations of mixtures against EGFR and HER2 or EGFR and HER3 result in a synergistic increase in the inhibition of cancer cell growth concurrent with the results described in Example 3. A combination of mixtures targeting HER2 and HER3 had no inhibitory effect on the A431NS cells. A combination of antibody mixtures against EGFR, HER2 and HER3 was superior to individual mixtures and to antibody mixtures with only one antibody against each of the three receptors and as effective as combinations of mixtures against two receptors.

Similar results were obtained with the H1975 cell line. Again, combinations of antibody mixtures against EGFR and HER2 or EGFR and HER3 showed a synergistic increase in inhibitory effect. A combination of antibody mixtures against EGFR, HER2 and HER3 was superior to individual mixtures and to antibody mixtures with only one antibody against each of the three receptors and as effective as combinations of mixtures against two receptors.

In the HCC202 cell line combinations of mixtures against HER2 and EGFR or HER2 and HER3 had an increased inhibitory effect on cancer cell growth and proliferation. A combination of antibody mixtures against EGFR and HER3 had no inhibitory effect on the HCC202 cells. A combination of antibody mixtures against EGFR, HER2 and HER3 was superior to individual mixtures, to combinations of mixtures against two receptors and to antibody mixtures with only one antibody against each of the three receptors.

Similar results were found in the AU565 cell line. Combinations of mixtures against HER2 and EGFR or HER2 and HER3 had an increased inhibitory effect on cancer cell growth and proliferation. A combination of antibody mixtures against EGFR and HER3 had no inhibitory effect on the AU565 cells. A combination of antibody mixtures against EGFR, HER2 and HER3 was superior to individual mixtures, to combinations of mixtures against two receptors and to antibody mixtures with only one antibody against each of the three receptors.

In the H358 cell line combinations of mixtures against EGFR and HER3 or EGFR and HER2 resulted in a small increase in the inhibitory effect compared to targeting EGFR alone. Targeting HER2 and HER3 with a combination of mixtures resulted in a modest inhibitory effect on cancer cell growth and proliferation comparable to targeting HER3 alone. However, combinations of mixtures against all three receptors resulted in an increased inhibition of the cell growth and proliferation, which was superior to individual mixtures, to combinations of mixtures against two receptors and to antibody mixtures with only one antibody against each of the three receptors.

In summary, the results presented in this example demonstrate that the optimal targeting of more than one receptor in the HER family is obtained by combining mixtures of antibodies against each receptor, that targeting of three receptors is superior to targeting of two receptors, and that targeting of each receptor with a mixture of antibodies is superior to targeting of each receptor with a single antibody.

Example 10

Figure 26:
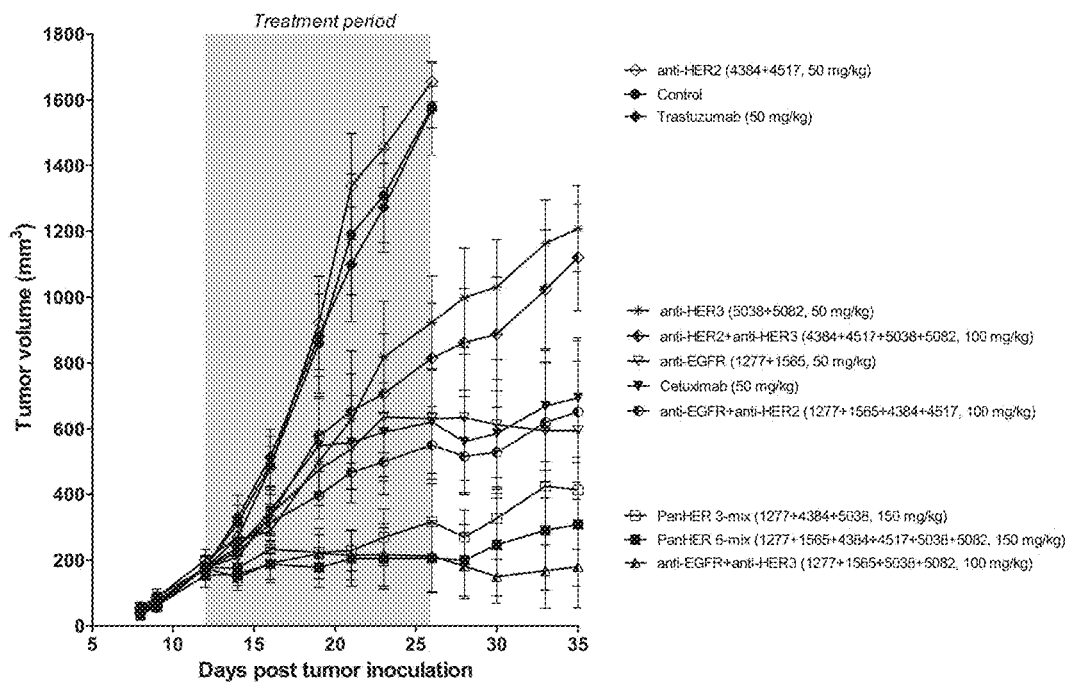
FIG. 26: Growth inhibitory effect of different antibody mixtures and antibodies in A431 NS human tumor xenograft model.

In Vivo Efficacy of Pan-HER Antibody Mixtures in the Human A431NS Tumor Xenograft Model To evaluate the in vivo efficacy of antibody mixtures against EGFR, HER2, HER3 and combinations of the three receptors, we tested the antibodies and mixtures in the A431NS human tumor xenograft model. The human epidermal carcinoma cell line A431 that over-expresses EGFR is used extensively when testing the growth inhibitory effects of novel anti-EGFR compounds both in vitro and in vivo. In the in vivo studies presented here we have used a more aggressively growing variant, A431NS (ATCC no. CRL-2592), of the parent A431 cell line. The results are shown in FIG. 26.

Method $2 \times 10^6$ A431 NS cells were inoculated subcutaneously into the left flank of eight-week old female athymic nude mice. Tumors were measured twice weekly with calipers and tumor volume in $mm^3$ was calculated according to the formula: $(width)^2 \times length \times 0.5$. At an average tumor size of 175 $mm^3$ the mice were randomized and treatment initiated. The mice were treated with twice weekly intraperitoneal injections of 50 mg/kg/target for 2.5 weeks (5 injections in total) followed by an observation period. Thus targeting of one receptor resulted in administration of 50 mg/kg, whereas mice treated with an antibody combination targeting two or three receptors were dosed with 100 or 150 mg/kg, respectively. The following antibody combinations were included in the experiment: 1277+1565 (anti-EGFR), 4384+4517 (anti-HER2), 5038+5082 (anti-HER3), 1277+1565+4384+4517 (anti-EGFR+anti-HER2), 1277+1565+5038+5082 (anti-EGFR+anti-HER3), 4384+4517+5038+5082 (anti-HER2+anti-HER3), 1277+4384+5038 (anti-EGFR+anti-HER2+anti-HER3) and 1277+1565+4384+4517+5038+5082 (anti-EGFR+anti-HER2+anti-HER3). The experiment also included the anti-EGFR monoclonal antibody cetuximab and the anti-HER2 monoclonal antibody trastuzumab, which were dosed and administered as described for the antibody mixtures above.

Results

On day 12 post-inoculation at an average tumor size of 175 $mm^3$ the mice were randomized into 11 groups of eight animals and treatment was initiated. Animals treated with antibodies targeting EGFR+HER3 (1277+1565+5038+5082) and EGFR+HER2+HER3 (Pan-HER mixture: 1277+4384+5038 and Pan-HER mixture: 1277+1565+4384+4517+5038+5082) were very efficient at controlling tumor growth. Almost no gain in tumor size was observed in the treatment period in groups treated with anti-EGFR+anti-HER3 (1277+1565+5038+5082) and anti-EGFR+anti-HER2+anti-HER3 (Pan-HER mixture: 1277+4384+5038 and Pan-HER mixture: 1277+1565+4384+4517+5038+5082). Animals treated with antibodies towards EGFR (1277+1565) or HER3 (5038+5082) or combinations targeting EGFR+HER2 (1277+1565+4384+4517) and HER2+HER3 (4384+4517+5038+5082) all had continued tumor growth in the treatment period although tumors grew at a slower rate compared to the vehicle control. Animals treated with anti-HER3 and anti-HER2+anti-HER3 antibody combinations had only marginally smaller tumors compared to the vehicle control group. The groups treated with anti-EGFR (1277+1565) or anti-EGFR+anti-HER2 (1277+1565+4384+4517) showed tumor inhibition and a slower growth rate compared to the vehicle control.

In the observation period, groups treated with anti-HER3, anti-EGFR+anti-HER2, anti-HER2+anti-HER3 and cetuximab all had continued tumor growth although at a slower pace compared to the vehicle control group. In general, groups treated with anti-EGFR antibodies and mixtures including antibody combinations against EGFR had a slower tumor growth rate compared to groups treated with antibody mixtures against HER3 or combinations of mixtures against HER2+HER3.

Groups treated with combinations of antibody mixtures targeting EGFR+HER3 and EGFR+HER2+HER3 (Pan-HER 6-mix) and a combination of one antibody against each of the three receptors (PanHER 3-mix) all maintained control of tumor growth throughout the experiment.

The enhanced efficacy of simultaneous targeting of EGFR and HER3 in the A431NS tumor xenografts model reflects the ErbB receptor dependencies known for this cell line from in vitro experiments (Example 2). Although primarily dependent on EGFR signaling, the A431NS cell line is also dependent on the cross-talk between EGFR and HER3 and to some extent between EGFR and HER2, although the latter is not observed in the current in vivo experiment.

In summary, the results presented in this experiment shows that treating A431NS tumor xenografts with a combination of antibodies or antibody mixtures against EGFR+HER3 or EGFR+HER2+HER3 is more effective compared to targeting the tumors with monoclonal antibodies and antibody mixtures against the individual targets EGFR, HER2 and HER3, or combinations of monoclonal antibodies and antibody mixtures against EGFR+HER2 or HER2+HER3.

The invention claimed is:

1. A method of producing an antibody composition, wherein said method comprises the steps of:
  a) providing a host cell capable of expressing an anti-EGFR antibody molecule, a host cell capable of expressing an anti-HER2 antibody molecule, and a host cell capable of expressing an anti-HER3 antibody molecule, wherein:
    i) the anti-EGFR antibody molecule comprises the $V_H$ and $V_L$ amino acid sequences in SEQ ID NOs: 18 and 20, respectively, or in SEQ ID NOs: 22 and 24, respectively; or a humanized variant thereof;
    ii) the anti-HER2 antibody molecule comprises the $V_H$ and $V_L$ amino acid sequences in SEQ ID NOs: 30 and 32, respectively, or in SEQ ID NOs: 38 and 40, respectively; or a humanized variant thereof; and
    iii) the anti-HER3 antibody molecule comprises the $V_H$ and $V_L$ amino acid sequences in SEQ ID NOs: 50 and 52, respectively, or in SEQ ID NOs: 54 and 56, respectively; or a humanized variant thereof;
  b) cultivating said host cells under conditions suitable for expression of the antibody molecules;
  c) isolating the resulting antibody molecules; and
  d) admixing the isolated antibody molecules, thereby producing the antibody composition.

2. The method of claim 1, wherein at least one of said antibody molecules is a chimeric or humanized antibody, and comprises a human $IgG_1$ or $IgG_2$ heavy chain constant domain.

3. The method of claim 1, wherein the method further comprises the step of conjugating an anti-cancer agent to at least one of said isolated antibody molecules to produce an immunoconjugate prior to admixture.

4. The method of claim 1, wherein said method comprises the steps of:
  a) providing a host cell capable of expressing a first anti-EGFR antibody molecule and a host cell capable of expressing a second, distinct anti-EGFR antibody molecule; a host cell capable of expressing a first anti-HER2 antibody molecule and a host cell capable of expressing a second, distinct anti-HER2 antibody molecule; and a host cell capable of expressing a first anti-HER3 antibody molecule and a host cell capable of expressing a second, distinct anti-HER3 antibody molecule, wherein:
    i) said first anti-EGFR antibody molecule comprises the heavy and light chain CDR1-3 in SEQ ID NOs: 18 and 20, respectively;
    ii) said second anti-EGFR antibody molecule comprises the heavy and light chain CDR1-3 in SEQ ID NOs: 22 and 24, respectively;
    iii) said first anti-HER2 antibody molecule comprises the heavy and light chain CDR1-3 in SEQ ID NOs: 30 and 32, respectively;
    iv) said second anti-HER2 antibody molecule comprises the heavy and light chain CDR1-3 in SEQ ID NOs: 38 and 40, respectively;
    v) said first anti-HER3 antibody molecule comprises the heavy and light chain CDR1-3 in SEQ ID NOs: 50 and 52, respectively; and
    vi) said second anti-HER3 antibody molecule comprises the heavy and light chain CDR1-3 in SEQ ID NOs: 54 and 56, respectively;
  b) cultivating said host cells under conditions suitable for expression of the antibody molecules;
  c) isolating the resulting antibody molecules; and
  d) admixing the isolated antibody molecules, thereby producing the antibody composition.

5. The method of claim 4, wherein:
  a) said first anti-EGFR antibody molecule comprises the $V_H$ and $V_L$ amino acid sequences in SEQ ID NOs: 18 and 20, respectively;
  b) said second anti-EGFR antibody molecule comprises the $V_H$ and $V_L$ amino acid sequences in SEQ ID NOs: 22 and 24, respectively;
  c) said first anti-HER2 antibody molecule comprises the $V_H$ and $V_L$ amino acid sequences in SEQ ID NOs: 30 and 32, respectively;
  d) said second anti-HER2 antibody molecule comprises the $V_H$ and $V_L$ amino acid sequences in SEQ ID NOs: 38 and 40, respectively;
  e) said first anti-HER3 antibody molecule comprises the $V_H$ and $V_L$ amino acid sequences in SEQ ID NOs: 50 and 52, respectively; and
  f) said second anti-HER3 antibody molecule comprises the $V_H$ and $V_L$ amino acid sequences in SEQ ID NOs: 54 and 56, respectively.

6. The method of claim 4, wherein at least one of said antibody molecules is a chimeric or humanized antibody, and comprises a human $IgG_1$ or $IgG_2$ heavy chain constant domain.

7. The method of claim 4, wherein the method further comprises the step of conjugating an anti-cancer agent to at least one of said isolated antibody molecules to produce an immunoconjugate prior to admixture.

8. A method for producing an antibody composition, the method comprising:
  a) providing
    i) a host cell capable of expressing an anti-EGFR antibody molecule comprising (1) the heavy chain variable domain ($V_H$) amino acid sequence in SEQ ID NO: 18 and a human $IgG_1$ heavy chain constant domain, and (2) the light chain (LC) amino acid sequence in SEQ ID NO: 20;
    ii) a host cell capable of expressing an anti-EGFR antibody molecule comprising (1) the $V_H$ amino acid sequence in SEQ ID NO: 22 and a human $IgG_1$ heavy chain constant domain, and (2) the LC amino acid sequence in SEQ ID NO: 24;
    iii) a host cell capable of expressing an anti-HER2 antibody molecule comprising (1) the $V_H$ amino acid sequence in SEQ ID NO: 30 and a human $IgG_1$ heavy chain constant domain, and (2) the LC amino acid sequence in SEQ ID NO: 32;
    iv) a host cell capable of expressing an anti-HER2 antibody molecule comprising (1) the $V_H$ amino acid sequence in SEQ ID NO: 38 and a human $IgG_1$ heavy chain constant domain, and (2) the LC amino acid sequence in SEQ ID NO: 40;
    v) a host cell capable of expressing an anti-HER3 antibody molecule comprising (1) the $V_H$ amino acid sequence in SEQ ID NO: 50 and a human $IgG_1$ heavy chain constant domain, and (2) the LC amino acid sequence in SEQ ID NO: 52; and
    vi) a host cell capable of expressing an anti-HER3 antibody molecule comprising (1) the $V_H$ amino acid sequence in SEQ ID NO: 54 and a human $IgG_1$ heavy chain constant domain, and (2) the LC amino acid sequence in SEQ ID NO: 56;
  b) cultivating said host cells under conditions suitable for expression of the antibody molecules;
  c) isolating the resulting antibody molecules; and
  d) admixing the isolated antibody molecules, thereby producing the antibody composition.

* * * * *

UNITED STATES PATENT AND TRADEMARK OFFICE
CERTIFICATE OF CORRECTION

PATENT NO. : 10,221,246 B2
APPLICATION NO. : 15/361571
DATED : March 5, 2019
INVENTOR(S) : Mikkel Wandahl Pedersen et al.

Page 1 of 1

It is certified that error appears in the above-identified patent and that said Letters Patent is hereby corrected as shown below:

On the Title Page

Item (30), under "Foreign Application Priority Data," please change "PA 2011 00675" to --PA 2011 00672--.

Signed and Sealed this
Fourth Day of June, 2019

Andrei Iancu
*Director of the United States Patent and Trademark Office*

SEQUENCE LISTING

```
<160> NUMBER OF SEQ ID NOS: 150

<210> SEQ ID NO 1
<211> LENGTH: 372
<212> TYPE: DNA
<213> ORGANISM: Mus musculus

<400> SEQUENCE: 1
cgcgccgagg tccaactgca gcaacctggg tctgagctgg tgaggcctgg agcttcagtg      60
aagctgtcct gcaaggcttc tggctacaca ttcaccagct actggatgca ctgggtgaag     120
```

-continued

```
cagaggcctg acaaggcct tgagtggatt gggaatattt atcctggtag tcgtagtact      180
aactacgatg agaagttcaa gagcaaggcc acactgactg tagacacatc ctccagcaca      240
gcctacatgc agctcagcag cctgacatct gaggactctg cggtctatta ctgtacaaga      300
aatggggatt actacgttag tagcggggat gctatggact actggggtca aggaacctca      360
gtcaccgtct cg                                                          372
```

<210> SEQ ID NO 2
<211> LENGTH: 124
<212> TYPE: PRT
<213> ORGANISM: Mus musculus

<400> SEQUENCE: 2

```
Arg Ala Glu Val Gln Leu Gln Gln Pro Gly Ser Glu Leu Val Arg Pro
1               5                   10                  15

Gly Ala Ser Val Lys Leu Ser Cys Lys Ala Ser Gly Tyr Thr Phe Thr
            20                  25                  30

Ser Tyr Trp Met His Trp Val Lys Gln Arg Pro Gly Gln Gly Leu Glu
        35                  40                  45

Trp Ile Gly Asn Ile Tyr Pro Gly Ser Arg Ser Thr Asn Tyr Asp Glu
    50                  55                  60

Lys Phe Lys Ser Lys Ala Thr Leu Thr Val Asp Thr Ser Ser Ser Thr
65                  70                  75                  80

Ala Tyr Met Gln Leu Ser Ser Leu Thr Ser Glu Asp Ser Ala Val Tyr
                85                  90                  95

Tyr Cys Thr Arg Asn Gly Asp Tyr Tyr Val Ser Ser Gly Asp Ala Met
            100                 105                 110

Asp Tyr Trp Gly Gln Gly Thr Ser Val Thr Val Ser
        115                 120
```

<210> SEQ ID NO 3
<211> LENGTH: 648
<212> TYPE: DNA
<213> ORGANISM: Mus musculus

<400> SEQUENCE: 3

```
ctagccgaca ttcagatgac tcagactaca tcctccctgt ctgcctctct gggagacaga      60
gtcaccatca gttgcaggac aagtcaggac attggcaatt atttaaactg gtatcagcag     120
aaaccagatg gaactgttaa actcctgatc tactacacat caagattaca ctcaggagtc     180
ccatcaaggt tcagtggcag tgggtctgga acagattttt ctctcaccat taacaacgtg     240
gagcaagagg atgttgccac ttacttttgc caacactata atacggttcc tcgacgttc      300 ggtggaggca ccaagctgga aatcaaacga actgtggctg caccatctgt cttcatcttc     360
ccgccatctg atgagcagtt gaaatctgga actgcctctg ttgtgtgcct gctgaataac     420
ttctatccca gagaggccaa agtacagtgg aaggtggata cgcccctcca atcgggtaac     480
tcccaggaga gtgtcacaga gcaggacagc aaggacagca cctacagcct cagcagcacc     540
ctgacgctga gcaaagcaga ctacgagaaa cacaaagtct acgcctgcga agtcacccat     600
cagggcctga gctcgcccgt cacaaagagc ttcaacaggg gagagtgt                  648
```

<210> SEQ ID NO 4
<211> LENGTH: 216
<212> TYPE: PRT
<213> ORGANISM: Mus musculus

```
<400> SEQUENCE: 4

Leu Ala Asp Ile Gln Met Thr Gln Thr Thr Ser Ser Leu Ser Ala Ser
1               5                   10                  15

Leu Gly Asp Arg Val Thr Ile Ser Cys Arg Thr Ser Gln Asp Ile Gly
            20                  25                  30

Asn Tyr Leu Asn Trp Tyr Gln Gln Lys Pro Asp Gly Thr Val Lys Leu
        35                  40                  45

Leu Ile Tyr Tyr Thr Ser Arg Leu His Ser Gly Val Pro Ser Arg Phe
    50                  55                  60

Ser Gly Ser Gly Ser Gly Thr Asp Phe Ser Leu Thr Ile Asn Asn Val
65                  70                  75                  80

Glu Gln Glu Asp Val Ala Thr Tyr Phe Cys Gln His Tyr Asn Thr Val
                85                  90                  95

Pro Pro Thr Phe Gly Gly Gly Thr Lys Leu Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 5
<211> LENGTH: 360
<212> TYPE: DNA
<213> ORGANISM: Mus musculus

<400> SEQUENCE: 5
cgcgcccagg tccaactgca gcagcctggg gctgaactgg tggagcctgg gggttcagtg      60
aagctgtcct gcaaggcttc tggctacacc ttcaccagtc actggatgca ctgggtgaag     120
cagaggcctg acaaggcct tgagtggata ggtgagatta atcctagcag cggtcgtaat     180
aactacaatg agaagttcaa gagtaaggcc acactgactg tagacaaatc ctccagcaca     240
gcctacatgc aattcagcag cctgacatct gaggactctg cggtctatta ttgtgtaaga     300
tactatggtt acgacgaagc tatggactac tggggtcaag aacctcagt caccgtctcg     360

<210> SEQ ID NO 6
<211> LENGTH: 120
<212> TYPE: PRT
<213> ORGANISM: Mus musculus

<400> SEQUENCE: 6

Arg Ala Gln Val Gln Leu Gln Gln Pro Gly Ala Glu Leu Val Glu Pro
1               5                   10                  15

Gly Gly Ser Val Lys Leu Ser Cys Lys Ala Ser Gly Tyr Thr Phe Thr
            20                  25                  30

Ser His Trp Met His Trp Val Lys Gln Arg Pro Gly Gln Gly Leu Glu
```

```
                35                  40                  45
Trp Ile Gly Glu Ile Asn Pro Ser Ser Gly Arg Asn Asn Tyr Asn Glu
 50                  55                  60
Lys Phe Lys Ser Lys Ala Thr Leu Thr Val Asp Lys Ser Ser Ser Thr
 65                  70                  75                  80
Ala Tyr Met Gln Phe Ser Ser Leu Thr Ser Glu Asp Ser Ala Val Tyr
                 85                  90                  95
Tyr Cys Val Arg Tyr Tyr Gly Tyr Asp Glu Ala Met Asp Tyr Trp Gly
            100                 105                 110
Gln Gly Thr Ser Val Thr Val Ser
            115                 120

<210> SEQ ID NO 7
<211> LENGTH: 663
<212> TYPE: DNA
<213> ORGANISM: Mus musculus

<400> SEQUENCE: 7
ctagccgaca tcgtgatgac acaagctgca ttctccaatc cagtcactct tggaacatca       60
gcttccatct cctgcaggtc tagtaagagt ctcctacata gtaatggcat cacttatttg      120
tattggtatc tgcagaagcc aggccagtct cctcagctcc tgatttatca gatgtccaac      180
cttgcctcag gagtcccaga caggttcagt agcagtgggt caggaactga tttcacactg      240
agaatcagca gagtggaggc tgaggatgtg gtgtttatt actgtgctca aaatctagaa       300
cttccgtaca cgttcggagg ggggaccaag ctggaaataa aacgaactgt ggctgcacca      360
tctgtcttca tcttcccgcc atctgatgag cagttgaaat ctggaactgc ctctgttgtg      420
tgcctgctga ataacttcta tcccagagag gccaaagtac agtggaaggt ggataacgcc      480
ctccaatcgg gtaactccca ggagagtgtc acagagcagg acagcaagga cagcacctac      540
agcctcagca gcaccctgac gctgagcaaa gcagactacg agaaacacaa agtctacgcc      600
tgcgaagtca cccatcaggg cctgagctcg cccgtcacaa agagcttcaa caggggagag      660
tgt                                                                    663

<210> SEQ ID NO 8
<211> LENGTH: 221
<212> TYPE: PRT
<213> ORGANISM: Mus musculus

<400> SEQUENCE: 8

Leu Ala Asp Ile Val Met Thr Gln Ala Ala Phe Ser Asn Pro Val Thr
  1               5                  10                  15
Leu Gly Thr Ser Ala Ser Ile Ser Cys Arg Ser Ser Lys Ser Leu Leu
                 20                  25                  30
His Ser Asn Gly Ile Thr Tyr Leu Tyr Trp Tyr Leu Gln Lys Pro Gly
             35                  40                  45
Gln Ser Pro Gln Leu Leu Ile Tyr Gln Met Ser Asn Leu Ala Ser Gly
         50                  55                  60
Val Pro Asp Arg Phe Ser Ser Ser Gly Ser Gly Thr Asp Phe Thr Leu
 65                  70                  75                  80
Arg Ile Ser Arg Val Glu Ala Glu Asp Val Gly Val Tyr Tyr Cys Ala
                 85                  90                  95
Gln Asn Leu Glu Leu Pro Tyr Thr Phe Gly Gly Gly Thr Lys Leu Glu
            100                 105                 110
Ile Lys Arg Thr Val Ala Ala Pro Ser Val Phe Ile Phe Pro Pro Ser
```

```
                115               120                 125
Asp Glu Gln Leu Lys Ser Gly Thr Ala Ser Val Val Cys Leu Leu Asn
        130                 135                 140

Asn Phe Tyr Pro Arg Glu Ala Lys Val Gln Trp Lys Val Asp Asn Ala
145                 150                 155                 160

Leu Gln Ser Gly Asn Ser Gln Glu Ser Val Thr Glu Gln Asp Ser Lys
                165                 170                 175

Asp Ser Thr Tyr Ser Leu Ser Ser Thr Leu Thr Leu Ser Lys Ala Asp
                180                 185                 190

Tyr Glu Lys His Lys Val Tyr Ala Cys Glu Val Thr His Gln Gly Leu
                195                 200                 205

Ser Ser Pro Val Thr Lys Ser Phe Asn Arg Gly Glu Cys
        210                 215                 220

<210> SEQ ID NO 9
<211> LENGTH: 360
<212> TYPE: DNA
<213> ORGANISM: Mus musculus

<400> SEQUENCE: 9
cgcgccgaag tgcagctggt ggagtctggg ggaggcttag tgaagcctgg agggtccctg      60
aaactctcct gtgcagcctc tggattcact ttcagtagtt atgccctgtc ttgggttcgc     120
cagactccag agaggaggct ggagtgggtc gcatccatta gtggtgttgg tagcacctac     180
tttccagaca gtgtgaaggg ccgtttcacc atgtccagag ataatgccag gaacatcctg     240
tacctccaaa tgagcagtct gaggtctgag gacacggcca tgtattactg tgcaagaggt     300
tctgatggtt acttctatgc tatggactac tggggtcaag gaacctcagt caccgtctcg     360

<210> SEQ ID NO 10
<211> LENGTH: 120
<212> TYPE: PRT
<213> ORGANISM: Mus musculus

<400> SEQUENCE: 10

Arg Ala Glu Val Gln Leu Val Glu Ser Gly Gly Gly Leu Val Lys Pro
1               5                   10                  15

Gly Gly Ser Leu Lys Leu Ser Cys Ala Ala Ser Gly Phe Thr Phe Ser
                20                  25                  30

Ser Tyr Ala Leu Ser Trp Val Arg Gln Thr Pro Glu Arg Arg Leu Glu
            35                  40                  45

Trp Val Ala Ser Ile Ser Gly Val Gly Ser Thr Tyr Phe Pro Asp Ser
50                  55                  60

Val Lys Gly Arg Phe Thr Met Ser Arg Asp Asn Ala Arg Asn Ile Leu
65                  70                  75                  80

Tyr Leu Gln Met Ser Ser Leu Arg Ser Glu Asp Thr Ala Met Tyr Tyr
                85                  90                  95

Cys Ala Arg Gly Ser Asp Gly Tyr Phe Tyr Ala Met Asp Tyr Trp Gly
            100                 105                 110

Gln Gly Thr Ser Val Thr Val Ser
        115                 120

<210> SEQ ID NO 11
<211> LENGTH: 660
<212> TYPE: DNA
<213> ORGANISM: Mus musculus

<400> SEQUENCE: 11
```

```
ctagccgaca ttgtgctgac tcagtctcct gcttccttag ctgtatctct ggggcagagg    60
gccaccattt catgcagggc cagcaaaagt gtcagtacat ctggctatag ttttatgcac   120
tggtaccaac tgaaaccagg acagccaccc aaactcctca tctatcttgc atccaaccta   180
gaatctgggg tccctgccag gttcagtggc agtgggtctg ggacagactt caccctcaac   240
atccatcctg tggaagagga ggatgctgca acctattact gtcagcacag tagggagttt   300
ccgttaacgt tcggagggggg gaccaagctg gaaataaaac gaactgtggc tgcaccatct   360
gtcttcatct tcccgccatc tgatgagcag ttgaaatctg gaactgcctc tgttgtgtgc   420
ctgctgaata acttctatcc cagagaggcc aaagtacagt ggaaggtgga taacgccctc   480
caatcgggta actcccagga gagtgtcaca gagcaggaca gcaaggacag cacctacagc   540
ctcagcagca ccctgacgct gagcaaagca gactacgaga acacaaaagt ctacgcctgc   600
gaagtcaccc atcagggcct gagctcgccc gtcacaaaga gcttcaacag gggagagtgt   660
```

<210> SEQ ID NO 12
<211> LENGTH: 220
<212> TYPE: PRT
<213> ORGANISM: Mus musculus

<400> SEQUENCE: 12

```
Leu Ala Asp Ile Val Leu Thr Gln Ser Pro Ala Ser Leu Ala Val Ser
1               5                   10                  15

Leu Gly Gln Arg Ala Thr Ile Ser Cys Arg Ala Ser Lys Ser Val Ser
            20                  25                  30

Thr Ser Gly Tyr Ser Phe Met His Trp Tyr Gln Leu Lys Pro Gly Gln
        35                  40                  45

Pro Pro Lys Leu Leu Ile Tyr Leu Ala Ser Asn Leu Glu Ser Gly Val
    50                  55                  60

Pro Ala Arg Phe Ser Gly Ser Gly Ser Gly Thr Asp Phe Thr Leu Asn
65                  70                  75                  80

Ile His Pro Val Glu Glu Asp Ala Ala Thr Tyr Tyr Cys Gln His
                85                  90                  95

Ser Arg Glu Phe Pro Leu Thr Phe Gly Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 13
<211> LENGTH: 366
<212> TYPE: DNA
<213> ORGANISM: Mus musculus

<400> SEQUENCE: 13

```
cgcgccgaag tgcagctggt ggagtctggg ggaggcttag tgaagcctgg agggtccctg      60
aaactctcct gtgcagcctc tggattcgct tacagtacct atgacatgtc ttgggttcgc     120
cagactccgg agaagaggct ggagtgggtc gcatacatta gtagtggtgg tgatgccgcc     180
tactatcccg acactgtgaa ggccgattc accatctcca gagacaatgc caaaaacacc     240
ctatacctgc aaatgagcag tctgaagtct gaggacacag ccatgtatta ctgtgcgagg     300
tctcgctatg gaaactacgg ggacgctatg gactactggg gtcaaggaac ctcagtcacc     360
gtctcg                                                                 366
```

<210> SEQ ID NO 14
<211> LENGTH: 122
<212> TYPE: PRT
<213> ORGANISM: Mus musculus

<400> SEQUENCE: 14

```
Arg Ala Glu Val Gln Leu Val Glu Ser Gly Gly Gly Leu Val Lys Pro
1               5                   10                  15
Gly Gly Ser Leu Lys Leu Ser Cys Ala Ala Ser Gly Phe Ala Tyr Ser
            20                  25                  30
Thr Tyr Asp Met Ser Trp Val Arg Gln Thr Pro Glu Lys Arg Leu Glu
        35                  40                  45
Trp Val Ala Tyr Ile Ser Ser Gly Gly Asp Ala Ala Tyr Tyr Pro Asp
    50                  55                  60
Thr Val Lys Gly Arg Phe Thr Ile Ser Arg Asp Asn Ala Lys Asn Thr
65                  70                  75                  80
Leu Tyr Leu Gln Met Ser Ser Leu Lys Ser Glu Asp Thr Ala Met Tyr
                85                  90                  95
Tyr Cys Ala Arg Ser Arg Tyr Gly Asn Tyr Gly Asp Ala Met Asp Tyr
            100                 105                 110
Trp Gly Gln Gly Thr Ser Val Thr Val Ser
        115                 120
```

<210> SEQ ID NO 15
<211> LENGTH: 660
<212> TYPE: DNA
<213> ORGANISM: Mus musculus

<400> SEQUENCE: 15

```
ctagccgatg ttgtgatgac acagactcca ctctccctgc ctgtcagtct tggagatcaa      60
gcctccatct cttgcagatc tagtcagagc cttgtacaca gtaatggtaa cacctattta     120
cattggtacc tgcagaagcc aggccagtct ccaaagctcc tgctctacaa agtttccaac     180
cgattttctg gggtcccaga caggttcagt ggcagtggat cagggacaga tttcacactc     240
aagatcagca gtggagtc tgaggatctg ggagtttatt tctgctctca aaatacacat     300
gtgtacacgt tcggagggg gacaaagttg gaaataaaac gaactgtggc tgcaccatct     360
gtcttcatct tcccgccatc tgatgagcag ttgaaatctg gaactgcctc tgttgtgtgc     420
ctgctgaata acttctatcc cagagaggcc aaagtacagt ggaaggtgga taacgccctc     480
caatcgggta actcccagga gagtgtcaca gagcaggaca gcaaggacag cacctacagc     540
ctcagcagca cctgacgct gagcaaagca gactacgaga acacaaagt ctacgcctgc     600
gaagtcaccc atcagggcct gagctcgccc gtcacaaaga gcttcaacag gggagagtgt     660
```

```
<210> SEQ ID NO 16
<211> LENGTH: 220
<212> TYPE: PRT
<213> ORGANISM: Mus musculus

<400> SEQUENCE: 16
```

| | | | | | | | | | | | | | | | |
|---|---|---|---|---|---|---|---|---|---|---|---|---|---|---|---|
| Leu | Ala | Asp | Val | Val | Met | Thr | Gln | Thr | Pro | Leu | Ser | Leu | Pro | Val | Ser |
| 1 | | | | 5 | | | | | 10 | | | | | 15 | |
| Leu | Gly | Asp | Gln | Ala | Ser | Ile | Ser | Cys | Arg | Ser | Ser | Gln | Ser | Leu | Val |
| | | | 20 | | | | | 25 | | | | | 30 | | |
| His | Ser | Asn | Gly | Asn | Thr | Tyr | Leu | His | Trp | Tyr | Leu | Gln | Lys | Pro | Gly |
| | | 35 | | | | | 40 | | | | | 45 | | | |
| Gln | Ser | Pro | Lys | Leu | Leu | Leu | Tyr | Lys | Val | Ser | Asn | Arg | Phe | Ser | Gly |
| | 50 | | | | | 55 | | | | | 60 | | | | |
| Val | Pro | Asp | Arg | Phe | Ser | Gly | Ser | Gly | Ser | Gly | Thr | Asp | Phe | Thr | Leu |
| 65 | | | | | 70 | | | | | 75 | | | | | 80 |
| Lys | Ile | Ser | Arg | Val | Glu | Ser | Glu | Asp | Leu | Gly | Val | Tyr | Phe | Cys | Ser |
| | | | | 85 | | | | | 90 | | | | | 95 | |
| Gln | Asn | Thr | His | Val | Tyr | Thr | Phe | Gly | Gly | Gly | Thr | Lys | Leu | Glu | Ile |
| | | | 100 | | | | | 105 | | | | | 110 | | |
| Lys | Arg | Thr | Val | Ala | Ala | Pro | Ser | Val | Phe | Ile | Phe | Pro | Pro | Ser | Asp |
| | | 115 | | | | | 120 | | | | | 125 | | | |
| Glu | Gln | Leu | Lys | Ser | Gly | Thr | Ala | Ser | Val | Val | Cys | Leu | Leu | Asn | Asn |
| | 130 | | | | | 135 | | | | | 140 | | | | |
| Phe | Tyr | Pro | Arg | Glu | Ala | Lys | Val | Gln | Trp | Lys | Val | Asp | Asn | Ala | Leu |
| 145 | | | | | 150 | | | | | 155 | | | | | 160 |
| Gln | Ser | Gly | Asn | Ser | Gln | Glu | Ser | Val | Thr | Glu | Gln | Asp | Ser | Lys | Asp |
| | | | | 165 | | | | | 170 | | | | | 175 | |
| Ser | Thr | Tyr | Ser | Leu | Ser | Ser | Thr | Leu | Thr | Leu | Ser | Lys | Ala | Asp | Tyr |
| | | | 180 | | | | | 185 | | | | | 190 | | |
| Glu | Lys | His | Lys | Val | Tyr | Ala | Cys | Glu | Val | Thr | His | Gln | Gly | Leu | Ser |
| | | 195 | | | | | 200 | | | | | 205 | | | |
| Ser | Pro | Val | Thr | Lys | Ser | Phe | Asn | Arg | Gly | Glu | Cys | | | | |
| | 210 | | | | | 215 | | | | | 220 | | | | |

```
<210> SEQ ID NO 17
<211> LENGTH: 354
<212> TYPE: DNA
<213> ORGANISM: Mus musculus

<400> SEQUENCE: 17
cgcgccgaag tgcagctggt ggagtctggg ggaggcttag tgaagcctgg agagtccttg      60
aaactctcct gtgcagcctc tggattcgct ttcagttact ctgacatgtc ttgggttcgc     120
cagactccgg agaagaggct ggagtgggtc gcatacatga gtagtgctgg tgatgtcacc     180
ttctattcag acactgtgaa ggccgattc accatctcca gagacaatgc caagaacacc     240
ctgtatctgc aagtgagcag tctgaagtct gaggacacag ccatatatta ctgtgtaaga    300
caccgggacg tggctatgga ctactggggt caaggaacct cagtcaccgt ctcg          354

<210> SEQ ID NO 18
<211> LENGTH: 118
<212> TYPE: PRT
<213> ORGANISM: Mus musculus

<400> SEQUENCE: 18
```

| | | | | | | | | | | | | | | | |
|---|---|---|---|---|---|---|---|---|---|---|---|---|---|---|---|
| Arg | Ala | Glu | Val | Gln | Leu | Val | Glu | Ser | Gly | Gly | Gly | Leu | Val | Lys | Pro |
| 1 | | | | 5 | | | | | 10 | | | | | 15 | |

Gly Glu Ser Leu Lys Leu Ser Cys Ala Ala Ser Gly Phe Ala Phe Ser
            20                  25                  30

Tyr Ser Asp Met Ser Trp Val Arg Gln Thr Pro Glu Lys Arg Leu Glu
        35                  40                  45

Trp Val Ala Tyr Met Ser Ser Ala Gly Asp Val Thr Phe Tyr Ser Asp
 50                  55                  60

Thr Val Lys Gly Arg Phe Thr Ile Ser Arg Asp Asn Ala Lys Asn Thr
65                  70                  75                  80

Leu Tyr Leu Gln Val Ser Ser Leu Lys Ser Glu Asp Thr Ala Ile Tyr
                85                  90                  95

Tyr Cys Val Arg His Arg Asp Val Ala Met Asp Tyr Trp Gly Gln Gly
            100                 105                 110

Thr Ser Val Thr Val Ser
            115

<210> SEQ ID NO 19
<211> LENGTH: 660
<212> TYPE: DNA
<213> ORGANISM: Mus musculus

<400> SEQUENCE: 19
ctagccgatg ttgtgatgac ccagactcca ctctccctgc ctgtcagtct tggagatcaa    60
gcctccatct cttgcagatc tagtcagagc cttgtacaca gtaatggaaa cacctatttg   120
cattggtacc tgcagaagcc aggccagtct ccaaagctcc tgatctacaa agtttccaac   180
cgatttctg gggtcccaga caggttcagt ggcagtggat cagggacaga tttcacactc    240
aagatcagca gagtggaggc tgaggatctg ggagtttatt tctgctctca agtacacat    300
gttccgacgt tcggtggagg caccaagctg gaaatcaaac gaactgtggc tgcaccatct   360
gtcttcatct tcccgccatc tgatgagcag ttgaaatctg gaactgcctc tgttgtgtgc   420
ctgctgaata acttctatcc cagagaggcc aaagtacagt ggaaggtgga taacgccctc   480
caatcgggta actcccagga gagtgtcaca gagcaggaca gcaaggacag cacctacagc   540
ctcagcagca ccctgacgct gagcaaagca gactacgaga aacacaaagt ctacgcctgc   600
gaagtcaccc atcagggcct gagctcgccc gtcacaaaga gcttcaacag gggagagtgt   660

<210> SEQ ID NO 20
<211> LENGTH: 220
<212> TYPE: PRT
<213> ORGANISM: Mus musculus

<400> SEQUENCE: 20

Leu Ala Asp Val Val Met Thr Gln Thr Pro Leu Ser Leu Pro Val Ser
1               5                   10                  15

Leu Gly Asp Gln Ala Ser Ile Ser Cys Arg Ser Ser Gln Ser Leu Val
            20                  25                  30

His Ser Asn Gly Asn Thr Tyr Leu His Trp Tyr Leu Gln Lys Pro Gly
        35                  40                  45

Gln Ser Pro Lys Leu Leu Ile Tyr Lys Val Ser Asn Arg Phe Ser Gly
 50                  55                  60

Val Pro Asp Arg Phe Ser Gly Ser Gly Ser Gly Thr Asp Phe Thr Leu
65                  70                  75                  80

Lys Ile Ser Arg Val Glu Ala Glu Asp Leu Gly Val Tyr Phe Cys Ser
                85                  90                  95

Gln Ser Thr His Val Pro Thr Phe Gly Gly Gly Thr Lys Leu Glu Ile

```
            100             105                 110
Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
            210                 215                 220

<210> SEQ ID NO 21
<211> LENGTH: 370
<212> TYPE: DNA
<213> ORGANISM: Mus musculus

<400> SEQUENCE: 21
ggcgcgccga ggtccaactg caacagtctg ggactgaatt ggtgaagcct ggggcttcag      60
tgatactgtc ctgtaaggcc tctggctaca ccttcaccag ctactggatg cagtgggtga     120
agcagaggcc tggacaaggc cttgagtgga ttggaaatat taatcctagc aatggtggaa     180
ctagtttcaa tgaggagttc aagagtaggg ccacactgac tgtagacaaa tcctccagta     240
cagcctacat gcaactcagc agcctgacat ctgaggactc tgcggtctat tattgtgcaa     300
gagacggggg cctttacgac ggatactact ttgacttctg gggccaaggc accactctca     360
cagtctcgag                                                            370

<210> SEQ ID NO 22
<211> LENGTH: 122
<212> TYPE: PRT
<213> ORGANISM: Mus musculus

<400> SEQUENCE: 22

Arg Ala Glu Val Gln Leu Gln Gln Ser Gly Thr Glu Leu Val Lys Pro
1               5                   10                  15

Gly Ala Ser Val Ile Leu Ser Cys Lys Ala Ser Gly Tyr Thr Phe Thr
            20                  25                  30

Ser Tyr Trp Met Gln Trp Val Lys Gln Arg Pro Gly Gln Gly Leu Glu
            35                  40                  45

Trp Ile Gly Asn Ile Asn Pro Ser Asn Gly Gly Thr Ser Phe Asn Glu
        50                  55                  60

Glu Phe Lys Ser Arg Ala Thr Leu Thr Val Asp Lys Ser Ser Ser Thr
65                  70                  75                  80

Ala Tyr Met Gln Leu Ser Ser Leu Thr Ser Glu Asp Ser Ala Val Tyr
                85                  90                  95

Tyr Cys Ala Arg Asp Gly Gly Leu Tyr Asp Gly Tyr Tyr Phe Asp Phe
            100                 105                 110

Trp Gly Gln Gly Thr Thr Leu Thr Val Ser
            115                 120

<210> SEQ ID NO 23
```

```
<211> LENGTH: 663
<212> TYPE: DNA
<213> ORGANISM: Mus musculus

<400> SEQUENCE: 23
gctagccaac attgtgatga cacagtctca caaattcatg tccacattaa taggagccag      60
ggtctccatc acctgcaagg ccagtcagga tgtggatacg gctgtagcct ggtatcaaca     120
gaaaccaggt caatctccta aattattaat ttattgggca tccacccggc acactggagt     180
ccctgatcgc ttcacaggca gtggatctgg gacagatttc tctctcaccg ttagcaatgt     240
gcagtctgag gacttaacag attatttctg tcagcaatat agcagctatc ctctcacgtt     300
cggtgctggg accaagctgg agctgaaacg aactgtggct gcaccatctg tcttcatctt     360
cccgccatct gatgagcagt tgaaatctgg aactgcctct gttgtgtgcc tgctgaataa     420
cttctatccc agagaggcca agtacagtg aaggtggat aacgccctcc aatcgggtaa      480
ctcccaggag agtgtcacag agcaggacag caaggacagc acctacagcc tcagcagcac     540
cctgacgctg agcaaagcag actacgagaa acacaaagtc tacgcctgcg aagtcaccca     600
tcagggcctg agctcgcccg tcacaaagag cttcaacagg ggagagtgtt aataagcggc     660
cgc                                                                   663

<210> SEQ ID NO 24
<211> LENGTH: 216
<212> TYPE: PRT
<213> ORGANISM: Mus musculus

<400> SEQUENCE: 24

Leu Ala Asn Ile Val Met Thr Gln Ser His Lys Phe Met Ser Thr Leu
1               5                   10                  15

Ile Gly Ala Arg Val Ser Ile Thr Cys Lys Ala Ser Gln Asp Val Asp
            20                  25                  30

Thr Ala Val Ala Trp Tyr Gln Gln Lys Pro Gly Gln Ser Pro Lys Leu
        35                  40                  45

Leu Ile Tyr Trp Ala Ser Thr Arg His Thr Gly Val Pro Asp Arg Phe
    50                  55                  60

Thr Gly Ser Gly Ser Gly Thr Asp Phe Ser Leu Thr Val Ser Asn Val
65                  70                  75                  80

Gln Ser Glu Asp Leu Thr Asp Tyr Phe Cys Gln Gln Tyr Ser Ser Tyr
                85                  90                  95

Pro Leu Thr Phe Gly Ala Gly Thr Lys Leu Glu Leu Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215
```

<210> SEQ ID NO 25
<211> LENGTH: 351
<212> TYPE: DNA
<213> ORGANISM: Mus musculus

<400> SEQUENCE: 25

| | | | | | |
|---|---|---|---|---|---|
| gaagtgcagc | tgcagcagtc | tggccccgag | ctggtgaaac | ctggcgcctc | cgtgaagatc | 60 |
| tcctgcaccg | cctccggcta | caccttcacc | gactactaca | tgaactgggt | gaaacagtcc | 120 |
| cacggaaagt | ccctggaatg | gatcggagac | atcaaccca | caacggcgg | caccaactac | 180 |
| aaccagaagt | ggaagggcaa | ggccaccctg | accatccaca | agtcctccag | caccgcctac | 240 |
| atggaactgc | ggtccctgac | ctccgaggac | tccgccgtgt | acttctgtgt | gcctggcggc | 300 |
| ctgcggtcct | acttcgatta | ctggggccag | ggcaccaccc | tgacagtctc | g | 351 |

<210> SEQ ID NO 26
<211> LENGTH: 117
<212> TYPE: PRT
<213> ORGANISM: Mus musculus

<400> SEQUENCE: 26

Glu Val Gln Leu Gln Gln Ser Gly Pro Glu Leu Val Lys Pro Gly Ala
1               5                   10                  15

Ser Val Lys Ile Ser Cys Thr Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Asp Ile Asn Pro Asn Asn Gly Gly Thr Asn Tyr Asn Gln Lys Trp
    50                  55                  60

Lys Gly Lys Ala Thr Leu Thr Ile His Lys Ser Ser Thr Ala Tyr
65                  70                  75                  80

Met Glu Leu Arg Ser Leu Thr Ser Glu Asp Ser Ala Val Tyr Phe Cys
                85                  90                  95

Val Pro Gly Gly Leu Arg Ser Tyr Phe Asp Tyr Trp Gly Gln Gly Thr
            100                 105                 110

Thr Leu Thr Val Ser
        115

<210> SEQ ID NO 27
<211> LENGTH: 642
<212> TYPE: DNA
<213> ORGANISM: Mus musculus

<400> SEQUENCE: 27

| | | | | | |
|---|---|---|---|---|---|
| gacatcgtga | tgacccagtc | cctgaagttc | atgtccgcct | ccgtgggcga | ccgggtgtcc | 60 |
| atcacatgca | aggcctccca | ggatgtgtct | gccgccgtgg | cctggtatca | gcagaagcct | 120 |
| ggccagtccc | ccgagctgct | gatctactgg | gcctctaccc | ggcacaccgg | cgtgcccgac | 180 |
| agattcaccg | gctctggctc | cggcaccgac | tacaccctga | ccatctccag | cgtgcaggcc | 240 |
| gaggacctgg | ccctgtacta | ctgccagcag | cactacacca | ccccccccac | cttcggcgga | 300 |
| ggcaccaagc | tggaaatcaa | gcggaccgtg | gccgctccct | ccgtgttcat | cttcccaccc | 360 |
| tccgacgagc | agctgaagtc | cggcaccgcc | agcgtggtgt | gcctgctgaa | caacttctac | 420 |
| ccccgcgagg | ccaaggtgca | gtggaaggtg | gacaacgccc | tgcagtccgg | caactcccag | 480 |
| gaatccgtga | ccgagcagga | ctccaaggac | agcacctact | ccctgtcctc | caccctgacc | 540 | ctgtccaagg ccgactacga gaagcacaag gtgtacgcct gcgaagtgac ccaccagggc      600 ctgtccagcc ccgtgaccaa gtccttcaac cggggcgagt gc                         642

<210> SEQ ID NO 28
<211> LENGTH: 214
<212> TYPE: PRT
<213> ORGANISM: Mus musculus

<400> SEQUENCE: 28

Asp Ile Val Met Thr Gln Ser Leu Lys Phe Met Ser Ala Ser Val Gly
1               5                   10                  15

Asp Arg Val Ser Ile Thr Cys Lys Ala Ser Gln Asp Val Ser Ala Ala
            20                  25                  30

Val Ala Trp Tyr Gln Gln Lys Pro Gly Gln Ser Pro Glu Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln His Tyr Thr Thr Pro Pro
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 29
<211> LENGTH: 354
<212> TYPE: DNA
<213> ORGANISM: Mus musculus

<400> SEQUENCE: 29
caggtgcagc tgcagcagcc tggcacagag ctggtgaaac tggcgcctc cgtgaagctg       60 tcctgcaagg cctccggcta caccttcacc tcccactgga tgcactgggt gaaacagcgg      120
cctggacagg gcctggaatg gatcggcaac atcaacccct ccaacggcgg caccaactac      180
aacgagaagt tcaagtcccg ggccaccctg accgtggaca aggcctcctc caccgcctac      240
atgcagctgt cctccctgac ctccgaggac tccgccgtgt actactgcgc cagagcctac      300
tacgacttca gttggttcgt gtactggggc cagggcaccc tggtgacagt ctcg            354

<210> SEQ ID NO 30
<211> LENGTH: 118
<212> TYPE: PRT
<213> ORGANISM: Mus musculus

<400> SEQUENCE: 30

```
Gln Val Gln Leu Gln Gln Pro Gly Thr Glu Leu Val Lys Pro Gly Ala
1               5                   10                  15
Ser Val Lys Leu Ser Cys Lys Ala Ser Gly Tyr Thr Phe Thr Ser His
            20                  25                  30
Trp Met His Trp Val Lys Gln Arg Pro Gly Gln Gly Leu Glu Trp Ile
        35                  40                  45
Gly Asn Ile Asn Pro Ser Asn Gly Gly Thr Asn Tyr Asn Glu Lys Phe
    50                  55                  60
Lys Ser Arg Ala Thr Leu Thr Val Asp Lys Ala Ser Ser Thr Ala Tyr
65                  70                  75                  80
Met Gln Leu Ser Ser Leu Thr Ser Glu Asp Ser Ala Val Tyr Tyr Cys
                85                  90                  95
Ala Arg Ala Tyr Tyr Asp Phe Ser Trp Phe Val Tyr Trp Gly Gln Gly
            100                 105                 110
Thr Leu Val Thr Val Ser
        115
```

<210> SEQ ID NO 31
<211> LENGTH: 639
<212> TYPE: DNA
<213> ORGANISM: Mus musculus

<400> SEQUENCE: 31

```
gatatccaga tgacccagac ctcctccagc ctgtccgcct ccctgggcga cagagtgacc    60
atctcctgcc ggtcctccca ggacatctcc aactacctga actggtatca gcagaaaccc   120
gacggcaccg tgaagctgct gatgtacatc tcccggctgc actccggcgt gccctcagat   180
tctccggct ctggctccgg caccgagtac tccctgacca tcagcaacct ggaacaggaa    240
gatatcgcta cctacttctg tcagcagggc aacaccctgc ccctgacctt cggcgctggc   300
accaagctgg aactgaagcg gaccgtggcc gctccctccg tgttcatctt cccaccctcc   360
gacgagcagc tgaagtccgg caccgcctcc gtggtgtgcc tgctgaacaa cttctacccc   420
cgcgaggcca aggtgcagtg gaaggtggac aacgccctgc agtccggcaa ctcccaggaa   480
tccgtgaccg agcaggactc caaggacagc acctactccc tgtcctccac cctgaccctg   540
tccaaggcca actacgagaa gcacaaggtg tacgcctgcg aagtgaccca ccagggcctg   600
tccagccccg tgaccaagtc cttcaaccgg ggcgagtgc                          639
```

<210> SEQ ID NO 32
<211> LENGTH: 213
<212> TYPE: PRT
<213> ORGANISM: Mus musculus

<400> SEQUENCE: 32

```
Asp Ile Gln Met Thr Gln Thr Ser Ser Ser Leu Ser Ala Ser Leu Gly
1               5                   10                  15
Asp Arg Val Thr Ile Ser Cys Arg Ser Ser Gln Asp Ile Ser Asn Tyr
            20                  25                  30
Leu Asn Trp Tyr Gln Gln Lys Pro Asp Gly Thr Val Lys Leu Leu Met
        35                  40                  45
Tyr Ile Ser Arg Leu His Ser Gly Val Pro Ser Arg Phe Ser Gly Ser
    50                  55                  60
Gly Ser Gly Thr Glu Tyr Ser Leu Thr Ile Ser Asn Leu Glu Gln Glu
65                  70                  75                  80
```

```
Asp Ile Ala Thr Tyr Phe Cys Gln Gln Gly Asn Thr Leu Pro Leu Thr
                85                  90                  95

Phe Gly Ala Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 33
<211> LENGTH: 348
<212> TYPE: DNA
<213> ORGANISM: Mus musculus

<400> SEQUENCE: 33
caggtgacac tgaaagagtc tggcgccgag ctgatgaagc tggcgcctc cgtgaagctg        60 tcctgcaagg ccaccggcta caccttcacc ggctactgga tcgagtgggt gaaacagcgg      120
cctggacacg gcctggaatg gatcggagag atcctgcctg gctccggctc caccaactac      180
aacgagaagt tcaagggcga ggccaccttt accgccgaca cctcctccaa caccgcctac      240
atgcacctgt cctccctgac caccgaggac tccgccatct actactgcgc cagatggggc      300
gacggctcct tcgcttattg gggccagggc accctggtga cagtctcg               348

<210> SEQ ID NO 34
<211> LENGTH: 116
<212> TYPE: PRT
<213> ORGANISM: Mus musculus

<400> SEQUENCE: 34

Gln Val Thr Leu Lys Glu Ser Gly Ala Glu Leu Met Lys Pro Gly Ala
1               5                   10                  15

Ser Val Lys Leu Ser Cys Lys Ala Thr Gly Tyr Thr Phe Thr Gly Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Gly Ser Thr Asn Tyr Asn Glu Lys Phe
    50                  55                  60

Lys Gly Glu Ala Thr Phe Thr Ala Asp Thr Ser Ser Asn Thr Ala Tyr
65                  70                  75                  80

Met His Leu Ser Ser Leu Thr Thr Glu Asp Ser Ala Ile Tyr Tyr Cys
                85                  90                  95

Ala Arg Trp Gly Asp Gly Ser Phe Ala Tyr Trp Gly Gln Gly Thr Leu
            100                 105                 110

Val Thr Val Ser
        115
```

<210> SEQ ID NO 35
<211> LENGTH: 642
<212> TYPE: DNA
<213> ORGANISM: Mus musculus

<400> SEQUENCE: 35

```
gatatcgtga tgacccagtc ccagaaattc atgtccacct ccgtgggcga ccgggtgtcc    60
atcacatgca aggcctccca gaacgtgggc accgccgtgt cctggtatca gcagaagccc   120
ggccagtccc ccaagctgct gatcttctcc acctccaacc ggtacaccgg cgtgcccgac   180
agattcaccg gctctggctc cggcaccgac ttcaccctga ccatctccaa catgcagtcc   240
gaggacctgg ccgactactt ctgccagcag taccggtcct acccttcac cttcggcagc    300
ggcaccaagc tggaaatcaa gcggaccgtg gccgctccct ccgtgttcat cttcccaccc   360
tccgacgagc agctgaagtc cggcaccgcc tccgtggtgt gcctgctgaa caacttctac   420
ccccgcgagg ccaaggtgca gtggaaggtg gacaacgccc tgcagtccgg caactcccag   480
gaatccgtga ccgagcagga ctccaaggac agcacctact ccctgtcctc caccctgacc   540
ctgtccaagg ccgactacga gaagcacaag gtgtacgcct gcgaagtgac ccaccagggc   600
ctgtccagcc ccgtgaccaa gtccttcaac cggggcgagt gc                      642
```

<210> SEQ ID NO 36
<211> LENGTH: 214
<212> TYPE: PRT
<213> ORGANISM: Mus musculus

<400> SEQUENCE: 36

```
Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Gly Thr Ala
            20                  25                  30

Val Ser Trp Tyr Gln Gln Lys Pro Gly Gln Ser Pro Lys Leu Leu Ile
        35                  40                  45

Phe Ser Thr Ser Asn Arg Tyr Thr Gly Val Pro Asp Arg Phe Thr Gly
    50                  55                  60

Ser Gly Ser Gly Thr Asp Phe Thr Leu Thr Ile Ser Asn Met Gln Ser
65                  70                  75                  80

Glu Asp Leu Ala Asp Tyr Phe Cys Gln Gln Tyr Arg Ser Tyr Pro Phe
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 37
<211> LENGTH: 360
<212> TYPE: DNA
<213> ORGANISM: Mus musculus

<400> SEQUENCE: 37

```
gaagtgcagc tggtggaatc tggcggcgac ctggtgaaac ctggcggctc cctgaagctg      60
tcctgcgccg cctccggctt caccttctcc agctacggca tgtcctgggt gcgactgacc     120
cccgacaagc ggctgaatg ggtggcaacc atctccggcg gaggctccta cacctactac     180
cccgactccg tgaagggccg gttcaccatc tcccgggata tcgccaagtc caccctgtac     240
ctgcagatgt cctccctgaa gtccgaggac accgccgtgt actactgcgc ccggaagggc     300
aactacggca attacggcaa gctggcctac tggggccagg gcacctccgt gacagtctcg     360
```

<210> SEQ ID NO 38
<211> LENGTH: 120
<212> TYPE: PRT
<213> ORGANISM: Mus musculus

<400> SEQUENCE: 38

```
Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Leu Thr Pro Asp Lys Arg Leu Glu Trp Val
        35                  40                  45

Ala Thr Ile Ser Gly Gly Gly Ser Tyr Thr Tyr Tyr Pro Asp Ser Val
    50                  55                  60

Lys Gly Arg Phe Thr Ile Ser Arg Asp Ile Ala Lys Ser Thr Leu Tyr
65                  70                  75                  80

Leu Gln Met Ser Ser Leu Lys Ser Glu Asp Thr Ala Val Tyr Tyr Cys
                85                  90                  95

Ala Arg Lys Gly Asn Tyr Gly Asn Tyr Gly Lys Leu Ala Tyr Trp Gly
            100                 105                 110

Gln Gly Thr Ser Val Thr Val Ser
        115                 120
```

<210> SEQ ID NO 39
<211> LENGTH: 642
<212> TYPE: DNA
<213> ORGANISM: Mus musculus

<400> SEQUENCE: 39

```
gatatccaga tgacccagtc ccccgcctcc ctgtccgtgt ctgtgggcga cagtgtgacc      60
atcacctgtc gggcctccga gaacatctac tccaacctgg cctggtatca gcaggaacag     120
ggcaagtccc cccagctgct ggtgtacgcc gccaccaatc tggccgacgg cgtgccctcc     180
agattctccg gctctggctc cggcacccag tactccctga gatcaactc cctgcagtcc     240
gaggacttcg gctcctacta ctgccagcac ttctggggca ccccctggac cttcggcgga     300
ggcaccaagc tggaaatcaa gcggaccgtg gccgctccct ccgtgttcat cttcccaccc     360
tccgacgagc agctgaagtc cggcaccgcc tccgtggtgt gcctgctgaa caacttctac     420
ccccgcgagg ccaaggtgca gtggaaggtg acaacgccc tgcagagcgg caactcccag     480
gaatccgtga ccgagcagga ctccaaggac agcacctact ccctgtcctc caccctgacc     540
```

```
ctgtccaagg ccgactacga gaagcacaag gtgtacgcct gcgaagtgac ccaccagggc    600
ctgtccagcc ccgtgaccaa gtccttcaac cggggcgagt gc                      642
```

<210> SEQ ID NO 40
<211> LENGTH: 214
<212> TYPE: PRT
<213> ORGANISM: Mus musculus

<400> SEQUENCE: 40

```
Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Glu Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 41
<211> LENGTH: 345
<212> TYPE: DNA
<213> ORGANISM: Mus musculus

<400> SEQUENCE: 41

```
gaagtgcagc tgcagcagtc tggcgccgac ctggtgaaac ctggcgcctc cgtgaagctg    60
tcctgcacca cctccggctt caacatcaag gacatcttca tccactgggt gaaagagcgg   120
cccgagcagg gcctggaatg gatcggacgg atcgaccccg ccaacgacaa ccctaagtac   180
gaccccaagt tccagggcaa ggccaccatc tccgccgaca cctccagcaa caccgcctac   240
ctgcggctgt cctccctgac ctctgaggac accgccgtgt actactgcgc tggcggccct   300
gcctacttcg actattgggg ccagggcacc accctgacag tctcg                   345
```

<210> SEQ ID NO 42
<211> LENGTH: 115
<212> TYPE: PRT

<213> ORGANISM: Mus musculus

<400> SEQUENCE: 42

```
Glu Val Gln Leu Gln Gln Ser Gly Ala Asp Leu Val Lys Pro Gly Ala
1               5                   10                  15

Ser Val Lys Leu Ser Cys Thr Thr Ser Gly Phe Asn Ile Lys Asp Ile
            20                  25                  30

Phe Ile His Trp Val Lys Glu Arg Pro Glu Gln Gly Leu Glu Trp Ile
        35                  40                  45

Gly Arg Ile Asp Pro Ala Asn Asp Asn Pro Lys Tyr Asp Pro Lys Phe
    50                  55                  60

Gln Gly Lys Ala Thr Ile Ser Ala Asp Thr Ser Ser Asn Thr Ala Tyr
65                  70                  75                  80

Leu Arg Leu Ser Ser Leu Thr Ser Glu Asp Thr Ala Val Tyr Tyr Cys
                85                  90                  95

Ala Gly Gly Pro Ala Tyr Phe Asp Tyr Trp Gly Gln Gly Thr Thr Leu
            100                 105                 110

Thr Val Ser
        115
```

<210> SEQ ID NO 43
<211> LENGTH: 642
<212> TYPE: DNA
<213> ORGANISM: Mus musculus

<400> SEQUENCE: 43

```
gatatcgtga tgacccagtc ccacaagttc atgtccacct ccgtgggcga ccgggtgtcc    60
atctcctgca aggcctccca ggacgtgatc gccgccgtga cctggtatca gcagaagccc   120
ggccagtccc ccaagctgct gatctactgg gcctccaccc ggcacaccgg cgtgccagac   180
agattcaccg gctccggcag cggcaccgac tacaccctga ccatctccag catgcaggcc   240
gaggacctgg ccctgtacta ctgccagcag cactactcca ccccctggac cttcggcgga   300
ggcaccaagc tggaaatcaa gcggaccgtg gccgctccct ccgtgttcat cttcccaccc   360
tccgacgagc agctgaagtc cggcaccgcc tccgtggtgt gcctgctgaa caacttctac   420
ccccgcgagg ccaaggtgca gtggaaggtg gacaacgccc tgcagtccgg caactcccag   480
gaatccgtga ccgagcagga ctccaaggac agcacctact ccctgtcctc caccctgacc   540
ctgtccaagg ccgactacga gaagcacaag gtgtacgcct gcgaagtgac ccaccagggc   600
ctgtccagcc ccgtgaccaa gtccttcaac cggggcgagt gc                      642
```

<210> SEQ ID NO 44
<211> LENGTH: 214
<212> TYPE: PRT
<213> ORGANISM: Mus musculus

<400> SEQUENCE: 44

```
Asp Ile Val Met Thr Gln Ser His Lys Phe Met Ser Thr Ser Val Gly
1               5                   10                  15

Asp Arg Val Ser Ile Ser Cys Lys Ala Ser Gln Asp Val Ile Ala Ala
            20                  25                  30

Val Thr Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Tyr Thr Leu Thr Ile Ser Ser Met Gln Ala
```

```
                65                  70                  75                  80
Glu Asp Leu Ala Leu Tyr Tyr Cys Gln Gln His Tyr Ser Thr Pro Trp
                    85                  90                  95

Thr Phe Gly Gly Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 45
<211> LENGTH: 361
<212> TYPE: DNA
<213> ORGANISM: Mus musculus

<400> SEQUENCE: 45
cgcgccgagg tccaactgca acagtctgga ccagaactgg tgatgcctgg ggcttcagtg      60
aagatatcct gcaaggcttc tggctacagc ttcacaagct actatgtaca ctgggtgaag     120
cagaggcctg acagggact tgagtggatt ggatggattt atcctggaag tggtcatact      180
aagtacaatg agaagttcaa ggacaaggcc acactgacgg cagacacatc ctccagcact     240
gcctacatgc aactcagcag cctaacatct gaggactctg cggtctatta ctgtgcaaga     300 ccccccctact atagtaacta cgccgatgtc tggggcacag ggaccacggt caccgtctcg     360
a                                                                      361

<210> SEQ ID NO 46
<211> LENGTH: 120
<212> TYPE: PRT
<213> ORGANISM: Mus musculus

<400> SEQUENCE: 46

Arg Ala Glu Val Gln Leu Gln Gln Ser Gly Pro Glu Leu Val Met Pro
1               5                   10                  15

Gly Ala Ser Val Lys Ile Ser Cys Lys Ala Ser Gly Tyr Ser Phe Thr
                20                  25                  30

Ser Tyr Tyr Val His Trp Val Lys Gln Arg Pro Gly Gln Gly Leu Glu
            35                  40                  45

Trp Ile Gly Trp Ile Tyr Pro Gly Ser Gly His Thr Lys Tyr Asn Glu
        50                  55                  60

Lys Phe Lys Asp Lys Ala Thr Leu Thr Ala Asp Thr Ser Ser Ser Thr
65                  70                  75                  80

Ala Tyr Met Gln Leu Ser Ser Leu Thr Ser Glu Asp Ser Ala Val Tyr
                85                  90                  95

Tyr Cys Ala Arg Pro Pro Tyr Tyr Ser Asn Tyr Ala Asp Val Trp Gly
            100                 105                 110
```

Thr Gly Thr Thr Val Thr Val Ser
        115                 120

<210> SEQ ID NO 47
<211> LENGTH: 678
<212> TYPE: DNA
<213> ORGANISM: Mus musculus

<400> SEQUENCE: 47
ctagccgaca ttgtgatgac tcagtctcca tcctccctga ctgtgacagc aggagagaag     60
gtcactatga gctgcaagtc cagtcagagt ctgttaaaca gtggaaatca aaagaactac    120
ttgacctggt accagcagaa accagggcag cctcctaaac tgttgatcta ctgggcatcc    180
acaagggaat ctggggtccc tgatcgcttc acaggcagtg gatctggaac agatttcact    240
ctcaccatca gcagtgtgca ggctgaagac ctggcagttt attactgtca gagtgattat    300
agttatccgt acacgttcgg aggggggacc aagctggaaa taaaacgaac tgtggctgca    360
ccatctgtct tcatcttccc gccatctgat gagcagttga aatctggaac tgcctctgtt    420
gtgtgcctgc tgaataactt ctatcccaga gaggccaaag tacagtggaa ggtggataac    480
gccctccaat cgggtaactc ccaggagagt gtcacagagc aggacagcaa ggacagcacc    540
tacagcctca gcagcaccct gacgctgagc aaagcagact acgagaaaca caaagtctac    600
gcctgcgaag tcacccatca gggcctgagc tcgcccgtca caaagagctt caacagggga    660
gagtgttaat aagcggcc                                                  678

<210> SEQ ID NO 48
<211> LENGTH: 222
<212> TYPE: PRT
<213> ORGANISM: Mus musculus

<400> SEQUENCE: 48

Leu Ala Asp Ile Val Met Thr Gln Ser Pro Ser Ser Leu Thr Val Thr
1               5                   10                  15

Ala Gly Glu Lys Val Thr Met Ser Cys Lys Ser Ser Gln Ser Leu Leu
            20                  25                  30

Asn Ser Gly Asn Gln Lys Asn Tyr Leu Thr Trp Tyr Gln Gln Lys Pro
        35                  40                  45

Gly Gln Pro Pro Lys Leu Leu Ile Tyr Trp Ala Ser Thr Arg Glu Ser
    50                  55                  60

Gly Val Pro Asp Arg Phe Thr Gly Ser Gly Ser Gly Thr Asp Phe Thr
65                  70                  75                  80

Leu Thr Ile Ser Ser Val Gln Ala Glu Asp Leu Ala Val Tyr Tyr Cys
                85                  90                  95

Gln Ser Asp Tyr Ser Tyr Pro Tyr Thr Phe Gly Gly Gly Thr Lys Leu
            100                 105                 110

Glu Ile Lys Arg Thr Val Ala Ala Pro Ser Val Phe Ile Phe Pro Pro
        115                 120                 125

Ser Asp Glu Gln Leu Lys Ser Gly Thr Ala Ser Val Val Cys Leu Leu
    130                 135                 140

Asn Asn Phe Tyr Pro Arg Glu Ala Lys Val Gln Trp Lys Val Asp Asn
145                 150                 155                 160

Ala Leu Gln Ser Gly Asn Ser Gln Glu Ser Val Thr Glu Gln Asp Ser
                165                 170                 175

Lys Asp Ser Thr Tyr Ser Leu Ser Ser Thr Leu Thr Leu Ser Lys Ala
            180                 185                 190

Asp Tyr Glu Lys His Lys Val Tyr Ala Cys Glu Val Thr His Gln Gly
        195                 200                 205

Leu Ser Ser Pro Val Thr Lys Ser Phe Asn Arg Gly Glu Cys
        210                 215                 220

<210> SEQ ID NO 49
<211> LENGTH: 364
<212> TYPE: DNA
<213> ORGANISM: Mus musculus

<400> SEQUENCE: 49
cgcgccgagg tgaagctggt tgagtcagga cctggcctcg tgaaaccttc tcagtctctg    60
tctctcacct gctctgtcac tggctactcc atcaccagtg gttttactg gacctggatc   120 cggcagtttc caggcaacaa attggaatgg atgggcttca taagctacga tggtagcaat   180
aactacaacc catctctcaa aaatcgaatc tccatcactc gtgacacatc taagaaccag   240
tttttcctga agttgaattc tgtgactact gaggacacag ccacatatta ctgtgcaaga   300
ggcggaggct actatggtaa cctctttgac tactggggcc aaggcaccac tctcacagtc   360
tcga                                                               364

<210> SEQ ID NO 50
<211> LENGTH: 121
<212> TYPE: PRT
<213> ORGANISM: Mus musculus

<400> SEQUENCE: 50

Arg Ala Glu Val Lys Leu Val Glu Ser Gly Pro Gly Leu Val Lys Pro
1               5                   10                  15

Ser Gln Ser Leu Ser Leu Thr Cys Ser Val Thr Gly Tyr Ser Ile Thr
            20                  25                  30

Ser Gly Phe Tyr Trp Thr Trp Ile Arg Gln Phe Pro Gly Asn Lys Leu
        35                  40                  45

Glu Trp Met Gly Phe Ile Ser Tyr Asp Gly Ser Asn Asn Tyr Asn Pro
    50                  55                  60

Ser Leu Lys Asn Arg Ile Ser Ile Thr Arg Asp Thr Ser Lys Asn Gln
65                  70                  75                  80

Phe Phe Leu Lys Leu Asn Ser Val Thr Thr Glu Asp Thr Ala Thr Tyr
                85                  90                  95

Tyr Cys Ala Arg Gly Gly Gly Tyr Tyr Gly Asn Leu Phe Asp Tyr Trp
            100                 105                 110

Gly Gln Gly Thr Thr Leu Thr Val Ser
        115                 120

<210> SEQ ID NO 51
<211> LENGTH: 660
<212> TYPE: DNA
<213> ORGANISM: Mus musculus

<400> SEQUENCE: 51
ctagccgata ttgtgatgac tcaaactaca tcctccctgt ccgcctctct gggagacaga    60
gtcaccatca gttgcaggcc aagtcaggac attagcaatt atgtaaactg gtttcagcag   120
aaaccaggtg aactgttaa gctcctgatc ttccacacat caagattaca ctcaggagtc   180
ccatcaaggt tcagtggcag tgggtctgga acagattatt ctctcaccat tagcaccctg   240
gaacaggaag atattgccat ttacttttgc caacagggta ttacgcttcc gtggacgttc   300

```
ggtggcggca ccaagctgga aataaaacga actgtggctg caccatctgt cttcatcttc    360
ccgccatctg atgagcagtt gaaatctgga actgcctctg ttgtgtgcct gctgaataac    420
ttctatccca gagaggccaa agtacagtgg aaggtggata cgccctcca atcgggtaac     480 tcccaggaga gtgtcacaga gcaggacagc aaggacagca cctacagcct cagcagcacc    540
ctgacgctga gcaaagcaga ctacgagaaa cacaaagtct acgcctgcga agtcacccat    600
cagggcctga gctcgcccgt cacaaagagc ttcaacaggg gagagtgtta ataagcggcc    660
```

<210> SEQ ID NO 52
<211> LENGTH: 216
<212> TYPE: PRT
<213> ORGANISM: Mus musculus

<400> SEQUENCE: 52

Leu Ala Asp Ile Val Met Thr Gln Thr Thr Ser Ser Leu Ser Ala Ser
1               5                   10                  15

Leu Gly Asp Arg Val Thr Ile Ser Cys Arg Pro Ser Gln Asp Ile Ser
            20                  25                  30

Asn Tyr Val Asn Trp Phe Gln Gln Lys Pro Gly Gly Thr Val Lys Leu
        35                  40                  45

Leu Ile Phe His Thr Ser Arg Leu His Ser Gly Val Pro Ser Arg Phe
    50                  55                  60

Ser Gly Ser Gly Ser Gly Thr Asp Tyr Ser Leu Thr Ile Ser Thr Leu
65                  70                  75                  80

Glu Gln Glu Asp Ile Ala Ile Tyr Phe Cys Gln Gln Gly Ile Thr Leu
                85                  90                  95

Pro Trp Thr Phe Gly Gly Gly Thr Lys Leu Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 53
<211> LENGTH: 358
<212> TYPE: DNA
<213> ORGANISM: Mus musculus

<400> SEQUENCE: 53

```
cgcgccgagg tgcagctgaa ggagtcagga cctggcctcg tgaaaccttc tcagtctctg    60
tctctcacct gctctgtcac cggctactcc atcaccagtg cttattactg gaactggatc    120
cggcagtttc caggaaacaa agtggaatgg atgggctaca taggctacga tggtcgtaat    180
acctacaacc catctctcaa aaatcgaatc tccatcactc gtgacacatc taagaaccag    240
ttttctctga aattgaattc tctgactact gaggacacag ccacatatta ttgttcaaga    300
```

```
gagggggact acggttactc tgactactgg ggccaaggca ccactctcac agtctcga        358
```

<210> SEQ ID NO 54
<211> LENGTH: 119
<212> TYPE: PRT
<213> ORGANISM: Mus musculus

<400> SEQUENCE: 54

```
Arg Ala Glu Val Gln Leu Lys Glu Ser Gly Pro Gly Leu Val Lys Pro
1               5                   10                  15

Ser Gln Ser Leu Ser Leu Thr Cys Ser Val Thr Gly Tyr Ser Ile Thr
            20                  25                  30

Ser Ala Tyr Tyr Trp Asn Trp Ile Arg Gln Phe Pro Gly Asn Lys Val
        35                  40                  45

Glu Trp Met Gly Tyr Ile Gly Tyr Asp Gly Arg Asn Thr Tyr Asn Pro
    50                  55                  60

Ser Leu Lys Asn Arg Ile Ser Ile Thr Arg Asp Thr Ser Lys Asn Gln
65                  70                  75                  80

Phe Phe Leu Lys Leu Asn Ser Leu Thr Thr Glu Asp Thr Ala Thr Tyr
                85                  90                  95

Tyr Cys Ser Arg Glu Gly Asp Tyr Gly Tyr Ser Asp Tyr Trp Gly Gln
            100                 105                 110

Gly Thr Thr Leu Thr Val Ser
        115
```

<210> SEQ ID NO 55
<211> LENGTH: 660
<212> TYPE: DNA
<213> ORGANISM: Mus musculus

<400> SEQUENCE: 55

```
ctagccgata ttgtgatgac gcaagctaca tcctccctgt ctgcctctct gggagacaga        60
gtcaccgtca gttgcagggc aagtcaggac attaacaatt atttaaattg gtatcagcag       120
aagccagatg gaactgttaa actcctgatc tactacacat caagattaca gtcaggagtc       180
ccatcaaggt tcagtggcag tgggtctgga atagattatt ctctcaccat tagcaacctg       240
gagcaggaag attttgtcac ttacttttgc aacagagtg aaacgcttcc gtggacgttc        300
ggtggaggca ccaagctgga gctgaaacga actgtggctg caccatctgt cttcatcttc       360
ccgccatctg atgagcagtt gaaatctgga actgcctctg ttgtgtgcct gctgaataac       420
ttctatccca gagaggccaa agtacagtgg aaggtggata cgccctcca atcgggtaac        480 tcccaggaga gtgtcacaga gcaggacagc aaggacagca cctacagcct cagcagcacc       540
ctgacgctga gcaaagcaga ctacgagaaa cacaaagtct acgcctgcga agtcaccat        600 cagggcctga gctcgcccgt cacaaagagc ttcaacaggg gagagtgtta ataagcggcc       660
```

<210> SEQ ID NO 56
<211> LENGTH: 216
<212> TYPE: PRT
<213> ORGANISM: Mus musculus

<400> SEQUENCE: 56

```
Leu Ala Asp Ile Val Met Thr Gln Ala Thr Ser Ser Leu Ser Ala Ser
1               5                   10                  15

Leu Gly Asp Arg Val Thr Val Ser Cys Arg Ala Ser Gln Asp Ile Asn
            20                  25                  30
```

Asn Tyr Leu Asn Trp Tyr Gln Gln Lys Pro Asp Gly Thr Val Lys Leu
            35                  40                  45

Leu Ile Tyr Tyr Thr Ser Arg Leu Gln Ser Gly Val Pro Ser Arg Phe
 50                  55                  60

Ser Gly Ser Gly Ser Gly Ile Asp Tyr Ser Leu Thr Ile Ser Asn Leu
 65                  70                  75                  80

Glu Gln Glu Asp Phe Val Thr Tyr Phe Cys Gln Gln Ser Glu Thr Leu
                 85                  90                  95

Pro Trp Thr Phe Gly Gly Gly Thr Lys Leu Glu Leu Lys Arg Thr Val
                100                 105                 110

Ala Ala Pro Ser Val Phe Ile Phe Pro Pro Ser Asp Glu Gln Leu Lys
                115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
                180                 185                 190

Val Tyr Ala Cys Glu Val Thr His Gln Gly Leu Ser Ser Pro Val Thr
                195                 200                 205

Lys Ser Phe Asn Arg Gly Glu Cys
        210                 215

<210> SEQ ID NO 57
<211> LENGTH: 367
<212> TYPE: DNA
<213> ORGANISM: Mus musculus

<400> SEQUENCE: 57
cgcgccgagg tgcagctgca gcagtctgga cctgaactgg taaagcctgg ggcttcagtg      60
aagatgtcct gcaaggcttc tggatacaca ttcactagct atcttttgca ctgggtgaag     120
cagaagcctg gcagggcct tgagtggatt ggatatatta tccttacaa tgatggtgct      180 aagtataatg agaagttgaa aggcaaggcc acactgactt cagacaaatc ctccagcaca     240
gcctacatgg aggtcagcag cctgacctct gaggactctg cggtctatta ctgtgcaaga     300
gagggtgatt acgtgaggta ctatggtatg gactactggg gtcaaggaac ctcagtcacc     360
gtctcga                                                               367

<210> SEQ ID NO 58
<211> LENGTH: 122
<212> TYPE: PRT
<213> ORGANISM: Mus musculus

<400> SEQUENCE: 58

Arg Ala Glu Val Gln Leu Gln Gln Ser Gly Pro Glu Leu Val Lys Pro
 1                   5                  10                  15

Gly Ala Ser Val Lys Met Ser Cys Lys Ala Ser Gly Tyr Thr Phe Thr
                 20                  25                  30

Ser Tyr Leu Leu His Trp Val Lys Gln Lys Pro Gly Gln Gly Leu Glu
             35                  40                  45

Trp Ile Gly Tyr Ile Asn Pro Tyr Asn Asp Gly Ala Lys Tyr Asn Glu
 50                  55                  60

Lys Leu Lys Gly Lys Ala Thr Leu Thr Ser Asp Lys Ser Ser Ser Thr

```
                65                  70                  75                  80
Ala Tyr Met Glu Val Ser Ser Leu Thr Ser Glu Asp Ser Ala Val Tyr
                        85                  90                  95

Tyr Cys Ala Arg Glu Gly Asp Tyr Val Arg Tyr Tyr Gly Met Asp Tyr
                        100                 105                 110

Trp Gly Gln Gly Thr Ser Val Thr Val Ser
                        115                 120
```

<210> SEQ ID NO 59
<211> LENGTH: 675
<212> TYPE: DNA
<213> ORGANISM: Mus musculus

<400> SEQUENCE: 59

```
ctagccgaca ttgtgctgac tcagtcgcca tcatctctgg ctgtgtctgc aggagaaaag     60
gtcactatga gctgtaagtc cagtcaaagt gttttataca tttcaaatga gaggaattac    120
ttggcctggt accagcagaa accagggcag tctcctaaac tactgatcta ctgggcatcc    180
actaggaaat ctggtgtccc tgatcgcttc acaggcagtg gatctgggac agattttact    240
cttaccatca gcagtgtaaa agctgaagac ctggcagttt attactgtca tcaacacctc    300
tcctcgtaca cgttcggagg ggggaccaag ctggaaatca acgaactgt ggctgcacca     360
tctgtcttca tcttcccgcc atctgatgag cagttgaaat ctggaactgc ctctgttgtg    420
tgcctgctga ataacttcta tcccagagag gccaaagtac agtggaaggt ggataacgcc    480
ctccaatcgg gtaactccca ggagagtgtc acagagcagg acagcaagga cagcacctac    540
agcctcagca gcaccctgac gctgagcaaa gcagactacg agaaacacaa agtctacgcc    600
tgcgaagtca cccatcaggg cctgagctcg cccgtcacaa agagcttcaa caggggagag    660
tgttaataag cggcc                                                     675
```

<210> SEQ ID NO 60
<211> LENGTH: 221
<212> TYPE: PRT
<213> ORGANISM: Mus musculus

<400> SEQUENCE: 60

```
Leu Ala Asp Ile Val Leu Thr Gln Ser Pro Ser Ser Leu Ala Val Ser
1               5                   10                  15

Ala Gly Glu Lys Val Thr Met Ser Cys Lys Ser Ser Gln Ser Val Leu
                20                  25                  30

Tyr Ile Ser Asn Glu Arg Asn Tyr Leu Ala Trp Tyr Gln Gln Lys Pro
            35                  40                  45

Gly Gln Ser Pro Lys Leu Leu Ile Tyr Trp Ala Ser Thr Arg Lys Ser
        50                  55                  60

Gly Val Pro Asp Arg Phe Thr Gly Ser Gly Ser Gly Thr Asp Phe Thr
65                  70                  75                  80

Leu Thr Ile Ser Ser Val Lys Ala Glu Asp Leu Ala Val Tyr Tyr Cys
                85                  90                  95

His Gln His Leu Ser Ser Tyr Thr Phe Gly Gly Gly Thr Lys Leu Glu
                100                 105                 110

Ile Lys Arg Thr Val Ala Ala Pro Ser Val Phe Ile Phe Pro Pro Ser
            115                 120                 125

Asp Glu Gln Leu Lys Ser Gly Thr Ala Ser Val Cys Leu Leu Asn
        130                 135                 140

Asn Phe Tyr Pro Arg Glu Ala Lys Val Gln Trp Lys Val Asp Asn Ala
```

```
                145                 150                 155                 160
Leu Gln Ser Gly Asn Ser Gln Glu Ser Val Thr Glu Gln Asp Ser Lys
                165                 170                 175

Asp Ser Thr Tyr Ser Leu Ser Ser Thr Leu Thr Leu Ser Lys Ala Asp
            180                 185                 190

Tyr Glu Lys His Lys Val Tyr Ala Cys Glu Val Thr His Gln Gly Leu
        195                 200                 205

Ser Ser Pro Val Thr Lys Ser Phe Asn Arg Gly Glu Cys
    210                 215                 220

<210> SEQ ID NO 61
<211> LENGTH: 8
<212> TYPE: PRT
<213> ORGANISM: Mus musculus

<400> SEQUENCE: 61

Gly Tyr Thr Phe Thr Ser Tyr Trp
1               5

<210> SEQ ID NO 62
<211> LENGTH: 8
<212> TYPE: PRT
<213> ORGANISM: Mus musculus

<400> SEQUENCE: 62

Ile Tyr Pro Gly Ser Arg Ser Thr
1               5

<210> SEQ ID NO 63
<211> LENGTH: 18
<212> TYPE: PRT
<213> ORGANISM: Mus musculus

<400> SEQUENCE: 63

Cys Thr Arg Asn Gly Asp Tyr Tyr Val Ser Ser Gly Asp Ala Met Asp
1               5                   10                  15

Tyr Trp

<210> SEQ ID NO 64
<211> LENGTH: 8
<212> TYPE: PRT
<213> ORGANISM: Mus musculus

<400> SEQUENCE: 64

Gly Tyr Thr Phe Thr Ser His Trp
1               5

<210> SEQ ID NO 65
<211> LENGTH: 8
<212> TYPE: PRT
<213> ORGANISM: Mus musculus

<400> SEQUENCE: 65

Ile Asn Pro Ser Ser Gly Arg Asn
1               5

<210> SEQ ID NO 66
<211> LENGTH: 14
<212> TYPE: PRT
<213> ORGANISM: Mus musculus

<400> SEQUENCE: 66
```

```
Cys Val Arg Tyr Tyr Gly Tyr Asp Glu Ala Met Asp Tyr Trp
1               5                   10
```

<210> SEQ ID NO 67
<211> LENGTH: 8
<212> TYPE: PRT
<213> ORGANISM: Mus musculus

<400> SEQUENCE: 67

```
Gly Phe Thr Phe Ser Ser Tyr Ala
1               5
```

<210> SEQ ID NO 68
<211> LENGTH: 7
<212> TYPE: PRT
<213> ORGANISM: Mus musculus

<400> SEQUENCE: 68

```
Ile Ser Gly Val Gly Ser Thr
1               5
```

<210> SEQ ID NO 69
<211> LENGTH: 15
<212> TYPE: PRT
<213> ORGANISM: Mus musculus

<400> SEQUENCE: 69

```
Cys Ala Arg Gly Ser Asp Gly Tyr Phe Tyr Ala Met Asp Tyr Trp
1               5                   10                  15
```

<210> SEQ ID NO 70
<211> LENGTH: 8
<212> TYPE: PRT
<213> ORGANISM: Mus musculus

<400> SEQUENCE: 70

```
Gly Phe Ala Tyr Ser Thr Tyr Asp
1               5
```

<210> SEQ ID NO 71
<211> LENGTH: 8
<212> TYPE: PRT
<213> ORGANISM: Mus musculus

<400> SEQUENCE: 71

```
Ile Ser Ser Gly Gly Asp Ala Ala
1               5
```

<210> SEQ ID NO 72
<211> LENGTH: 16
<212> TYPE: PRT
<213> ORGANISM: Mus musculus

<400> SEQUENCE: 72

```
Cys Ala Arg Ser Arg Tyr Gly Asn Tyr Gly Asp Ala Met Asp Tyr Trp
1               5                   10                  15
```

<210> SEQ ID NO 73
<211> LENGTH: 8
<212> TYPE: PRT
<213> ORGANISM: Mus musculus

<400> SEQUENCE: 73

```
Gly Phe Ala Phe Ser Tyr Ser Asp
1               5
```

<210> SEQ ID NO 74
<211> LENGTH: 8
<212> TYPE: PRT
<213> ORGANISM: Mus musculus

<400> SEQUENCE: 74

Met Ser Ser Ala Gly Asp Val Thr
1               5

<210> SEQ ID NO 75
<211> LENGTH: 12
<212> TYPE: PRT
<213> ORGANISM: Mus musculus

<400> SEQUENCE: 75

Cys Val Arg His Arg Asp Val Ala Met Asp Tyr Trp
1               5                   10

<210> SEQ ID NO 76
<211> LENGTH: 8
<212> TYPE: PRT
<213> ORGANISM: Mus musculus

<400> SEQUENCE: 76

Gly Tyr Thr Phe Thr Ser Tyr Trp
1               5

<210> SEQ ID NO 77
<211> LENGTH: 8
<212> TYPE: PRT
<213> ORGANISM: Mus musculus

<400> SEQUENCE: 77

Ile Asn Pro Ser Asn Gly Gly Thr
1               5

<210> SEQ ID NO 78
<211> LENGTH: 16
<212> TYPE: PRT
<213> ORGANISM: Mus musculus

<400> SEQUENCE: 78

Cys Ala Arg Asp Gly Gly Leu Tyr Asp Gly Tyr Tyr Phe Asp Phe Trp
1               5                   10                  15

<210> SEQ ID NO 79
<211> LENGTH: 8
<212> TYPE: PRT
<213> ORGANISM: Mus musculus

<400> SEQUENCE: 79

Gly Tyr Thr Phe Thr Asp Tyr Tyr
1               5

<210> SEQ ID NO 80
<211> LENGTH: 8
<212> TYPE: PRT
<213> ORGANISM: Mus musculus

<400> SEQUENCE: 80

Ile Asn Pro Asn Asn Gly Gly Thr
1               5

```
<210> SEQ ID NO 81
<211> LENGTH: 13
<212> TYPE: PRT
<213> ORGANISM: Mus musculus

<400> SEQUENCE: 81

Cys Val Pro Gly Gly Leu Arg Ser Tyr Phe Asp Tyr Trp
1               5                   10

<210> SEQ ID NO 82
<211> LENGTH: 8
<212> TYPE: PRT
<213> ORGANISM: Mus musculus

<400> SEQUENCE: 82

Gly Tyr Thr Phe Thr Ser His Trp
1               5

<210> SEQ ID NO 83
<211> LENGTH: 8
<212> TYPE: PRT
<213> ORGANISM: Mus musculus

<400> SEQUENCE: 83

Ile Asn Pro Ser Asn Gly Gly Thr
1               5

<210> SEQ ID NO 84
<211> LENGTH: 14
<212> TYPE: PRT
<213> ORGANISM: Mus musculus

<400> SEQUENCE: 84

Cys Ala Arg Ala Tyr Tyr Asp Phe Ser Trp Phe Val Tyr Trp
1               5                   10

<210> SEQ ID NO 85
<211> LENGTH: 8
<212> TYPE: PRT
<213> ORGANISM: Mus musculus

<400> SEQUENCE: 85

Gly Tyr Thr Phe Thr Gly Tyr Trp
1               5

<210> SEQ ID NO 86
<211> LENGTH: 8
<212> TYPE: PRT
<213> ORGANISM: Mus musculus

<400> SEQUENCE: 86

Ile Leu Pro Gly Ser Gly Ser Thr
1               5

<210> SEQ ID NO 87
<211> LENGTH: 10
<212> TYPE: PRT
<213> ORGANISM: Mus musculus

<400> SEQUENCE: 87

Ala Arg Trp Gly Asp Gly Ser Phe Ala Tyr
1               5                   10

<210> SEQ ID NO 88
<211> LENGTH: 8
```

```
<212> TYPE: PRT
<213> ORGANISM: Mus musculus

<400> SEQUENCE: 88

Gly Phe Thr Phe Ser Ser Tyr Gly
1               5

<210> SEQ ID NO 89
<211> LENGTH: 8
<212> TYPE: PRT
<213> ORGANISM: Mus musculus

<400> SEQUENCE: 89

Ile Ser Gly Gly Gly Ser Tyr Thr
1               5

<210> SEQ ID NO 90
<211> LENGTH: 16
<212> TYPE: PRT
<213> ORGANISM: Mus musculus

<400> SEQUENCE: 90

Cys Ala Arg Lys Gly Asn Tyr Gly Asn Tyr Gly Lys Leu Ala Tyr Trp
1               5                   10                  15

<210> SEQ ID NO 91
<211> LENGTH: 8
<212> TYPE: PRT
<213> ORGANISM: Mus musculus

<400> SEQUENCE: 91

Gly Phe Asn Ile Lys Asp Ile Phe
1               5

<210> SEQ ID NO 92
<211> LENGTH: 8
<212> TYPE: PRT
<213> ORGANISM: Mus musculus

<400> SEQUENCE: 92

Ile Asp Pro Ala Asn Asp Asn Pro
1               5

<210> SEQ ID NO 93
<211> LENGTH: 11
<212> TYPE: PRT
<213> ORGANISM: Mus musculus

<400> SEQUENCE: 93

Cys Ala Gly Gly Pro Ala Tyr Phe Asp Tyr Trp
1               5                   10

<210> SEQ ID NO 94
<211> LENGTH: 8
<212> TYPE: PRT
<213> ORGANISM: Mus musculus

<400> SEQUENCE: 94

Gly Tyr Ser Phe Thr Ser Tyr Tyr
1               5

<210> SEQ ID NO 95
<211> LENGTH: 8
<212> TYPE: PRT
<213> ORGANISM: Mus musculus
```

<400> SEQUENCE: 95

Ile Tyr Pro Gly Ser Gly His Thr
1               5

<210> SEQ ID NO 96
<211> LENGTH: 14
<212> TYPE: PRT
<213> ORGANISM: Mus musculus

<400> SEQUENCE: 96

Cys Ala Arg Pro Pro Tyr Tyr Ser Asn Tyr Ala Asp Val Trp
1               5                   10

<210> SEQ ID NO 97
<211> LENGTH: 9
<212> TYPE: PRT
<213> ORGANISM: Mus musculus

<400> SEQUENCE: 97

Gly Tyr Ser Ile Thr Ser Gly Phe Tyr
1               5

<210> SEQ ID NO 98
<211> LENGTH: 7
<212> TYPE: PRT
<213> ORGANISM: Mus musculus

<400> SEQUENCE: 98

Ile Ser Tyr Asp Gly Ser Asn
1               5

<210> SEQ ID NO 99
<211> LENGTH: 15
<212> TYPE: PRT
<213> ORGANISM: Mus musculus

<400> SEQUENCE: 99

Cys Ala Arg Gly Gly Tyr Tyr Gly Asn Leu Phe Asp Tyr Trp
1               5                   10                  15

<210> SEQ ID NO 100
<211> LENGTH: 9
<212> TYPE: PRT
<213> ORGANISM: Mus musculus

<400> SEQUENCE: 100

Gly Tyr Ser Ile Thr Ser Ala Tyr Tyr
1               5

<210> SEQ ID NO 101
<211> LENGTH: 7
<212> TYPE: PRT
<213> ORGANISM: Mus musculus

<400> SEQUENCE: 101

Ile Gly Tyr Asp Gly Arg Asn
1               5

<210> SEQ ID NO 102
<211> LENGTH: 13
<212> TYPE: PRT
<213> ORGANISM: Mus musculus

<400> SEQUENCE: 102

```
Cys Ser Arg Glu Gly Asp Tyr Gly Tyr Ser Asp Tyr Trp
1               5                   10

<210> SEQ ID NO 103
<211> LENGTH: 8
<212> TYPE: PRT
<213> ORGANISM: Mus musculus

<400> SEQUENCE: 103

Gly Tyr Thr Phe Thr Ser Tyr Leu
1               5

<210> SEQ ID NO 104
<211> LENGTH: 8
<212> TYPE: PRT
<213> ORGANISM: Mus musculus

<400> SEQUENCE: 104

Ile Asn Pro Tyr Asn Asp Gly Ala
1               5

<210> SEQ ID NO 105
<211> LENGTH: 16
<212> TYPE: PRT
<213> ORGANISM: Mus musculus

<400> SEQUENCE: 105

Cys Ala Arg Glu Gly Asp Tyr Val Arg Tyr Tyr Gly Met Asp Tyr Trp
1               5                   10                  15

<210> SEQ ID NO 106
<211> LENGTH: 6
<212> TYPE: PRT
<213> ORGANISM: Mus musculus

<400> SEQUENCE: 106

Gln Asp Ile Gly Asn Tyr
1               5

<210> SEQ ID NO 107
<211> LENGTH: 3
<212> TYPE: PRT
<213> ORGANISM: Mus musculus

<400> SEQUENCE: 107

Tyr Thr Ser
1

<210> SEQ ID NO 108
<211> LENGTH: 11
<212> TYPE: PRT
<213> ORGANISM: Mus musculus

<400> SEQUENCE: 108

Cys Gln His Tyr Asn Thr Val Pro Pro Thr Phe
1               5                   10

<210> SEQ ID NO 109
<211> LENGTH: 11
<212> TYPE: PRT
<213> ORGANISM: Mus musculus

<400> SEQUENCE: 109

Lys Ser Leu Leu His Ser Asn Gly Ile Thr Tyr
```

<210> SEQ ID NO 110
<211> LENGTH: 3
<212> TYPE: PRT
<213> ORGANISM: Mus musculus

<400> SEQUENCE: 110

Gln Met Ser
1

<210> SEQ ID NO 111
<211> LENGTH: 11
<212> TYPE: PRT
<213> ORGANISM: Mus musculus

<400> SEQUENCE: 111

Cys Ala Gln Asn Leu Glu Leu Pro Tyr Thr Phe
1               5                   10

<210> SEQ ID NO 112
<211> LENGTH: 10
<212> TYPE: PRT
<213> ORGANISM: Mus musculus

<400> SEQUENCE: 112

Lys Ser Val Ser Thr Ser Gly Tyr Ser Phe
1               5                   10

<210> SEQ ID NO 113
<211> LENGTH: 3
<212> TYPE: PRT
<213> ORGANISM: Mus musculus

<400> SEQUENCE: 113

Leu Ala Ser
1

<210> SEQ ID NO 114
<211> LENGTH: 11
<212> TYPE: PRT
<213> ORGANISM: Mus musculus

<400> SEQUENCE: 114

Cys Gln His Ser Arg Glu Phe Pro Leu Thr Phe
1               5                   10

<210> SEQ ID NO 115
<211> LENGTH: 11
<212> TYPE: PRT
<213> ORGANISM: Mus musculus

<400> SEQUENCE: 115

Gln Ser Leu Val His Ser Asn Gly Asn Thr Tyr
1               5                   10

<210> SEQ ID NO 116
<211> LENGTH: 3
<212> TYPE: PRT
<213> ORGANISM: Mus musculus

<400> SEQUENCE: 116

Lys Val Ser
1

```
<210> SEQ ID NO 117
<211> LENGTH: 10
<212> TYPE: PRT
<213> ORGANISM: Mus musculus

<400> SEQUENCE: 117

Cys Ser Gln Asn Thr His Val Tyr Thr Phe
1               5                   10

<210> SEQ ID NO 118
<211> LENGTH: 11
<212> TYPE: PRT
<213> ORGANISM: Mus musculus

<400> SEQUENCE: 118

Gln Ser Leu Val His Ser Asn Gly Asn Thr Tyr
1               5                   10

<210> SEQ ID NO 119
<211> LENGTH: 3
<212> TYPE: PRT
<213> ORGANISM: Mus musculus

<400> SEQUENCE: 119

Lys Val Ser
1

<210> SEQ ID NO 120
<211> LENGTH: 10
<212> TYPE: PRT
<213> ORGANISM: Mus musculus

<400> SEQUENCE: 120

Cys Ser Gln Ser Thr His Val Pro Thr Phe
1               5                   10

<210> SEQ ID NO 121
<211> LENGTH: 6
<212> TYPE: PRT
<213> ORGANISM: Mus musculus

<400> SEQUENCE: 121

Gln Asp Val Asp Thr Ala
1               5

<210> SEQ ID NO 122
<211> LENGTH: 3
<212> TYPE: PRT
<213> ORGANISM: Mus musculus

<400> SEQUENCE: 122

Trp Ala Ser
1

<210> SEQ ID NO 123
<211> LENGTH: 11
<212> TYPE: PRT
<213> ORGANISM: Mus musculus

<400> SEQUENCE: 123

Cys Gln Gln Tyr Ser Ser Tyr Pro Leu Thr Phe
1               5                   10

<210> SEQ ID NO 124
```

```
<211> LENGTH: 6
<212> TYPE: PRT
<213> ORGANISM: Mus musculus

<400> SEQUENCE: 124

Gln Asp Val Ser Ala Ala
1               5

<210> SEQ ID NO 125
<211> LENGTH: 3
<212> TYPE: PRT
<213> ORGANISM: Mus musculus

<400> SEQUENCE: 125

Trp Ala Ser
1

<210> SEQ ID NO 126
<211> LENGTH: 11
<212> TYPE: PRT
<213> ORGANISM: Mus musculus

<400> SEQUENCE: 126

Cys Gln Gln His Tyr Thr Thr Pro Pro Thr Phe
1               5                   10

<210> SEQ ID NO 127
<211> LENGTH: 6
<212> TYPE: PRT
<213> ORGANISM: Mus musculus

<400> SEQUENCE: 127

Gln Asp Ile Ser Asn Tyr
1               5

<210> SEQ ID NO 128
<211> LENGTH: 3
<212> TYPE: PRT
<213> ORGANISM: Mus musculus

<400> SEQUENCE: 128

Tyr Ile Ser
1

<210> SEQ ID NO 129
<211> LENGTH: 11
<212> TYPE: PRT
<213> ORGANISM: Mus musculus

<400> SEQUENCE: 129

Cys Gln Gln Gly Asn Thr Leu Pro Leu Thr Phe
1               5                   10

<210> SEQ ID NO 130
<211> LENGTH: 6
<212> TYPE: PRT
<213> ORGANISM: Mus musculus

<400> SEQUENCE: 130

Gln Asn Val Gly Thr Ala
1               5

<210> SEQ ID NO 131
<211> LENGTH: 3
<212> TYPE: PRT
```

<213> ORGANISM: Mus musculus

<400> SEQUENCE: 131

Ser Thr Ser
1

<210> SEQ ID NO 132
<211> LENGTH: 11
<212> TYPE: PRT
<213> ORGANISM: Mus musculus

<400> SEQUENCE: 132

Cys Gln Gln Tyr Arg Ser Tyr Pro Phe Thr Phe
1               5                   10

<210> SEQ ID NO 133
<211> LENGTH: 6
<212> TYPE: PRT
<213> ORGANISM: Mus musculus

<400> SEQUENCE: 133

Glu Asn Ile Tyr Ser Asn
1               5

<210> SEQ ID NO 134
<211> LENGTH: 3
<212> TYPE: PRT
<213> ORGANISM: Mus musculus

<400> SEQUENCE: 134

Ala Ala Thr
1

<210> SEQ ID NO 135
<211> LENGTH: 11
<212> TYPE: PRT
<213> ORGANISM: Mus musculus

<400> SEQUENCE: 135

Cys Gln His Phe Trp Gly Thr Pro Trp Thr Phe
1               5                   10

<210> SEQ ID NO 136
<211> LENGTH: 6
<212> TYPE: PRT
<213> ORGANISM: Mus musculus

<400> SEQUENCE: 136

Gln Asp Val Ile Ala Ala
1               5

<210> SEQ ID NO 137
<211> LENGTH: 3
<212> TYPE: PRT
<213> ORGANISM: Mus musculus

<400> SEQUENCE: 137

Trp Ala Ser
1

<210> SEQ ID NO 138
<211> LENGTH: 11
<212> TYPE: PRT
<213> ORGANISM: Mus musculus

```
<400> SEQUENCE: 138

Cys Gln Gln His Tyr Ser Thr Pro Trp Thr Phe
1               5                   10

<210> SEQ ID NO 139
<211> LENGTH: 12
<212> TYPE: PRT
<213> ORGANISM: Mus musculus

<400> SEQUENCE: 139

Gln Ser Leu Leu Asn Ser Gly Asn Gln Lys Asn Tyr
1               5                   10

<210> SEQ ID NO 140
<211> LENGTH: 3
<212> TYPE: PRT
<213> ORGANISM: Mus musculus

<400> SEQUENCE: 140

Trp Ala Ser
1

<210> SEQ ID NO 141
<211> LENGTH: 11
<212> TYPE: PRT
<213> ORGANISM: Mus musculus

<400> SEQUENCE: 141

Cys Gln Ser Asp Tyr Ser Tyr Pro Tyr Thr Phe
1               5                   10

<210> SEQ ID NO 142
<211> LENGTH: 6
<212> TYPE: PRT
<213> ORGANISM: Mus musculus

<400> SEQUENCE: 142

Gln Asp Ile Ser Asn Tyr
1               5

<210> SEQ ID NO 143
<211> LENGTH: 3
<212> TYPE: PRT
<213> ORGANISM: Mus musculus

<400> SEQUENCE: 143

His Thr Ser
1

<210> SEQ ID NO 144
<211> LENGTH: 11
<212> TYPE: PRT
<213> ORGANISM: Mus musculus

<400> SEQUENCE: 144

Cys Gln Gln Gly Ile Thr Leu Pro Trp Thr Phe
1               5                   10

<210> SEQ ID NO 145
<211> LENGTH: 6
<212> TYPE: PRT
<213> ORGANISM: Mus musculus

<400> SEQUENCE: 145
```

```
Gln Asp Ile Asn Asn Tyr
1               5

<210> SEQ ID NO 146
<211> LENGTH: 3
<212> TYPE: PRT
<213> ORGANISM: Mus musculus

<400> SEQUENCE: 146

Tyr Thr Ser
1

<210> SEQ ID NO 147
<211> LENGTH: 11
<212> TYPE: PRT
<213> ORGANISM: Mus musculus

<400> SEQUENCE: 147

Cys Gln Gln Ser Glu Thr Leu Pro Trp Thr Phe
1               5                   10

<210> SEQ ID NO 148
<211> LENGTH: 12
<212> TYPE: PRT
<213> ORGANISM: Mus musculus

<400> SEQUENCE: 148

Gln Ser Val Leu Tyr Ile Ser Asn Glu Arg Asn Tyr
1               5                   10

<210> SEQ ID NO 149
<211> LENGTH: 3
<212> TYPE: PRT
<213> ORGANISM: Mus musculus

<400> SEQUENCE: 149

Trp Ala Ser
1

<210> SEQ ID NO 150
<211> LENGTH: 10
<212> TYPE: PRT
<213> ORGANISM: Mus musculus

<400> SEQUENCE: 150

Cys His Gln His Leu Ser Ser Tyr Thr Phe
1               5                   10
```